US009783850B2

(12) United States Patent
Frumkin et al.

(10) Patent No.: US 9,783,850 B2
(45) Date of Patent: Oct. 10, 2017

(54) IDENTIFICATION OF SOURCE OF DNA SAMPLES

(75) Inventors: Danny Frumkin, Rehovot (IL); Adam Wasserstrom, Nes-Ziona (IL)

(73) Assignee: Nucleix, Herzelya (IL)

( * ) Notice: Subject to any disclaimer, the term of this patent is extended or adjusted under 35 U.S.C. 154(b) by 211 days.

(21) Appl. No.: 13/029,719

(22) Filed: Feb. 17, 2011

(65) Prior Publication Data
US 2012/0003634 A1 Jan. 5, 2012

Related U.S. Application Data

(60) Provisional application No. 61/306,201, filed on Feb. 19, 2010.

(51) Int. Cl.
C12Q 1/68 (2006.01)

(52) U.S. Cl.
CPC ......... *C12Q 1/6881* (2013.01); *C12Q 1/6844* (2013.01); *C12Q 1/6858* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 6,764,822 B1 | 7/2004 | Butler | |
| 6,812,339 B1 | 11/2004 | Venter | |
| 2002/0152035 A1 | 10/2002 | Perlin | |
| 2004/0181048 A1 | 9/2004 | Wang | |
| 2005/0153316 A1* | 7/2005 | Jeddeloh et al. | 435/6 |
| 2005/0272065 A1* | 12/2005 | Lakey et al. | 435/6 |
| 2007/0092883 A1* | 4/2007 | Schouten | C12Q 1/6827 435/6.12 |
| 2007/0178506 A1* | 8/2007 | Martienssen et al. | 435/6 |
| 2007/0202526 A1 | 8/2007 | Nakami | |
| 2007/0207195 A1* | 9/2007 | Yarosh et al. | 424/450 |
| 2007/0275402 A1* | 11/2007 | Lo | C12Q 1/6827 435/6.11 |
| 2008/0153099 A1* | 6/2008 | Allen | C12Q 1/6851 435/6.12 |
| 2008/0286773 A1 | 11/2008 | Bender | |
| 2009/0018031 A1 | 1/2009 | Trinklein et al. | |
| 2009/0305234 A1 | 12/2009 | Olek et al. | |
| 2013/0084571 A1 | 4/2013 | Wasserstrom et al. | |

FOREIGN PATENT DOCUMENTS

| | | |
|---|---|---|
| CA | 2 699 606 A1 | 3/2009 |
| EP | 1213360 | 6/2002 |
| EP | 1748080 A2 | 1/2007 |
| EP | 2071035 | 6/2009 |
| WO | 02/12328 | 2/2002 |
| WO | 2005/040399 | 5/2005 |
| WO | WO 2007018601 A1 * | 2/2007 |
| WO | 2008/104002 | 8/2008 |
| WO | 2008/140532 A1 | 11/2008 |
| WO | WO 2009/083989 A1 | 7/2009 |
| WO | 2011/070441 | 6/2011 |
| WO | WO 2012/070037 A2 | 5/2012 |

OTHER PUBLICATIONS

Holemaon, H et al. MethylScreen: DNA methylation density monitoring using quantitative PCR. Biotechniques, vol. 43, No. 5, p. 683-693, 2007.*
Oakes, CC., et al. Evaluation of a quantitative DNA methylation analysis technique using methylation-sensitive/dependent restriction enzymes and real-time PCR. Epigenetics, vol. 1(3), p. 146-152, 2006.*
Yamagata, Y et al. Aberrant DNA methylation status in human uterine leiomyoma. Molecular Human Reproduction, vol. 15, No. 4, pp. 259-267, 2009, published online Feb. 14, 2009.*
Zeschnigk, M. et al. IGF2/H19 hypomethylation in silver-russell syndrome and isolated hemihypoplasia. European Journal of Human Genetics, vol. 16, pp. 328-334, 2008.*
Zhao, G. et al. Study on the application of parent-of-origin specific DNA methylation markers to forensic genetics. Forensic Science International, vol. 154, p. 122-127, 2005.*
Nouzova, M. et al. Epigenomic changes during leukemia cell differentiation: Analysis of histone acetylation and cytosine methylation using CpG island microarrays. J. Pharmacology and Experimental Therapeutics, vol. 311(3), p. 968-981, 2004.*
Wittenberg, AH., et al. Validation of the high-throughput marker technology DArT using the model plant Arabidopsis thaliana. Mol Gen Genomics, vol. 274, p. 30-39, 2005.*
Nakayashiki, N. et al. Studies on differentially methylated parental allele in imprinted genes. Forensic Science International: Genetics, Supplement series 1, p. 572-573, 2008.*
The International Search Report received in the corresponding International Patent Application No. PCT/IB2011/00300, dated Dec. 29, 2011.
Eads et al., "MethyLight: a high-throughput assay to measure DNA methylation," *Nucl Acids Res*, (2000), pp. 1-8, vol. 28, No. 8, e32. Especially p. 3, col. 1, para. 3.
Greiner et al., "Effectiveness of capillary electrophoresis using fluorescent-labeled primers in detecting T-cell receptor gamma gene rearrangements," *J Mol Design*, (2002), pp. 137-143, vol. 4, No. 3. Abstract only.

(Continued)

*Primary Examiner* — Prabha Chunduru
(74) *Attorney, Agent, or Firm* — Winston & Strawn LLP

(57) ABSTRACT

The present disclosure relates to methodology for fast and cost-effective identification of the source of DNA samples. DNA samples obtained from unknown or unrecognized tissues or cell types are analyzed according to the methodology described herein, yielding an identification of the tissue and/or cell type source. Identification is based on sequential biochemical procedures including methylation sensitive/dependent restriction and polymerase chain reaction, followed by analysis of the data. All biochemical steps are performed in a single test tube. The disclosure has immediate applications in forensic science for identification of the tissue source of DNA obtained from biological stains. The disclosure also has immediate applications in cancer diagnosis for identification.

25 Claims, 7 Drawing Sheets

(56) References Cited

OTHER PUBLICATIONS

Holemon et al., "MethylScreen: DNA methylation density monitoring using quantitative PCR," *Biotechniques*, (2007), pp. 683-693, vol. 43, No. 5. Especially p. 684, fig. 1, p. 684, col. 1, para. 2, p. 684, col. 3, para. 2.

Sakamoto et al., "Cell type-specific methylation profiles occurring disproportionately in CpG-less regions that delineate developmental similarity," *Genes Cells*, (2007), pp. 1123-1132, vol. 12, No. 10. Especially p. 1123, col. 1, para. 1, p. 1124, col. 1, para. 2, p. 1125, fig. 2, p. 125, col. 1, para. 2, p. 1128, col. 1, para. 3, p. 1129, col. 2, para. 2, p. 1130, col. 2, para. 1.

Von Kanel et al., "Quantitative one-step DNA methylation analysis (qOSMA) using native genomic DNA as template [online]," *Advances in Genomics*, (2010) (retrieved Nov. 22, 2011). Available on the Internet: <URL: http://www.advances-ingenomics.org/presentationsNonKanel.pdf>. Especially p. 5, p. 15.

The International Search Report received in the related application No. PCT/IB2010/003397, dated Sep. 11, 2012.

Frumkin, et al., "DNA methylation-based forensic tissue identification", *Forensic Science International: Genetics*, 2010, vol. 5, No. 5, pp. 517-524.

Frumkin, et al., "Authentication of forensic DNA samples", *Forensic Science International: Genetics*, 2001, Abstract. (XP26829808).

Fantappié et al., (2001) Lack of DNA methylation in Schistosoma mansoni. Exp Parasitol 98(3): 162-6.

Herman et al., (1996) Methylation-specific PCR: a novel PCR assay for methylation status of CpG islands. Proc Natl Acad Sci USA 93(18): 9821-6.

Martin-Magniette et al., (2005) Evaluation of the gene-specific dye bias in cDNA microarray experiments. Bioinformatics 21(9): 1995-2000.

Oakes et al., (2006) Evaluation of a quantitative DNA methylation analysis technique using methylation-sensitive/ dependent restriction enzymes and real-time PCR. Epigenetics 1(3): 146-52.

Touchman et al., Genebank accession No. G54325.1CBS16 Human EGreen *Homo sapiens* STS genomic, sequence tagged site, Aug. 23, 1999 (online). Retrieved on Feb. 20, 2011 (Feb. 20, 2011). Retrieved from the internet: URL: http://www.ncbi.nlm.nih.gov/nuccore/G54325.1.

Yagi et al., (2008) DNA methylation profile of tissue-dependent and differentially methylated regions (T-DMRs) in mouse promoter regions demonstrating tissue-specific gene expression. Genome Res 18(12): 1969-78.

Lowe et al., (1990) A computer program for selection of oligonucleotide primers for polymerase chain reactions. Nucleic Acids Res 18(7): 1757-61.

Rubin et al., (1994) Alu repeated DNAs are differentially methylated in primate germ cells. Nucleic Acids Res 22(23): 5121-7.

Final office action dated Apr. 21, 2015 for copending U.S. Appl. No. 13/492,187.

Hua et al., (2011), "Quantitative methylation analysis of multiple genes using methylation-sensitive restriction enzyme-based quantitative PCR for the detection of hepatocellular carcinoma," Experimental and Molecular Pathology, 91(1):455-60.

Reinert et al., (2011), "Comprehensive Genome Methylation Analysis in Bladder Cancer: Identification and Validation of Novel Methylated Genes and Application of These as Urinary Tumor Markers," Clin Cancer Res, 17(17):5582-92.

*Homo sapiens* KCNJ2 antisense RNA 1 (head to head) (KCNJ2-AS1), long non-coding RNA. Genebank: NR_036534.1, Nov. 5, 2013 (Nov. 5, 2013). URL: https://www.ncbi.nlm.nih.gov/nuccore/303227915; 2 pages.

*Homo sapiens* potassium voltage-gated channel subfamily J member 2 (KCNJ2), RefSeqGene (LRG_328) on chromosome 17.Genebank: NG_008798.1, Feb. 7, 2016 (Feb. 7, 2016). URL: https://www.ncbi.nlm.nih.gov/nucleotide/209969779?report=genbank&log$=nuclalign&blast_rank=2&RID=VV2JJWYR01R; 6 pages.

\* cited by examiner

IDENTIFICATION OF SOURCE OF DNA SAMPLES

This U.S. Non-Provisional patent application claims priority to U.S. Provisional Application Ser. No. 61/306,201, filed on Feb. 19, 2010, which is incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 8, 2011, is named 95280114.txt and is 65,911 bytes in size.

FIELD OF THE DISCLOSURE

The present disclosure embraces methodology for fast and cost-effective identification of the source of DNA samples. DNA samples obtained from unknown or unrecognized tissues or cell types are analyzed according to the methodology described herein, yielding an identification of the tissue and/or cell type source

INTRODUCTION

Methylation in the human genome occurs in the form of 5-methyl cytosine and is confined to cytosine residues that are part of the sequence CG (cytosine residues that are part of other sequences are not methylated). Some CG dinucleotides in the human genome are methylated, and others are not. Additionally, methylation is cell and tissue specific, such that a specific CG dinucleotide can be methylated in a certain cell and at the same time unmethylated in a different cell, or methylated in a certain tissue and at the same time unmethylated in different tissues.

Since methylation at a specific locus can vary from cell to cell, when analyzing the methylation status of DNA extracted from a plurality of cells (e.g. from a forensic sample), the signal can be mixed, showing both the methylated and unmethylated signals in varying ratios.

Various data sources are available for retrieving or storing DNA methylation data and making these data readily available to the public, for example "DNA Methylation Database (MetDB).

SUMMARY

In one aspect, there is provided a method for identifying the source of a DNA sample, comprising: (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) identifying the source of the DNA sample based on determining the likelihood of each tissue and/or cell type being the source of the DNA, wherein the tissue/cell type with the largest likelihood is determined to be the source of the DNA sample.

In one embodiment, the source is a tissue or cell type. In another embodiment, the source is a specific physiological/pathological condition. In another embodiment, the source is a specific age, or range of ages. In another embodiment, the source is male. In another embodiment, the source is female.

In another embodiment, the DNA digestion and amplification are performed in a single biochemical reaction in a single test tube. In a further embodiment, the single test tube comprises DNA template, digestion and amplification enzymes, buffers, primers, and accessory ingredients. In another further embodiment, the single test tube is closed and placed in a thermal cycler, where the single reaction takes place.

In another embodiment, the methylation-sensitive restriction endonuclease is unable to cut or digest DNA if its recognition sequence is methylated. In another embodiment, the methylation-sensitive restriction endonuclease is selected from the group consisting of AatII, Acc65I, AccI, AciI, AClI, AfeI, AgeI, ApaI, ApaLI, AscI, AsiSI, AvaI, AvaII, BaeI, BanI, BbeI, BceAI, BcgI, BfuCI, BglI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinP1I, HpaI, HpaII, Hpy166ii, Hpy188iii, Hpy99I, HpyCH4IV, KasI, MluI, MmeI, MspA1I, MwoI, NaeI, NarI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI. In a further embodiment, the methylation-sensitive restriction endonuclease is HhaI.

In another embodiment, the methylation dependent restriction endonuclease digests only methylated DNA. In a further embodiment, the methylation dependent restriction endonuclease is McrBC, McrA, or MrrA.

In another embodiment, the likelihood is determined by matching the methylation ratio of step (d) with reference ratio(s) of the same loci amplified from known tissues/cell types.

In another embodiment, the tissue and/or cell type is blood, saliva, semen, or epidermis.

In another embodiment, the restriction loci are chosen such that they produce distinct methylation ratios for specific tissues and/or cell types.

In another embodiment, the DNA sample is mammalian DNA. In a further embodiment, the mammalian DNA is DNA from a mammal selected from human, ape, monkey, rat, mouse, rabbit, cow, pig, sheep, and horse. In another further embodiment, the mammalian DNA is human DNA. In a yet further embodiment, the human DNA is from a male. In another yet further embodiment, the human DNA is from a female.

In another embodiment, the amplifying is performed using fluorescently labeled primers. In another embodiment, the signal intensity is determined by separating said amplification products by capillary electrophoresis and then quantifying fluorescence signals. In another embodiment, the amplification and determination of signal intensity are performed by real-time PCR.

There is provided a method for distinguishing between DNA samples obtained from blood, saliva, semen, and skin epidermis, comprising: (a) digesting the DNA sample with HhaI; (b) amplifying the digested DNA with forward and reverse primers for six loci set forth in SEQ ID NOs: 26-31, thereby generating an amplification product for each restriction locus; (c) determining the intensity of the signal of each amplification product; (d) calculating methylation ratios for all loci pair combinations; (e) comparing the methylation ratios calculated in step (d) to a set of reference methylation ratios obtained from DNA from blood, saliva, semen, and skin epidermis; and (f) calculating the likelihood of each of blood, saliva, semen, and skin epidermis being the source of the DNA, wherein the tissue/cell type with the largest likelihood is determined to be the source of the DNA sample.

In one embodiment, the reference methylation ratio for locus pair SEQ ID NO: 29/SEQ ID NO: 30 in blood is about 0.29. In another embodiment, the reference methylation ratio for locus pair SEQ ID NO: 29/SEQ ID NO: 30 in semen is about 2.8. In another embodiment, the reference methylation ratio for locus pair SEQ ID NO: 29/SEQ ID NO: 30 in epidermis is about 0.78.

In another aspect, there is provided a kit for determining the source of a DNA sample, wherein said kit comprises (a) a single test tube for DNA digestion and amplification using primers for specific genomic loci; and (b) instructions for calculating at least one methylation ratio and comparing it to reference methylation ratios. In one embodiment, the primers comprise forward and reverse primers for the genetic loci set forth in SEQ ID NOs: 26-31.

In another aspect, there is provided a method for determining whether a DNA sample is from blood, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) determining whether the DNA sample derives from blood based on likelihood score of blood compared with other tissue and/or cell type likelihood scores.

In another aspect, there is provided a method for determining whether a DNA sample derives from semen, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) determining whether the DNA sample derives from semen based on likelihood score of semen compared with other tissue and/or cell type likelihood scores.

In another aspect, there is provided a method for determining whether a DNA sample derives from skin epidermis, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) determining whether the DNA sample derives from skin epidermis based on likelihood score of skin epidermis compared with other tissue and/or cell type likelihood scores.

In another aspect, there is provided a method for determining whether a DNA sample derives from saliva, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) determining whether the DNA sample derives from saliva based on likelihood score of saliva compared with other tissue and/or cell type likelihood scores.

In another aspect, there is provided a method for determining whether a DNA sample derives from urine, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) determining whether the DNA sample derives from urine based on likelihood score of saliva compared with other tissue and/or cell type likelihood scores.

In another aspect, there is provided a method for determining whether a DNA sample derives from menstrual blood, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) determining whether the DNA sample derives from menstrual blood based on likelihood score of saliva compared with other tissue and/or cell type likelihood scores.

In another aspect, there is provided a method for determining whether a DNA sample derives from vaginal tissue, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; and (f) determining whether the DNA sample derives from vaginal tissue based on likelihood score of saliva compared with other tissue and/or cell type likelihood scores.

In another aspect, there is provided a method for identifying the composition of multiple sources of a DNA sample, comprising (a) digesting the DNA sample with a methylation-sensitive and/or methylation-dependent restriction endonuclease; (b) amplifying the digested DNA with at least a first and a second restriction locus, thereby generating an amplification product for each restriction locus; (c) determining the intensity of the signal of each amplification product; (d) calculating at least one methylation ratio between the intensity of the signals corresponding to the two restriction loci; (e) comparing the methylation ratio calculated in step (d) to a set of reference methylation ratios obtained from DNA of known tissues and/or cell types; (f) determining the likelihood of each tissue and/or cell type contributing to the source of DNA; and (g) determining the composition of the source DNA based on the likelihoods obtained in step (f). In one embodiment, the DNA sample comprises a mixture of DNA from more than one of blood, semen, saliva, skin epidermis, urine, menstrual blood, vaginal tissue.

Another aspect of the present invention is a kit, comprising (i) an empty first tube, (ii) a second tube comprising PCR primers that amplify specific genomic loci; and (iii) written instructions for calculating at least one methylation ratio and comparing it to reference methylation ratios, wherein DNA restriction digestion and PCR amplification are performed together in the first tube. In one embodiment, the second tube comprises primers for semen-specific loci amplification selected from the group consisting of:

```
                                       (SEQ ID NO: 68)
SD1f (AAGAGCCCATCAGGCAGGTC), (SEQ ID NO: 69)
SD1r (GTTTCTTGTCGAGCAGCACGTGGATGATG), (SEQ ID NO: 70)
SD2f (CTCCAGAACTGGAACTTCCTG), (SEQ ID NO: 71)
SD2r (GTTTCTTAACTTGGAGACGACGGCATC), (SEQ ID NO: 72)
SD3f (TGGAGGACAATGCCCTGGTG), (SEQ ID NO: 73)
SD3r (GTTTCTTGGCTTCACCTGCGACCGTCTC), (SEQ ID NO: 74)
SD4f (CCCTCCGAGTGGCCAGCAG), (SEQ ID NO: 75)
SD4r (GTTTCTGACCACTGCCGTGGGAATG), (SEQ ID NO: 76)
SD5f (CTTCTCAGCCAATGGGAAGAG), (SEQ ID NO: 77)
SD5r (ACGTAGAAGGACCCGAGGAC), (SEQ ID NO: 78)
SD6f (TACAGACAAATCACTCAGCAGC),
    and
                                       (SEQ ID NO: 79)
SD6r (GTTTCTTGTCTGACACTCGGTTGTAGGTATT).
```

In one embodiment, either or both of the forward ("f") and reverse ("r") primers are fluorescently labeled. In another embodiment, the kit further comprises a third tube with 10× reaction buffer that comprises 150 mM TRIS-HCl, 15 mM MgCl2, 0.2 mM each dntp, and 2.5 μg BSA.

In another embodiment, the third tube further comprises the HhaI restriction endonuclease. In another embodiment, the kit comprises a fourth tube comprising a control semen DNA sample, and a fifth tube comprising a control non-semen DNA sample.

Another aspect of the present invention is a method for amplifying semen-specific genomic loci using any of the kits disclosed herein. In one embodiment, the method comprises performing a restriction enzyme digest of genomic DNA and at least one PCR amplification in a single tube, wherein the PCR reaction is performed using at least one primer pair selected from the group consisting of:

```
                                           (SEQ ID NO: 68)
(1) SD1f (AAGAGCCCATCAGGCAGGTC)
    and
                                           (SEQ ID NO: 69)
    SD1r (GTTTCTTGTCGAGCAGCACGTGGATGATG), (SEQ ID NO: 70)
(2) SD2f (CTCCAGAACTGGAACTTCCTG)
    and
                                           (SEQ ID NO: 71)
    SD2r (GTTTCTTAACTTGGAGACGACGGCATC), (SEQ ID NO: 72)
(3) SD3f (TGGAGGACAATGCCCTGGTG)
    and
                                           (SEQ ID NO: 73)
    SD3r (GTTTCTTGGCTTCACCTGCGACCGTCTC), (SEQ ID NO: 74)
(4) SD4f (CCCTCCGAGTGGCCAGCAG)
    and
                                           (SEQ ID NO: 75)
    SD4r (GTTTCTGACCACTGCCGTGGGAATG), (SEQ ID NO: 76)
(5) SD5f (CTTCTCAGCCAATGGGAAGAG)
    and
                                           (SEQ ID NO: 77)
    SD5r (ACGTAGAAGGACCCGAGGAC), (SEQ ID NO: 78)
(6) SD6f (TACAGACAAATCACTCAGCAGC),
    and
                                           (SEQ ID NO: 79)
    SD6r (GTTTCTTGTCTGACACTCGGTTGTAGGTATT).
```

In one embodiment of this method, the restriction enzyme is HhaI.

One aspect of the present method for amplifying semen-specific genomic loci, comprises performing a restriction enzyme digest of genomic DNA and at least one PCR amplification in a single tube, wherein the PCR reaction is performed using at least one primer pair selected from the group consisting of:

```
                                           (SEQ ID NO: 68)
(1) SD1f (AAGAGCCCATCAGGCAGGTC)
    and
                                           (SEQ ID NO: 69)
    SD1r (GTTTCTTGTCGAGCAGCACGTGGATGATG), (SEQ ID NO: 70)
(2) SD2f (CTCCAGAACTGGAACTTCCTG)
    and
                                           (SEQ ID NO: 71)
    SD2r (GTTTCTTAACTTGGAGACGACGGCATC),
```

```
(3)  SD3f  (TGGAGGACAATGCCCTGGTG)
     and
                                              (SEQ ID NO: 73)
     SD3r  (GTTTCTTGGCTTCACCTGCGACCGTCTC), (SEQ ID NO: 74)
(4)  SD4f  (CCCTCCGAGTGGCCAGCAG)
     and
                                              (SEQ ID NO: 75)
     SD4r  (GTTTCTGACCACTGCCGTGGGAATG), (SEQ ID NO: 76)
(5)  SD5f  (CTTCTCAGCCAATGGGAAGAG)
     and
                                              (SEQ ID NO: 77)
     SD5r  (ACGTAGAAGGACCCGAGGAC),
     and (SEQ ID NO: 78)
(6)  SD6f  (TACAGACAAATCACTCAGCAGC),
     and
                                              (SEQ ID NO: 79)
     SD6r  (GTTTCTTGTCTGACACTCGGTTGTAGGTATT).
```

In one embodiment, the restriction enzyme is HhaI.

Another method of the present invention for identifying the source a DNA sample, comprises:

(a) digesting a DNA sample with at least one of a methylation-sensitive restriction endonuclease and a methylation-dependent restriction endonuclease;

(b) amplifying at least two genomic loci from the digested DNA, wherein at least one of the loci is a restriction locus;

(c) determining the signal intensity of each amplification product;

(d) calculating methylation ratios between the signal intensities of the amplification products; and (e) comparing the methylation ratios to reference values of different DNA sources, wherein the approximation of the value of a methylation ratio to the values of reference ratios of a particular DNA source indicates the source tissue of the DNA sample.

In one embodiment, the method further comprises simultaneously performing DNA profiling with tissue identification.

Another aspect of the present invention is a kit for identifying the source of a DNA sample into at least two predetermined tissue sources and for obtaining an associated confidence level, comprising (1) primers for amplification of specific genomic loci; and at least one or more reagents selected from the group consisting of (2) a reaction buffer, (3) control DNA, (4) a methylation sensitive restriction endonuclease and/or a methylation dependent restriction endonuclease, (5) a written protocol for performing tissue identification.

In one embodiment, the kit further comprises analysis software for performing tissue identification analyses.

Another kit of the present invention for identifying the source of a DNA sample as semen or non-semen and for obtaining an associated confidence level, comprising:

(a) primer mix, comprising the following primers:

```
                                              (SEQ ID NO: 68)
     SD1f  (AAGAGCCCATCAGGCAGGTC);

(SEQ ID NO: 69)
     SD1r  (GTTTCTTGTCGAGCAGCACGTGGATGATG);

(SEQ ID NO: 70)
     SD2f  (CTCCAGAACTGGAACTTCCTG);

(SEQ ID NO: 71)
     SD2r  (GTTTCTTAACTTGGAGACGACGGCATC);

(SEQ ID NO: 72)
     SD3f  (TGGAGGACAATGCCCTGGTG);

(SEQ ID NO: 73)
     SD3r  (GTTTCTTGGCTTCACCTGCGACCGTCTC);

(SEQ ID NO: 74)
     SD4f  (CCCTCCGAGTGGCCAGCAG);

(SEQ ID NO: 75)
     SD4r  (GTTTCTGACCACTGCCGTGGGAATG);

(SEQ ID NO: 76)
     SD5f  (CTTCTCAGCCAATGGGAAGAG);

(SEQ ID NO: 77)
     SD5r  (ACGTAGAAGGACCCGAGGAC);

(SEQ ID NO: 78)
     SD6f  (TACAGACAAATCACTCAGCAGC);
     and
                                              (SEQ ID NO: 79)
     SD6r  (GTTTCTTGTCTGACACTCGGTTGTAGGTATT);
```

(b) reaction buffer;

(c) HhaI restriction endonuclease;

(d) DNA polymerase (d) a written protocol for performing tissue identification.

In one embodiment, the kit further comprises control DNA samples.

Another aspect of the present invention is a kit for identifying the source of a DNA sample as semen or non-semen and for obtaining an associated confidence level, comprising at least one pair of forward (f) and reverse (r) primer pair combinations selected from the group consisting of:

```
                                              (SEQ ID NO: 68)
(1)  SD1f  (AAGAGCCCATCAGGCAGGTC)
     and
                                              (SEQ ID NO: 69)
     SD1r  (GTTTCTTGTCGAGCAGCACGTGGATGATG);

(SEQ ID NO: 70)
(2)  SD2f  (CTCCAGAACTGGAACTTCCTG)
     and
                                              (SEQ ID NO: 71)
     SD2r  (GTTTCTTAACTTGGAGACGACGGCATC);

(SEQ ID NO: 72)
(3)  SD3f  (TGGAGGACAATGCCCTGGTG)
     and
                                              (SEQ ID NO: 73)
     SD3r  (GTTTCTTGGCTTCACCTGCGACCGTCTC);

(SEQ ID NO: 74)
(4)  SD4f  (CCCTCCGAGTGGCCAGCAG)
     and
                                              (SEQ ID NO: 75)
     SD4r  (GTTTCTGACCACTGCCGTGGGAATG);

(SEQ ID NO: 76)
(5)  SD5f  (CTTCTCAGCCAATGGGAAGAG)
     and
                                              (SEQ ID NO: 77)
     SD5r  (ACGTAGAAGGACCCGAGGAC);

(SEQ ID NO: 78)
(6)  SD6f  (TACAGACAAATCACTCAGCAGC)
     and
```

```
                                                (SEQ ID NO: 79)
        SD6r (GTTTCTTGTCTGACACTCGGTTGTAGGTATT).
```

In one embodiment, the concentration of the primers in the primer mix are: 0.6 μM SD1f, 0.6 μM SD1r, 1.75 μM SD2f, 1.75 μM SD2r, 1.25 μM SD3f, 1.25 μM SD3r, 1.75 μM SD4f, 1.75 μM SD4r, 1.75 μM SD5f, 1.75 μM SD5r, 0.9 μM SD6f, and 0.9 μM SD6r.

In another embodiment, the reaction buffer comprises 150 mM TRIS-HCl, 15 mM MgCl$_2$, 0.2 mM each dntp, and 0.1 μg/μl BSA.

In one embodiment, the kit further comprises a DNA ladder.

In one embodiment, the kit further comprises comprising analysis software for performing tissue identification analyses.

Another kit for profiling and identifying the source of a DNA sample as semen or non-semen, and obtaining an associated confidence level, comprises:
(a) primers for amplifying at least one semen-specific locus;
(b) primers for amplifying at least one locus used for DNA profiling;
(c) reaction buffer;
(d) HhaI restriction endonuclease,
(e) DNA polymerase
(f) a written protocol for performing tissue identification.

In one embodiment, the kit further comprises control DNA samples.

In one embodiment, a kit is provided for profiling and identifying the tissue source of a DNA sample as semen or non-semen, and obtaining an associated confidence level, comprising:
(a) primers for amplifying at least one semen-specific locus; and
(b) primers for amplifying at least one locus used for DNA profiling.

In one embodiment of the kit at least one semen-specific locus is the L68346 locus.

In another embodiment, the primers for amplifying a 70 bp semen-specific amplification product from L68346 are a forward primer comprising the sequence of CAGCAACA-GCACCCAGCTTG (FAM) (SEQ ID NO: 80) and a reverse primer comprising the sequence of CACAGGCTCA-GTCGCGGATC (SEQ ID NO: 81).

In another embodiment, at least one semen-specific loci is the L16264 locus.

In one embodiment, the primers for amplifying a 95 bp semen-specific amplification product from L16264 are a forward primer comprising the sequence of GGACGAGT-TAACTTCCTTAATTTC (FAM) (SEQ ID NO: 82) and reverse primer comprising the sequence of GTTTCT-TCGCGGAACCTGGTTTAACTTC (SEQ ID NO: 83).

In one embodiment, the reaction buffer comprises 150 mM TRIS-HCl, 15 mM MgCl$_2$, 0.2 mM each dntp, and 0.1 μg/μl BSA.

In one embodiment, the kit further comprises at least one of (a) a DNA ladder, (b) a Material Safety Data Sheet (MSDS), and (c) analysis software for performing tissue identification analyses.

Also provided herein is a kit for identifying the source of a DNA sample as blood, saliva, semen, or skin epidermis, and for obtaining an associated confidence level, comprising:
(a) primer mix that comprises forward and reverse primers for amplifying the denoted loci as follows:

```
                                                (SEQ ID NO: 84)
1.  L91762 (forward GCAGCAGGCCGCGGAGAAG (FAM);
                                                (SEQ ID NO: 85)
            reverse AGCAGCTGTGCCGGGCCAG)

(SEQ ID NO: 80)
2.  L68346 (forward CAGCAACAGCACCCAGCTTG (JOE);
                                                (SEQ ID NO: 81)
            reverse CACAGGCTCAGTCGCGGATC)

(SEQ ID NO: 86)
3.  L50468 (forward AGGAAACCTCAGTAGCAAAATTG
                    (JOE);
                                                (SEQ ID NO: 87)
            reverse GCGAGACTTTAGGTGTGCATC)

(SEQ ID NO: 88)
4.  L14432 (forward CGTAGGCTGCGGTGAGCTC (FAM);
                                                (SEQ ID NO: 89)
            reverse GATCCATGCCCGCTGGGATG)

(SEQ ID NO: 90)
5.  L4648  (forward CAGCCTAGACGTCAAGTTACAG (JOE);
                                                (SEQ ID NO: 91)
            reverse ACGACCTCCGGATCCAACTG)

(SEQ ID NO: 92)
6.  L39664 (forward CCCAGCTGGTTGGACATGTTG (FAM);
                                                (SEQ ID NO: 93)
            reverse CACTTCCTTCGTGGACGCC)

(SEQ ID NO: 94)
7.  L30139 (forward GAGAAGCGGGAGGATGAGAC (FAM);
                                                (SEQ ID NO: 95)
            reverse CCGCATCTCCTCCGTCCTG)

(SEQ ID NO: 96)
8.  L55429 (forward GCCTTCAGCAGGAAGTCCAC (JOE);
                                                (SEQ ID NO: 97)
            reverse CCTGTGCCTCACACAGACTC)

(SEQ ID NO: 98)
9.  L62086 (forward GTGCATGGTGTCTGGTACTTC (FAM);
                                                (SEQ ID NO: 99)
            reverse GAAGCTCTCGTGGACTACTTG)

(SEQ ID NO: 100)
10. L76138 (forward CAGCCTGCTCTTCACTGCAG (JOE);
                                                (SEQ ID NO: 101)
            reverse AGAGGCCGATGAAGCCGTAG)

(SEQ ID NO: 102)
11. L15952 (forward CTCCCTGATTTACGACAAGTTC (FAM);
                                                (SEQ ID NO: 103)
            reverse GACAGTATGCTGATGCTTCTTG)

(SEQ ID NO: 104)
12. L36599 (forward AAGGGCAGAGTTCCGCTGTC (FAM);
                                                (SEQ ID NO: 105)
            reverse CGGATGCAGGAGGATCCTAG)

(SEQ ID NO: 106)
13. L26688 (forward CGGACCAGATTGCTGGTCAC (JOE);
                                                (SEQ ID NO: 107)
            reverse CGACCTTGCCAGATGTTTGAC)

(SEQ ID NO: 108)
14. L81528 (forward AGCCTCATCCACACTGACCAG (JOE);
                                                (SEQ ID NO: 109)
            reverse TCAGAGCTCTCCTATCTGGAC)

(SEQ ID NO: 110)
15. L36556 (forward GCCAGGCCGTTGATGATGAC (JOE);
                                                (SEQ ID NO: 111)
            reverse GAATATGGAGCCCTGGGCAG)
```

(b) reaction buffer;
(c) HhaI restriction endonuclease;
(d) DNA polymerase
(e) a written protocol for performing tissue identification.

In one embodiment, the kit further comprises control DNA samples.

In one embodiment, the reaction buffer comprises 150 mM TRIS-HCl, 15 mM $MgCl_2$, 0.2 mM each dntp, and 0.1 µg/µl BSA.

In one embodiment, the kit further comprises at least one of (a) a DNA ladder, (b) a Material Safety Data Sheet (MSDS), and (c) analysis software for performing tissue identification analyses.

DETAILED DESCRIPTION

Figure 1:
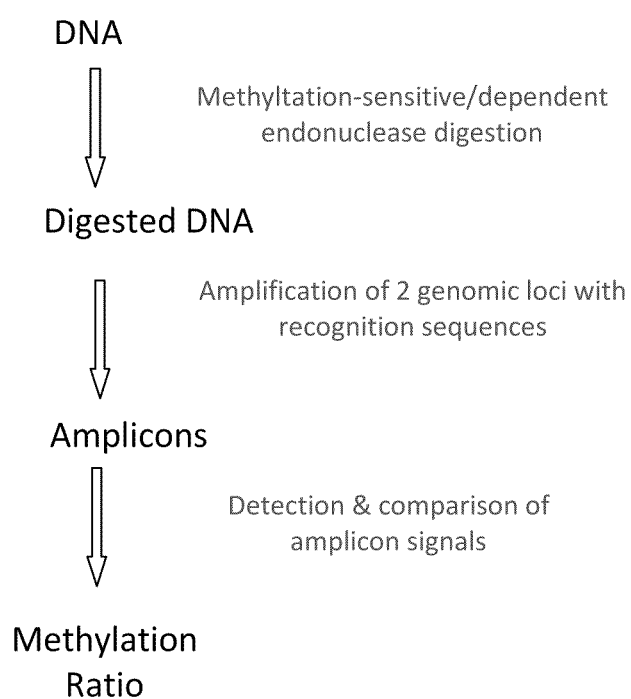
FIG. 1: schematic overview for determining a single methylation ratio.

The present disclosure relates to methods and assays that distinguish between sources of DNA, thus yielding an identification of the source tissue and/or cell type. In contrast to conventional methylation analysis methods, which determine the actual methylation levels at specific genomic loci, the methodology described herein does not rely on such determination of levels which are often highly variable between different individuals. Instead, the assay makes use of the fact, discovered by the inventors, that even when actual methylation levels between genomic loci are variable, methylation ratios between these loci are relatively constant, and can be used as indicators of the tissue source An underlying aspect of such an assay is the comparison of signals from at least two loci amplified from a digested sample of DNA, which ultimately yields a numerical ratio, which is compared to reference ratio values, indicating whether the source of the DNA sample is, in one embodiment, a specific tissue/cell type. The assays also can be used to distinguish between, for example, different physiological and pathological sources of DNA.

Specifically, and as described in more detail below, the present technology contemplates digesting a DNA sample with a methylation-sensitive and/or methylation-dependent enzyme; PCR amplification of the digested DNA with locus-specific primers; followed by measurement of the intensity of the signals from locus-specific amplification products; and determination of a methylation ratio. If the numerical ratio between the two amplification products matches or approximates that of a reference ratio of the same loci amplified from a known tissue/cell type, then the DNA sample is determined to derive from that tissue/cell type.

The assays described herein are therefore powerful, multiplex, accurate, and inexpensive techniques applicable in any setting that calls for the identification of a source of a DNA sample. Thus, the assays can be used for a large number of purposes, including but not limited to the police in a forensics capacity; the health care industry for diagnostic and therapeutic purposes; in the insurance industry to verify claims pursuant to anti-discrimination genetic laws, such as the Genetic Information Nondiscrimination Act (H.R. 493); by prosecutors and defense counsel for evidentiary purposes in criminal trials and civil proceedings and appeals; and the food and agriculture industry to verify the integrity of meats, crops, and plants such as grapevines and sources of coffee. The present technology is not limited to these non-exclusive, but representative, applications.

A significant aspect of the present disclosure is that it can readily complement and expand the usefulness of existing commercial DNA profiling kits to do more than profile a particular subject's DNA. The combination of the assays disclosed herein, such as the methylation ratio assay described in detail below, with Promega Corporation's PowerPlex® 16 kit, for example, enables one to not only profile an individual's DNA composition but also to determine the source of that individual's DNA. For example, and in no way limiting, the present technology enables one to determine if a DNA sample derives from a particular tissue and/or cell type, such as blood, saliva, or semen.

Specific compositions, methods, and/or embodiments discussed herein are merely illustrative of the present technology. Variations on these compositions, methods, or embodiments are readily apparent to a person of ordinary skill in the art, based upon the teachings of this specification, and are therefore included as part of the disclosure.

The present technology uses many conventional techniques in molecular biology and recombinant DNA. These techniques are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

DEFINITIONS

In describing the present technology, numerous technical terms are used. Unless defined otherwise, all technical and scientific terms used herein generally have the same meaning as commonly understood by one of ordinary skill in the art to which this technology belongs. As used herein, unless otherwise stated, the singular forms "a," "an," and "the" include plural reference. Thus, for example, a reference to "a nucleic acid" is a reference to one or more nucleic acids.

As used herein, the term "allele" is intended to be a genetic variation associated with a segment of DNA, i.e., one of two or more alternate forms of a DNA sequence occupying the same locus.

The term "biological sample" or "test sample" as used herein, refers to, but is not limited to, any biological sample derived from a subject. The sample suitably contains nucleic acids. In some embodiments, samples are not directly retrieved from the subject, but are collected from the environment, e.g. a crime scene or a rape victim. Examples of such samples include fluids, tissues, cell samples, organs, biopsies, etc. Suitable samples are blood, plasma, saliva, urine, sperm, hair, etc. The biological sample can also be blood drops, dried blood stains, dried saliva stains, dried underwear stains (e.g. stains on underwear, pads, tampons, diapers), clothing, dental floss, ear wax, electric razor clippings, gum, hair, licked envelope, nails, paraffin embedded tissue, post mortem tissue, razors, teeth, toothbrush, toothpick, dried umbilical cord. Genomic DNA can be extracted from such samples according to methods known in the art.

The terms "capillary electrophoresis histogram" or "electropherogram" as used herein refer to a histogram obtained from capillary electrophoresis of PCR products wherein the products were amplified from genomic loci with fluorescent primers.

The term "methylated" as used herein means methylated at a level of at least 80% (i.e. at least 80% of the DNA molecules methylated) in DNA of cells of tissues including blood, saliva, semen, epidermis, nasal discharge, buccal cells, hair, nail clippings, menstrual excretion, vaginal cells, urine, and feces.

The term "partially-methylated" as used herein means methylated at a level between 20-80% (i.e. between 20-80% of the DNA molecules methylated) in DNA of cells of tissues including blood, saliva, semen, epidermis, nasal discharge, buccal cells, hair, nail clippings, menstrual excretion, vaginal cells, urine, and feces.

The term "unmethylated" as used herein means methylated at a level less than 20% (i.e. less than 20% of the DNA molecules methylated) in DNA of cells of tissues including blood, saliva, semen, epidermis, nasal discharge, buccal cells, hair, nail clippings, menstrual excretion, vaginal cells, urine, bone, and feces. The methods provided herein have been demonstrated to distinguish methylated and unmethylated forms of nucleic acid loci in various tissues and cell types including blood, saliva, semen, epidermis, nasal discharge, buccal cells, hair, nail clippings, menstrual excretion, vaginal cells, urine, bone, and feces.

The terms "determining," "measuring," "assessing," "assaying," and "evaluating" are used interchangeably to refer to any form of quantitative or qualitative measurement, and include determining if a characteristic, trait, or feature is present or not. Assessing may be relative or absolute. "Assessing the presence of" includes determining the amount of something present, as well as determining whether it is present or absent.

The term "forensics" or "forensic science" as used herein refers to the application of a broad spectrum of methods aimed to answer questions of identity being of interest to the legal system. For example, the identification of potential suspects whose DNA may match evidence left at crime scenes, the exoneration of persons wrongly accused of crimes, identification of crime and catastrophe victims, or establishment of paternity and other family relationships.

The term "locus" (plural—loci) refers to a position on a chromosome of a gene or other genetic element. Locus may also mean the DNA at that position. A variant of the DNA sequence at a given locus is called an allele. Alleles of a locus are located at identical sites on homologous chromosomes. A control locus is a locus that is not part of the profile. A control locus can simultaneously be a restriction locus as can the profile locus. A restriction locus is a locus that comprises the restriction enzyme recognition sequence that is amplified and subsequently part of the locus amplicon. The term "natural DNA" or "natural nucleic acid" as used herein refers to, but is not limited to, nucleic acid which originates directly from the cells of a subject without modification or amplification.

The term "nucleic acid" as used herein refers to, but is not limited to, genomic DNA, cDNA, hnRNA, mRNA, rRNA, tRNA, fragmented nucleic acid, and nucleic acid obtained from subcellular organelles such as mitochondria. In addition, nucleic acids include, but are not limited to, synthetic nucleic acids or in vitro transcription products.

The term "nucleic-acid based analysis procedures" as used herein refers to any identification procedure which is based on the analysis of nucleic acids, e.g. DNA profiling.

The term "STR primers" as used herein refers to any commercially available or made-in-the-lab nucleotide primers that can be used to amplify a target nucleic acid sequence from a biological sample by PCR. There are approximately 1.5 million non-CODIS STR loci. In addition to published primer sequences, STR primers may be obtained from commercial kits for amplification of hundreds of STR loci (for example, ABI Prism Linkage Mapping Set-MD10-Applied Biosystems), and for amplification of thousands of SNP loci (for example, Illumina BeadArray linkage mapping panel). The term "CODIS STR primers" as used herein refers to STR primers that are designed to amplify any of the thirteen core SIR loci designated by the FBI's "Combined DNA Index System," specifically, the repeated sequences of TH01, TPOX, CSF1PO, VWA, FGA, D3S1358, D5S818, D7S820, D13S317, D16S539, D8S1179, D18S51, and D21S11, and the Amelogenin locus.

"Intensity of signal" refers to the intensity and/or amount of signal corresponding to amplification products of a genomic locus. For example, in capillary electrophoresis the intensity of signal of a specific locus is the number of relative fluorescence units (rfus) of its corresponding peak.

Methylation Ratio (also called "Observed Methylation Ratio") refers to relative signal intensities between a pair of loci. A methylation ratio is calculated by dividing the intensity of signal of the first locus in the locus pair by the intensity of signal of the second locus in the pair. In case that the intensity of signal of the second locus in the pair is zero, it is assigned an arbitrary small intensity signal (in order to avoid division by zero). Unless indicated otherwise, methylation ratios are calculated from DNA samples of unknown origin.

Reference Methylation Ratios (also called "Empirical Methylation Ratios") are methylation ratios obtained from samples of DNA of known sources, also called reference DNAs. Similar to methylation ratios, reference methylation ratios can be determined, for example, by dividing the intensity of signal of the first locus in the locus pair by the intensity of signal of the second locus in the pair. Because reference methylation ratios are determined from DNA of known source, one can create a library of known ratios between various pairs of genomic loci.

Probability Scores are calculated by comparing observed methylation ratios to reference methylation ratios. The probability score of a certain DNA sample at a certain methylation ratio and for a certain source tissue (e.g. blood), provide a measure of the likelihood that the DNA sample originated from that source tissue, based on the relative position of the observed methylation ratio to the distribution of reference methylation ratios of that source tissue.

Combined Probability Scores (CPS) of each tissue/cell type can be calculated from the single probability scores, for example by calculating the nth root of the product of the single probability scores (where n is the number of methylation ratios).

Likelihood: For each tissue/cell type, a Likelihood Score (LS) represents the likelihood that the DNA sample originated from that tissue/cell type. Likelihood scores for each tissue/cell type can be calculated for example as follows:

LS(tissue)=CPS(tissue)/[sum of CPSs of all tissues].

A. Selection and Isolation of DNA Sample

In one aspect, the present disclosure provides methodology for determining the tissue/cell type source of a DNA sample. For example, a DNA sample of unknown origin undergoes a procedure including one or more biochemical steps followed by signal detection. Following signal detection, the signal is analyzed to determine the source of the DNA sample. These methods are employed on any DNA sample in question, including but not limited to DNA from a body fluid stain found at a crime scene, or DNA from cancerous lesions of unknown origin.

The isolation of nucleic acids (e.g. DNA) from a biological sample may be achieved by various methods known in the art (e.g. see Sambrook et al., (1989) *Molecular Cloning: A Laboratory Manual,* 2nd ed. Cold Spring Harbor, N.Y.). Determining the source of the DNA sample may be accomplished using various strategies, including those described in the following sections.

The present inventors discovered that methylation ratio profiles can be used to determine the source of a DNA sample.

B. Methodology for Determining Methylation Levels of Genomic Loci

There are several different methods for determining the methylation level of genomic loci. Examples of methods that are commonly used are bisulfite sequencing, methylation-specific PCR, and methylation-sensitive endonuclease digestion.

Bisulfite sequencing. Bisulfite sequencing is the sequencing of bisulfite treated-DNA to determine its pattern of methylation. The method is based on the fact that treatment of DNA with sodium bisulfite results in conversion of non-methylated cytosine residues to uracil, while leaving the methylated cytosine residues unaffected. Following conversion by sodium bisulfite, specific regions of the DNA are amplified by PCR, and the PCR products are sequenced. Since in the polymerase chain reaction uracil residues are amplified as if they were thymine residues, unmethylated cytosine residues in the original DNA appear as thymine residues in the sequenced PCR product, whereas methylated cytosine residues in the original DNA appear as cytosine residues in the sequenced PCR product.

Methylation-specific PCR: Methylation specific PCR is a method of methylation analysis that, like bisulfite sequencing, is also performed on bisulfite-treated DNA, but avoids the need to sequence the genomic region of interest. Instead, the selected region in the bisulfite-treated DNA is amplified by PCR using two sets of primers that are designed to anneal to the same genomic targets. The primer pairs are designed to be "methylated-specific" by including sequences complementing only unconverted 5-methylcytosines, or conversely "unmethylated-specific," complementing thymines converted from unmethylated cytosines. Methylation is determined by the relative efficiency of the different primer pairs in achieving amplification.

It should be understood in the context of the present disclosure that methylation-specific PCR determines the methylation level of CG dinucleotides in the primer sequences only, and not in the entire genomic region that is amplified by PCR. Therefore, CG dinucleotides that are found in the amplified sequence but are not in the primer sequences are not included in the CG locus.

Methylation-sensitive endonuclease digestion: Digestion of DNA with methylation-sensitive endonucleases represents a method for methylation analysis that can be applied directly to genomic DNA without the need to perform bisulfite conversion. The method is based on the fact that methylation-sensitive endonucleases digest only unmethylated DNA, while leaving methylated DNA intact. Following digestion, the DNA can be analyzed for methylation level by a variety of methods, including gel electrophoresis, and PCR amplification of specific loci.

In methylation-sensitive endonuclease digestion, each CG locus is comprised of one or more CG dinucleotides that are part of recognition sequence(s) of the methylation-sensitive restriction endonuclease(s) that are used in the procedure. CG dinucleotides that are found in the amplified genomic region, but are not in the recognition sequence(s) of the endonuclease(s) are not included in the CG locus.

In one embodiment, the one or more CG loci that are detected are partially methylated in natural DNA, but would be unmethylated in artificial DNA. Partial methylation would be expected to result in a mixture of T and C at the position being interrogated. Hybridization would be observed to both the T specific probes/primers and the C specific probes/primers, similar to detection of a heterozygous SNP. Relative amounts of hybridization may be used to determine the relative amount of methylation. Alternatively, both C and T would be observed upon bisulfite sequencing. Alternatively, fluorescent signals corresponding to amplification products of methylated or partially methylated CG loci can be detected.

C. Methylation Ratio Assay

Figure 2:
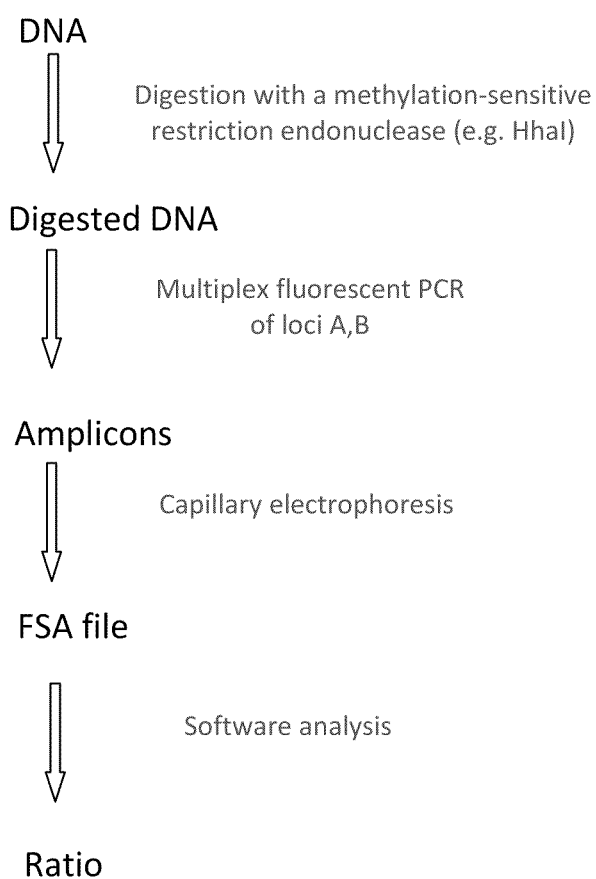
FIG. 2: schematic details for determining a single methylation ratio.
Figure 3:
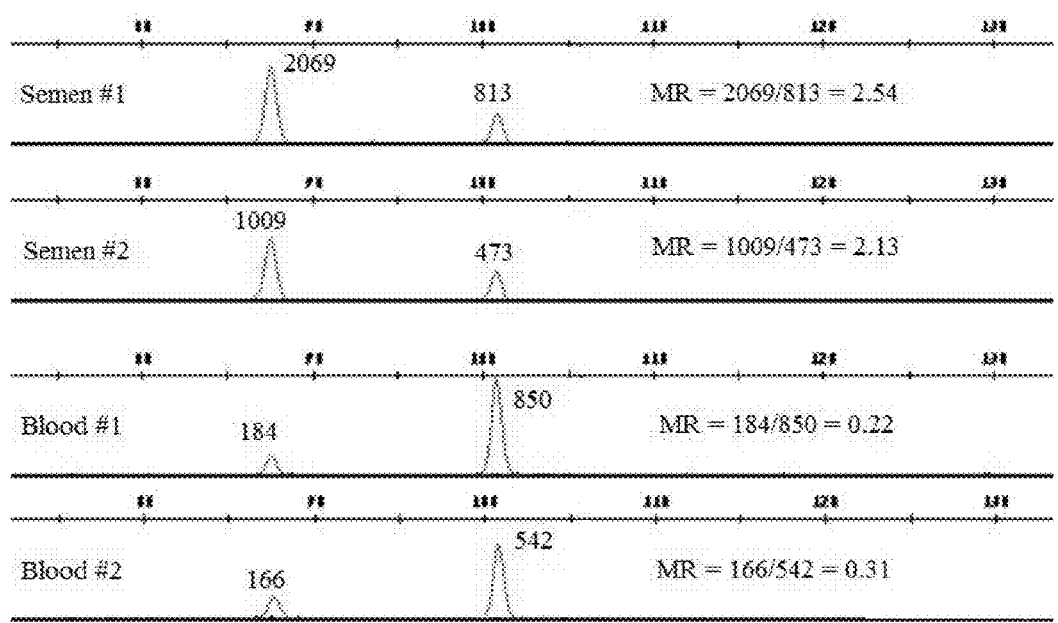
FIG. 3: Methylation ratios in semen and blood DNA samples in a specific pair of loci. In semen, the methylation ratio is about 2.5, while in blood the methylation ratio is about 0.25. Numbers next to each peak are the relative fluorescence units (rfu) level of that peak. Notice that the methylation ratio is independent of the absolute rfu levels.

As mentioned above, one particular assay of the present disclosure involves the quantitative comparison of intensity of the signals from a pair of locus-specific amplification products produced by performing a Polymerase Chain Reaction on restriction-digested DNA. See, e.g., FIGS. 1 and 2. The numerical ratio of intensities allows one to identify the tissue/cell type source of the DNA sample. For example, in one embodiment, locus 1 and locus 2 can be amplified using fluorescently labeled primers, separated by electrophoresis, and the intensity of the signals is the relative fluorescence units (rfu) of peaks corresponding to the loci. See, e.g., FIG. 3. The intensity of the signals will correspond to the successfulness of amplification of locus 1 and locus 2 from the source DNA template. By comparing rfu between the two amplification products one can calculate a ratio that reflects whether there is more or less of one amplification product than another.

In addition, however, one aspect of this assay includes the predetermination of the expected methylation ratios from various types of tissues/cell types. Thus, the template DNA that is subject to analysis is first digested with a methylation-sensitive restriction endonuclease before it is cycled through the PCR amplification protocol. It is not necessary for both primer pairs to have a similar amplification efficiency, nor is it necessary to have knowledge of the absolute methylation levels. In order to be able to correlate an observed methylation ratio with a specific tissue/cell type, one of ordinary skill in the art may compare the observed ratio with ratios obtained empirically from DNA samples of known origin.

With this premise, the present assays comprise digesting a DNA sample with a methylation-sensitive and/or methylation-dependent enzyme, performing a PCR amplification reaction on the digested DNA, and determining the intensity of the signals from locus-specific amplification products. As mentioned, the intensity of signals can be quantified or measured by using fluorescent PCR. If the numerical ratio between the two amplification products matches or approximates that of the reference ratio of the same loci amplified from a known tissue/cell type, then the test DNA sample is determined to be of that tissue/cell type.

This particular methylation ratio assay does not depend upon identifying or obtaining measurements of the absolute methylation fraction or level of selected loci. In addition, this particular methylation ratio assay does not depend upon the efficiencies of the primer pairs used, does not necessitate that both primer pairs have similar efficiencies, is not reliant upon amount of input template DNA, is not reliant upon specific thermocycler machine and reaction conditions. Rather, the assay determines the ratio between two signals which correspond to the ratio of methylation levels in the different loci. By this manner, the quantity or concentration of starting DNA material in the sample is irrelevant to the analysis and does not skew the output results. That is, the ratio of signal levels between a first locus and a second locus will remain constant regardless of how much DNA is used as a template for PCR and regardless of the number of amplification cycles that are run on the PCR thermocycler. For example, a methylation ratio of 10 between loci 1 and 2 will remain the same whether the input DNA represents methylation levels of 0.9 and 0.09 (90% methylation in locus 1 and 9% in 2), or 0.5 and 0.05 (50% methylation in locus 1 and 5% in 2), etc.

The methylation ratio assay of the present disclosure has several advantages over other approaches for analyzing methylation. For instance, this assay is insensitive to various "noise" factors inherent when relying on the absolute quantification of methylation level, since such quantification is sensitive to noise and fluctuates as a consequence of changes in template DNA concentration, thermocycler manufacturer, PCR conditions, and presence of inhibitors. Instead, the presently-calculated methylation ratios are insensitive to such factors, since the analyzed loci are co-amplified in the same reaction and are therefore subject to the effects of such disparities. Thus, the present methodology does not require absolute quantification of genomic targets or amplicons; and the assay is a single stand-alone reaction with no need for a standard curve or any external controls.

The methylation ratio assay can be performed on very small quantities of DNA in a single biochemical reaction and is therefore an inexpensive, rapid, and powerful method for establishing, for example, the tissue/cell type source of a DNA sample. An important feature of the design of the present methods is that it can be combined with other PCR-based procedures, such as DNA profiling, in a single biochemical reaction.

In addition, the assay can detect useful biological information and can perform the task of identifying the source of DNA when simple determination of actual methylation levels fails. The assay relies on methylation ratios between samples, which are relatively constant between different individuals, and does not rely on actual methylation levels of any specific locus, which vary very significantly between different individuals.

This assay therefore provides a useful biochemical marker in the form of, in one example, a numerical ratio, that can be used to differentiate between different sources of DNA. More particular details of this exemplary assay follow.

(1). Primers for Locus-Specific Amplification

Accordingly, an aspect of the present disclosure concerns obtaining a "methylation ratio" (MR) in which the intensities of signals of amplification products of DNA loci produced from fluorescent PCR are compared to one another in order to calculate ratios between pairs of loci, e.g., Loci #1 vs. Loci #2; Loci #1 vs. Loci #3; Loci #1 vs. Loci #4; Loci #2 vs. Loci #3, Loci #2 vs. Loci #4, and so on. When this technique is used to determine the source of a DNA sample, the primers that are used in the methylation ratio amplification reactions are chosen so as to amplify a pair of loci that are differentially methylated in various tissues/cell types.

In one embodiment, primer pairs are used to amplify pairs of loci selected from the group of pairs consisting of D3S1358/D18S51, D3S1358/D7S820, D3S1358/Penta_D, D3S1358/TPOX, D3S1358/FGA, TH01/Penta_D, D21S11/D18S51, D21S11/D7S820, D21S11/Penta_D, D21S11/AMEL, D21S11/TPOX, D21S11/FGA, D5S818/D18S51, vWA/D18S51, D5S818/Penta_E, vWA/Penta_E, D5S818/D7S820, D5S818/Penta_D, D5S818/TPOX, D5S818/FGA, D13S317/D7S820, D13S317/Penta_D, D13S317/TPOX, D13S317/FGA, D16S539/D7S820, CSF1PO/D7S820, vWA/D7S820, D8S1179/D7S820, D16S539/TPOX, D16S539/FGA, CSF1PO/Penta_D, CSF1PO/TPOX, vWA/Penta_D, AMEL/TPOX, AMEL/FGA, vWA/D8S1179, vWA/TPOX, vWA/FGA, D8S1179/TPOX, D8S1179/FGA.

In another embodiment, the restriction loci amplicons are smaller than the smallest amplicons used in DNA profiling, which is about 100 bps in size.

One consideration for selecting which two pairs of primers (a first pair and a second pair) to use to amplify two loci (1) and (2) is the degree to which the two loci are differentially methylated in various tissues/cell types. Thus, for example, a pair of loci whose methylation ratio is greater than 1 in one tissue/cell type, and less than 1 is all other tissues/cell types can be used to design primers for the methylation ratio amplification assay.

(2). Selection of Loci for Amplification

The only requirements for a pair of genomic loci to be used in the present methodology are that each should contain at least one recognition sequence for the methylation sensitive/dependent enzyme (e.g. GCGC in the case of HhaI), and that the methylation ratio should not be uniform across all tissues/cell types.

There are no other requirements for the loci. Specifically, loci do not need to be positioned on any specific chromosome or genomic position, they do not need to be of any specific length, do not necessarily need to be single-copy in the genome, etc.

In order to find recognition sequences for specific endonucleases, a person ordinarily skilled in the art can download any desired genome, and find the locations of any specific endonuclease, which are the locations of the substring of the recognition sequence (e.g. GCGC for HhaI) in the entire string of the genome.

In order to identify candidate pairs of genomic loci whose methylation ratios is not expected to be uniform in different tissues/cell types, and therefore "informative," a person ordinarily skilled in the art can randomly choose genomic loci and empirically test their usefulness for the assay, or search published data regarding differential methylation of specific genomic regions in different tissues/cell types. See Eckhardt et al, "DNA methylation profiling of human chromosomes 6, 20 and 22" (2006), Nature Genetics 38, 1378-1385 and Straussman et al., "Developmental programming of CpG island methylation profiles in the human genome" (2009), Nature Structural and Molecular Biology 16, 564-571.

There is published data regarding methylation levels in various genomic regions. Methylation ratios can theoretically be deduced from such data if actual methylation levels are provided. However, in reality, in the context of the present assay, this is not feasible because: (1) published methylation levels are qualitative rather than quantitative (i.e. methylated vs. unmethylated), and for purposes of ratios a numerical value is required; (2) methylation levels between tissues relates to methylation of regions (containing several CGs) rather than specific CGs. Comparing methylation levels between regions is less sensitive than comparing methylation levels between individual CGs, is less applicable to degraded samples (which contain shorter fragments), and can only be applied to CG-rich genomic regions (e.g. CG islands); (3) existing data is either on a small set of samples or from pooled DNA, and in either case this is insufficient for drawing statistical conclusions on the entire human population. Methylation ratios should be obtained from a number of individuals large enough for reaching statistical significance; and (4) Existing data is from a limited set of tissues/cell types. For example, there is no published data on comparison of methylation levels between all forensically relevant tissues (blood, saliva, semen, urine, skin epidermis, vaginal excretion).

Although the chosen genomic loci can be of any length, it may be advantageous to use relatively short amplicons (less than ~100 bp), since shorter amplicons are more likely to be intact in degraded DNA. In addition, if the assay is intended for use together with DNA profiling, such short amplicons can be useful since their size does not overlap with the size of the fragments commonly used for DNA profiling.

(3). Methylation-Sensitive Restriction Endonucleases

A second consideration of the present methodology is the selection of loci that are or are not cut or digested by a methylation-sensitive and/or methylation-dependent restriction endonuclease. The endonuclease is selected if, for instance, it is unable to cut the DNA strand if its recognition sequence in that locus is methylated. Thus, in the context of locus (1), which is methylated, and locus (2), which is not methylated, an endonuclease like HhaI or HpaII will not digest locus (1) but will digest locus (2). Accordingly, the selection of loci for amplification in the methylation ratio assay may also take into account the presence of methylation-sensitive restriction endonuclease recognition sequences within each locus.

In light of the foregoing, therefore, exemplary characteristics of a suitable pair of loci includes (A) their comparative methylation ratios in different tissue/cell types, and (B) that both loci contain at least one recognition sequence recognized by the same methylation-sensitive restriction endonuclease. In another embodiment, each locus further comprises a short tandem repeat sequence (STR).

Forward and reverse primers can then be designed to anneal to a region of DNA that flanks the recognition sequence of the loci.

Accordingly, in the case of a methylation-sensitive enzyme, if a locus is methylated it will (A) not be digested but (B) it will be amplified. Conversely, if a locus is unmethylated, it will (A) be digested but (B) not amplified. In the case of a methylation-dependent enzyme, the situation is vice versa.

(4). Creation of Reference Distributions

Reference distributions are distributions of methylation ratios obtained from samples of DNA of known sources. For example, a reference distribution for saliva for SEQ26/SEQ31 may consist of 50 methylation ratios of SEQ26/SEQ31 observed and calculated from saliva samples obtained from 50 different individuals.

Thus, to devise reference ratios for different tissues/cell types, the person of ordinary skill in the art can, for example, (1) identify a pair of loci that each contain a recognition sequence for the endonuclease (either methylation-sensitive or methylation-dependent) and which are known to be non-uniform methylation ratios across the different tissues/cell types; (2) digest a sample of DNA from a known tissue/cell type; (3) perform a PCR amplification reaction with PCR primers that are designed to amplify the first and second loci; and (4) determine the intensity of the amplification signals.

The methylation ratio is then calculated by dividing the intensity of the first locus amplification product by the second locus amplification product, or vice versa. If the amplification is performed by fluorescence PCR, then the intensity signal of each amplification product can be readily measured and reported in terms of its relative fluorescent units (rfu). In such a case, the methylation ratio can be obtained by dividing the numerical value of the rfu of the first locus amplification product by the rfu of the second locus amplification product to yield a single number that reflects the methylation ratio between the two known and selected loci from the reference DNA sample. The measurement of fluorescence signals can be performed automatically and the calculation of intensity signal ratios performed by computer software. In order to avoid the problem of division by 0, in case the signal of the denominator is 0, it may arbitrarily be assigned a small positive value.

The foregoing is an example of how the person of skill in the art may systematically determine methylation ratios between two loci selected from DNA of a known tissue/cell type. In so doing, the ordinarily skilled person can create a library of known ratios between various known pairs of genomic loci.

(5). Determining the Tissue/Cell Type Source of DNA

The ordinarily skilled person can determine the most likely source tissue/cell type from the list of methylation ratios, for example, as follows:

1. For each observed methylation ratio, calculate probability scores (between 0-1), one for each tissue/cell type. One way to calculate the probability score for a specific tissue is as follows: one minus two times the absolute difference between 0.5 and the value of the cumulative distribution function of the corresponding reference distribution (of that tissue/cell type) at the observed methylation ratio. This measures how close the observed methylation ratio is to the mean of the specific reference distribution.

2. For each tissue/cell type, calculate a Combined Probability Score (CPS) based on all probability scores of that tissue/cell type as follows:

CPS=n-th root of the product of all probability scores, where n is the number of probability scores 3. For each tissue/cell type, calculate a Likelihood Score (LS) as follows:

LS(tissue)=CPS(tissue)/[sum of CPSs of all tissues]

4. The most likely tissue is the tissue with the highest likelihood score.

(6). Capillary Electrophoresis

The rapidity of the analysis is evident in consideration of the use of, for instance, capillary electrophoresis to separate numerous amplification products produced from the amplification of multiple pairs of target loci. As described above the present methylation ratio assay can be performed on multiple loci, and in each case a methylation ratio is calculated for each pair of loci separately. For example, if four loci (A,B,C,D) are co-amplified in the reaction, six different methylation ratios can be calculated, i.e.: A/B, A/C, A/D, B/C, B/D, C/D.

Accordingly, if "n" loci are co-amplified, then $(n^2-n)/2$ different ratios can be calculated. Therefore, the amount of information that is provided by the present methylation assay rises exponentially with the number of analyzed loci. Capillary electrophoresis, as opposed to real-time PCR amplification methods, can distinguish between a large number of loci in a single run. For example, for DNA profiling, 17 genomic loci are routinely co-amplified from a particular DNA sample, and analyzed together. As a consequence, the performance of the present methylation ratio assay on all 17 loci yields 136 independent methylation ratios. Real-time PCR cannot simultaneously distinguish in a single reaction those numbers of discrete amplification products necessary to produce 136 ratios. About four loci can by distinguished by real time PCR, which corresponds to the calculation of only six ratios.

By contrast, capillary electrophoresis can readily separate out amplification products from all paired permutations of 17 loci and can therefore readily produce data to simultaneously calculate all 136 methylation ratios in a single reaction. Theoretically, hundreds of loci can be run together and separated in a single capillary electrophoresis run.

(7). Loci, Primers, and Commercially Available Profiling Kits

Any pair of loci can be used according to the present disclosure to calculate methylation ratios. As discussed elsewhere herein exemplary characteristics of a suitable pair of loci includes (A) they exhibit non uniform methylation ratios in different tissues, (B) that both loci contain at least one recognition sequence recognized by the same methylation-sensitive and/or methylation dependent restriction endonuclease, and, optionally, that (C) each locus contains a short tandem repeat (STR) sequence.

One collection of loci that is used for DNA profiling and which can be used in the present methods, is the U.S. Federal Bureau of Investigation's (FBI) Combined DNA Index System (CODIS). The CODIS is a collection of thirteen loci identified from the human genome that contain short (or simple) tandem repeat (STR) core sequences. An STR may comprise dimeric, trimeric, tetrameric, pentameric and hexameric tandem repeats of nucleotides. See U.S. Pat. No. 5,843,647 (Simple Tandem Repeats).

The CODIS loci are known as D16S539 (SEQ ID NO. 1), D7S820 (SEQ ID NO. 2), D13S317 (SEQ ID NO. 3), D5S818 (SEQ ID NO. 4), CSF1PO (SEQ ID NO. 5), TPOX (SEQ ID NO. 6), TH01 (SEQ ID NO. 7), vWA (SEQ ID NO. 8), FGA (SEQ ID NO. 9), D21S11 (SEQ ID NO. 10), D8S1179 (SEQ ID NO. 11), D18S51 (SEQ ID NO. 12), and D3S1358 (SEQ ID NO. 13). SEQ ID NOs 1-13 are provided herein.

Other loci that are not included in the CODIS collection but which can be used according to the present disclosure include but are not limited to Penta D (SEQ ID NO. 14), Penta E (SEQ ID NO. 15), and Amelogenin (SEQ ID NOs. 16 and 17); and D2S1338 (SEQ ID NO. 18), D19S433 (SEQ ID NO. 19), ACTBP2SE33 (SEQ ID NO. 20), D10S1248 (SEQ ID NO. 21), D1S1656 (SEQ ID NO. 22), D22S1045 (SEQ ID NO. 23), D2S441 (SEQ ID NO. 24), and D12S391 (SEQ ID NO. 25).

Commercially available kits that are sold for DNA profiling analyses provide PCR amplification primers that are designed to amplify all CODIS and some non-CODIS loci. Promega Corporation's PowerPlex® 16 DNA profiling series is an example of a commercially available collection of primers for amplifying sixteen loci identified as Penta E, D18S51, D21S11, TH01, D3S1358, FGA, TPDX, D8S1179, vWA, Amelogenin, Penta D, CSF1PO, D16S539, D7S820, D13S317 and D5S818. The PowerPlex® 16 kit is particularly useful because it has been approved for forensic DNA profiling use by the European police network, INTERPOL, the European Network of Forensic Science Institutes (ENFSI), GITAD (Grupo Iberoamericano de Trabajo en Análisis de DNA) and the United States Federal Bureau of Investigation (FBI).

In a particular embodiment in which tissue identification of either semen or non-semen, the methylation-sensitive restriction endonuclease is HhaI, the restriction loci are SD1, SD2, SD3, and SD4, a digested control locus is SD5, and an undigested control locus is SD6. These loci can be amplified using the following illustrative primer pairs:

```
                                           (SEQ ID NO: 68)
SD1 (forward AAGAGCCCATCAGGCAGGTC (FAM);
                                           (SEQ ID NO: 69)
     reverse GTTTCTTGTCGAGCAGCACGTGGATGATG);

(SEQ ID NO: 70)
SD2 (forward CTCCAGAACTGGAACTTCCTG (FAM);
                                           (SEQ ID NO: 71)
     reverse GTTTCTTAACTTGGAGACGACGGCATC);

(SEQ ID NO: 72)
SD3 (forward TGGAGGACAATGCCCTGGTG (FAM);
                                           (SEQ ID NO: 73)
     reverse GTTTCTTGGCTTCACCTGCGACCGTCTC);

(SEQ ID NO: 74)
SD4 (forward CCCTCCGAGTGGCCAGCAG (FAM);
                                           (SEQ ID NO: 75)
     reverse GTTTCTGACCACTGCCGTGGGAATG);

(SEQ ID NO: 76)
SD5 (forward CTTCTCAGCCAATGGGAAGAG (FAM);
                                           (SEQ ID NO: 77)
     reverse ACGTAGAAGGACCCGAGGAC);

(SEQ ID NO: 78)
SD6 (forward TACAGACAAATCACTCAGCAGC (FAM);
                                           (SEQ ID NO: 79)
     reverse GTTTCTTGTCTGACACTCGGTTGTAGGTATT).
```

The nucleotide sequences for these six chromosomal loci (SD1-SD6) are provided elsewhere herein.

In a particular embodiment in which tissue identification is according to blood, saliva, semen, or skin epidermis, the methylation-sensitive restriction endonuclease is HhaI and the restriction loci selected from the group consisting of L91762, L68346, L50468, L14432, L4648, L39664, L30139, L55429, L62086, L76138, L15952, L36599, L26688, L81528, L36556, L16264. The nucleotide sequences for these loci are set forth elsewhere herein. The present invention is not limited to these particular loci.

In a particular embodiment in which tissue identification is performed together with DNA profiling, and is according to semen or non-semen, the methylation-sensitive restriction endonuclease is HhaI, and the restriction loci are L68346 and L16264.

In one embodiment, a pair of loci are selected from loci with known methylation levels in at least two DNA categories, such that one of the loci in the pair is known to have a higher methylation level than the second locus in that pair in one DNA category but not in the other.

As explained in more detail below, the present disclosure encompasses the use of a kit, such as the PowerPlex® 16 profiling kit, in conjunction with one or more primers for amplifying additional loci that are not contained within the kit. As a non-limiting example, these additional locus may be selected because they are known to be differentially methylated in various tissues/cell types. Examples of such additional loci include but are not limited to SEQ ID NOs. 26-31. Thus, in accordance with the methylation ratio assay described herein, the ordinarily skilled person will expect a methylation-sensitive enzyme, such as HhaI, to properly bind and cut the unmethylated HhaI restriction site in these loci.

In another aspect of the present disclosure, prior knowledge of the sequence or methylation characteristics of a particular locus or pair of loci is not a prerequisite to performing an assay described herein. That is, an assay of the present disclosure encompasses the random selection of loci and the subsequent comparison of paired random loci amplified from a restriction-digested DNA sample to yield ratios that can be compared against control or threshold ratio values indicative of, for instance, the tissue/cell type source of the DNA sample.

Another aspect of the present invention is a kit for identifying the source of a DNA sample as semen or non-semen and for obtaining an associated confidence level, comprising:

(a) primer mix, comprising the following primers:

```
                                            (SEQ ID NO: 68)
SD1f (AAGAGCCCATCAGGCAGGTC);

(SEQ ID NO: 69)
SD1r (GTTTCTTGTCGAGCAGCACGTGGATGATG);

(SEQ ID NO: 70)
SD2f (CTCCAGAACTGGAACTTCCTG);

(SEQ ID NO: 71)
SD2r (GTTTCTTAACTTGGAGACGACGGCATC);

(SEQ ID NO: 72)
SD3f (TGGAGGACAATGCCCTGGTG);

(SEQ ID NO: 73)
SD3r (GTTTCTTGGCTTCACCTGCGACCGTCTC);

(SEQ ID NO: 74)
SD4f (CCCTCCGAGTGGCCAGCAG);

(SEQ ID NO: 75)
SD4r (GTTTCTGACCACTGCCGTGGGAATG);

(SEQ ID NO: 76)
SD5f (CTTCTCAGCCAATGGGAAGAG);

(SEQ ID NO: 77)
SD5r (ACGTAGAAGGACCCGAGGAC);

(SEQ ID NO: 78)
SD6f (TACAGACAAATCACTCAGCAGC);

and (SEQ ID NO: 79)
SD6r (GTTTCTTGTCTGACACTCGGTTGTAGGTATT);
```

(b) reaction buffer;
(c) HhaI restriction endonuclease;
(d) DNA polymerase
(e) a written protocol for performing tissue identification.

In another aspect of the present invention is a kit for tissue identification of a DNA sample as semen or non-semen and for obtaining an associated confidence level, comprising at least one pair of forward (f) and reverse (r) primer pair combinations selected from the group consisting of:

```
                                            (SEQ ID NO: 68)
(1)  SD1f (AAGAGCCCATCAGGCAGGTC)
     and
                                            (SEQ ID NO: 69)
     SD1r (GTTTCTTGTCGAGCAGCACGTGGATGATG);

(SEQ ID NO: 70)
(2)  SD2f (CTCCAGAACTGGAACTTCCTG)
     and
                                            (SEQ ID NO: 71)
     SD2r (GTTTCTTAACTTGGAGACGACGGCATC);

(SEQ ID NO: 72)
(3)  SD3f (TGGAGGACAATGCCCTGGTG)
     and
                                            (SEQ ID NO: 73)
     SD3r (GTTTCTTGGCTTCACCTGCGACCGTCTC);

(SEQ ID NO: 74)
(4)  SD4f (CCCTCCGAGTGGCCAGCAG)
     and
                                            (SEQ ID NO: 75)
     SD4r (GTTTCTGACCACTGCCGTGGGAATG);

(SEQ ID NO: 76)
(5)  SD5f (CTTCTCAGCCAATGGGAAGAG)
     and
                                            (SEQ ID NO: 77)
     SD5r (ACGTAGAAGGACCCGAGGAC);

(SEQ ID NO: 78)
(6)  SD6f (TACAGACAAATCACTCAGCAGC)
     and
                                            (SEQ ID NO: 79)
     SD6r (GTTTCTTGTCTGACACTCGGTTGTAGGTATT).
```

In one embodiment, the concentration of the primers in the primer mix are: 0.6 µM SD1f, 0.6 µM SD1r, 1.75 µM SD2f, 1.75 µM SD2r, 1.25 µM SD3f, 1.25 µM SD3r, 1.75 µM SD4f, 1.75 µM SD4r, 1.75 µM SD5f, 1.75 µM SD5r, 0.9 µM SD6f, and 0.9 µM SD6r.

In one embodiment, the reaction buffer comprises 150 mM TRIS-HCl, 15 mM MgCl2, 0.2 mM each dntp, and 0.1 µg/µl BSA.

In one embodiment, the kit further comprises a DNA ladder.

In one embodiment, the kit further comprises analysis software for performing tissue identification analyses.

Another aspect of the present invention is a kit for profiling, tissue identification of a DNA sample as semen or non-semen, and obtaining an associated confidence level, comprising:

(a) primers for amplifying at least one semen-specific locus;
(b) primers for amplifying at least one locus used for DNA profiling;
(c) reaction buffer;
(d) HhaI restriction endonuclease, (e) DNA polymerase (f) a written protocol for performing tissue identification.

In one embodiment, the kit further comprises control DNA samples.

Another aspect of the present invention is a kit for profiling, tissue identification of a DNA sample as semen or non-semen, and obtaining an associated confidence level, comprising:

(a) primers for amplifying at least one semen-specific locus; and (b) primers for amplifying at least one locus used for DNA profiling.

In one embodiment, at least one semen-specific locus amplified by a kit disclosed herein is the L68346 locus. In one embodiment, the primers for amplifying a 70 bp semen-specific amplification product from L68346 are a forward primer comprising the sequence of CAGCAACAGCAC-CCAGCTTG (FAM) (SEQ ID NO: 80) and a reverse primer comprising the sequence of CACAGGCTCAGTCGCG-GATC (SEQ ID NO: 81).

In one embodiment, at least one semen-specific locus amplified by a kit disclosed herein is the L16264 locus. In one embodiment, the primers for amplifying a 95 bp semen-specific amplification product from L16264 are a forward primer comprising the sequence of GGACGAGTTAACT-TCCTTAATTTC (FAM) (SEQ ID NO: 82) and reverse primer comprising the sequence of GTTTCTTCGCG-GAACCTGGTTTAACTTC (SEQ ID NO: 83).

In another embodiment, the reaction buffer comprises 150 mM TRIS-HCl, 15 mM MgCl2, 0.2 mM each dntp, and 0.1 µg/µl BSA.

In another embodiment, the kit further comprises at least one of (a) a DNA ladder, (b) a Material Safety Data Sheet (MSDS), and (c) analysis software for performing tissue identification analyses.

Another aspect of the present invention is a kit for tissue identification of a DNA sample as blood, saliva, semen, or skin epidermis, and for obtaining an associated confidence level, comprising:

(a) primer mix that comprises forward and reverse primers for amplifying the denoted loci as follows:

```
                                        (SEQ ID NO: 84)
1.  L91762 (forward GCAGCAGGCCGCGGAGAAG (FAM);
                                        (SEQ ID NO: 85)
            reverse AGCAGCTGTGCCGGGCCAG)

(SEQ ID NO: 80)
2.  L68346 (forward CAGCAACAGCACCCAGCTTG (JOE);
                                        (SEQ ID NO: 81)
            reverse CACAGGCTCAGTCGCGGATC)

(SEQ ID NO: 86)
3.  L50468 (forward AGGAAACCTCAGTAGCAAAATTG
            (JOE);
                                        (SEQ ID NO: 87)
            reverse GCGAGACTTTAGGTGTGCATC)

(SEQ ID NO: 88)
4.  L14432 (forward CGTAGGCTGCGGTGAGCTC (FAM);
                                        (SEQ ID NO: 89)
            reverse GATCCATGCCCGCTGGGATG)

(SEQ ID NO: 90)
5.  L4648  (forward CAGCCTAGACGTCAAGTTACAG (JOE);
                                        (SEQ ID NO: 91)
            reverse ACGACCTCCGGATCCAACTG)

(SEQ ID NO: 92)
6.  L39664 (forward CCCAGCTGGTTGGACATGTTG (FAM);
                                        (SEQ ID NO: 93)
            reverse CACTTCCTTCGTGGACGCC)

(SEQ ID NO: 94)
7.  L30139 (forward GAGAAGCGGGAGGATGAGAC (FAM);
                                        (SEQ ID NO: 95)
            reverse CCGCATCTCCTCCGTCCTG)

(SEQ ID NO: 96)
8.  L55429 (forward GCCTTCAGCAGGAAGTCCAC (JOE);
                                        (SEQ ID NO: 97)
            reverse CCTGTGCCTCACACAGACTC)

(SEQ ID NO: 98)
9.  L62086 (forward GTGCATGGTGTCTGGTACTTC (FAM);
                                        (SEQ ID NO: 99)
            reverse GAAGCTCTCGTGGACTACTTG)

(SEQ ID NO: 100)
10. L76138 (forward CAGCCTGCTCTTCACTGCAG (JOE);
                                        (SEQ ID NO: 101)
            reverse AGAGGCCGATGAAGCCGTAG)

(SEQ ID NO: 102)
11. L15952 (forward CTCCCTGATTTACGACAAGTTC (FAM);
                                        (SEQ ID NO: 103)
            reverse GACAGTATGCTGATGCTTCTTG)

(SEQ ID NO: 104)
12. L36599 (forward AAGGGCAGAGTTCCGCTGTC (FAM);
                                        (SEQ ID NO: 105)
            reverse CGGATGCAGGAGGATCCTAG)

(SEQ ID NO: 106)
13. L26688 (forward CGGACCAGATTGCTGGTCAC (JOE);
                                        (SEQ ID NO: 107)
            reverse CGACCTTGCCAGATGTTTGAC)

(SEQ ID NO: 108)
14. L81528 (forward AGCCTCATCCACACTGACCAG (JOE);
                                        (SEQ ID NO: 109)
            reverse TCAGAGCTCTCCTATCTGGAC)

(SEQ ID NO: 110)
15. L36556 (forward GCCAGGCCGTTGATGATGAC (JOE);
                                        (SEQ ID NO: 111)
            reverse GAATATGGAGCCCTGGGCAG)
```

(b) reaction buffer;

(c) HhaI restriction endonuclease;

(d) DNA polymerase (e) a written protocol for performing tissue identification.

In another embodiment, the kit further comprises control DNA samples.

In one embodiment, the reaction buffer comprises 150 mM TRIS-HCl, 15 mM MgCl2, 0.2 mM each dntp, and 0.1 µg/µl BSA.

In another embodiment, the kit further comprises at least one of (a) a DNA ladder, (b) a Material Safety Data Sheet (MSDS), and (c) analysis software for performing tissue identification analyses.

In one embodiment in any of the methods disclosed herein, the DNA sample comprises a mixture of DNA samples.

D. Combination of CODIS, Kits, and Methylation Assay

Accordingly, the combination of a CODIS or PowerPlex® 16 kit and the additional loci enables to simultaneously profile a DNA sample and determine the tissue/cell type source of the sample. For instance, the present methodology contemplates digesting a DNA sample with HhaI, and amplifying the DNA with the PowerPlex® 16's kit, to which primers for loci from SEQ ID NOs: 26-31 are added.

Analysis of loci SEQ ID NOs: 26-31, as described above, will yield the determination of the tissue/cell type source of the DNA sample, whereas the analysis of the profiling loci (e.g. PowerPlex 16 loci) will yield the determination of the DNA profile.

Thus, a powerful aspect of the present inventive technology is its ability to transform and expand the usefulness of existing commercial DNA profiling kits to do more than profile a particular subject's DNA. The combination of the inventive assays disclosed herein, such as the methylation ratio assay, with, for instance, the PowerPlex® 16 kit, enables the user to test the profiled DNA and determine the tissue/cell types source of the DNA.

(1). DNA Profiling Kits

Other examples of DNA profiling kits whose usefulness can be enhanced to determine also the tissue/cell type source of the DNA sample include but are not limited to SGM, SGM+, AmpFlSTR Identifier, AmpFlSTR Profiler, AmpFlSTR ProfilerPlus, AmpFlSTR ProfilerPlusID, AmpFlSTR SEfiler, AmpFlSTR SEfiler Plus, AmpFlSTR Cofiler, AmpFlSTR Identifier Direct, AmpFlSTR Identifier Plus, AmpFlSTR NGM, AmpFlSTR Y-filer, AmpFlSTR Minified, PowerPlex1.1, PowerPlex2.1, PowerPlex16, PowerPlexES, PowerPlexESX16, PowerPlexESI16, PowerPlexESX17, and PowerPlexESI17.

(2). Sequences

The sequences provided herein for the various CODIS, PowerPlex® 16, and other loci commonly used for profiling, i.e., SEQ ID NOs. 1-25, have been analyzed herein to determine (1) the position of every cytosine-guanine (CG) dinucleotide, (2) the methylation-sensitive and methylation-dependent restriction enzyme profile for that particular locus. The sequence listing included within the text of this application therefore provides guidance to the ordinarily skilled person in the identification of particular methylation-sensitive and methylation-dependent restriction endonucleases that can be used in accordance with ratio-generating assay methods.

The sequence information provided herein also permits the ordinarily skilled artisan to design forward and reverse amplification primers that anneal to regions of a selected locus that flank the CG and restriction site. Thus, the present disclosure is not limited to the amplification of, for instance, CODIS loci, using only those commercially available primers, although the use and availability of commercially available primers can be a more convenient and cost-effective option for performing the present authentication assays.

(3). Correction for "Ski-Slope" Effect

A common problem with some electropherogram trace outputs is an artifact known as a "ski slope." A "ski slope" is the name given to an artifact that is sometimes observed in electropherograms and which manifests in an inverse relationship between amplicon size and signal intensity. In such electropherograms, the signals resemble a "ski-slope" tail, the trace of which runs down and to the right. This artifact can be caused by several factors, for example by sample overload (too much DNA template in PCR) or from degraded DNA.

The present assays correct for this artifact in the calculation of methylation ratios by performing a normalization step. Typically, the normalization process entails (1) obtaining a linear fit for the sample from a subset of loci; (2) normalizing all peak values to the linear fit obtained in (1); and (3) calculating methylation ratios based on normalized peak values. Specific loci used for calculation of linear fit in PowerPlex® 16 were determined herein as D3S1358, TH01, D21S11, Penta_E.

Figure 4:
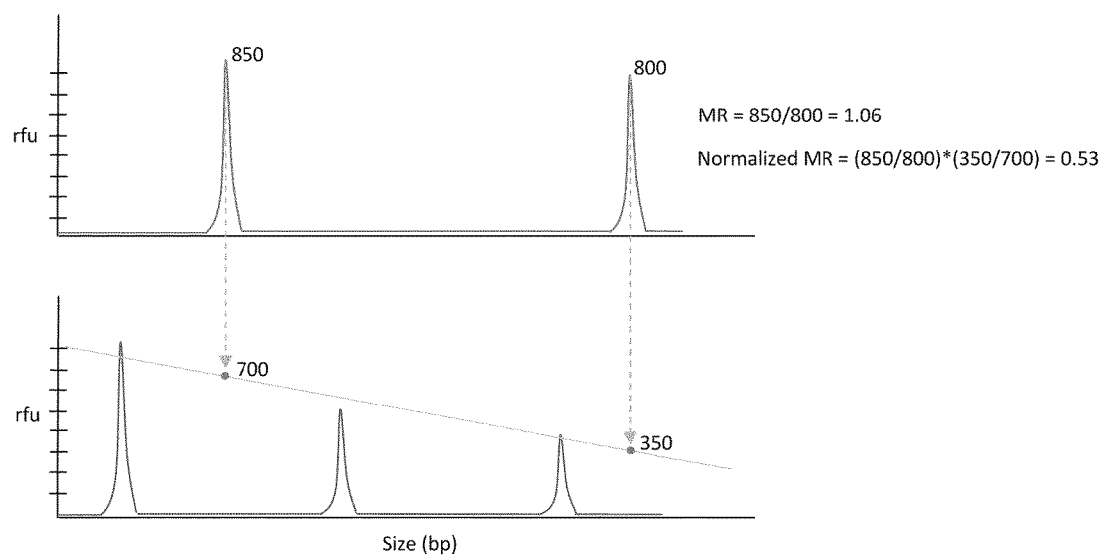
FIG. 4: Normalization of methylation ratios. The top and bottom panels represent two channels of a single electropherogram. Signals in the lower channel were used for obtaining a linear fit (grey line). For the two loci in the top panel, a non-normalized methylation ratio (MR) was calculated by dividing the respective rfus. A normalized methylation ratio was also calculated for the loci in the top panel by multiplying the non-normalized methylation ratio by the reciprocal of a corresponding ratio obtained from the loci's projections on the linear fit.
Figure 5:
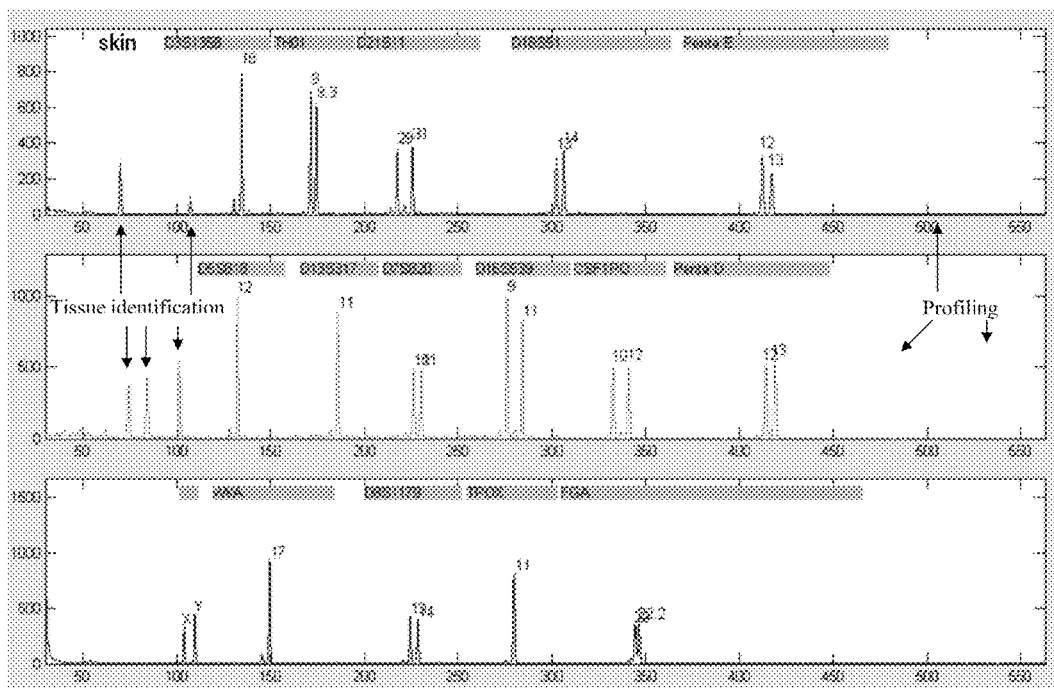
FIG. 5: Combined tissue identification and DNA profiling of a DNA sample from skin epidermis. Peaks corresponding to loci used for tissue identification are found in the range of <110 bps (top and middle panels), while other peaks correspond to loci used for DNA profiling.

A criterion for deciding which subset of loci are useful for calculating the linear fit is whether the loci are uninformative in relation with the tested character. Specifically, they should not contain the recognition sequence of the restriction enzyme used in the assay, or else should have similar methylation ratios in all relevant tissues. For example, for the PowerPlex16 kit it was found herein that this subset consists of the loci D3S1358, TH01, D21S11, Penta_E. Once the subset of loci is determined, the linear fit can be calculated, for example, by performing the least squares method on the relative fluorescent unit (rfu) signals of this particular subset of loci. Subsequent normalizing of a peak value can be achieved, for example, by dividing the rfu of the peak by the value of the linear fit at the same X-axis coordinate (size in bp). See, e.g., FIG. 4.

(4). Algorithm and Software

In one embodiment, calculation of methylation ratios is performed based on analysis of the intensities of signals of amplification products of fluorescent PCR that are run on a capillary electrophoresis machine. The output of the capillary electrophoresis machine is a binary computer file (for example, an FSA file in the case of capillary electrophoresis machines of Applied Biosystems). This file includes information regarding the capillary electrophoresis run, including the channel data, which is the relative fluorescent units (rfus) of each fluorophore as a function of each sampling time point (called datapoint).

The present disclosure also describes a software program that accepts as input a file that is the output a capillary electrophoresis machine run, and calculates the fluorescence intensities of a set of loci whose amplification products were run on the capillary electrophoresis machine. Based on these intensities, the software calculates methylation ratios, based on a set of predefined pairs of loci for which the ratios are defined to be calculated. Finally, the software outputs the tissues/cell type that is most likely the source of the DNA sample Following is a scheme of this analysis performed by the software program:

1. Read the channel data of each fluorophore. This requires knowledge of the specific format in which the channel data is encoded in the capillary electrophoresis output file. In the case of FSA files, the format is explained in detail in a document written by Applied Biosystems (which is available online at www.appliedbiosystems.com/support/software_community/ABIF_File_Format.pdf), enabling a person skilled in the art to write a computer program to obtain the channel data (and other information regarding the run) from this file.

2. Perform baseline reduction for the channel data of each fluorophore. Each fluorophore has a basal fluorescent intensity level, meaning that even when no amplification products labeled by that fluorophore are detected at a certain datapoint, the rfu level of that fluorophore will be non-zero at that datapoint. In order to perform correct analysis, the baseline level of each fluorophore needs to be removed by reducing the baseline level from the rfu level at all timepoints. The baseline level of each fluorophore can be obtained, for example, by averaging the rfu level of that fluorophore in parts of the run in which there were no amplification products for that fluorophore. Because normally most of the capillary electrophoresis run is devoid of amplification products, finding such regions is not a difficult task for a person skilled in the art.

3. Remove spectral overlap between fluorophores. The fluorescent dyes used in capillary electrophoresis have distinct maximum emission lengths, but nevertheless they have overlapping emission spectra. This means that certain dyes "pull-up" other dyes, creating artifact rfu levels in the other dyes. In order to perform correct analysis, these pull-ups need to be removed. This can be performed by knowing the n*n matrix of pull-ups (where n is the number of dyes), in which the (i,j) element is the fraction by which dye i pulls-up dye j. This matrix can be obtained by running on the dye set the spectral calibration procedure on the capillary electrophoresis machine.

4. Detect peaks. Certain parts of the channel data are peaks signals, each corresponding to a specific amplification product. An amplification product can correspond for example to an allele of a profiling locus, a control locus, or a peak in the standard curve. Peaks in capillary electrophoresis data have distinct patterns that enable to detect them, and a person skilled in the art knows this distinct pattern. Based on this, an algorithm for peak detection can be designed. One example for such a peak detection algorithm is as follows: detect all local maxima (i.e. datapoints at which the rfu level is greater than the rfu level of both two neighboring datapoints) and define each such local maxima as peaks with a height equal to the rfu level at the local maxima point. Because not all local maxima correspond to peaks, excessive peaks need to be removed. One way to remove excessive peaks is, for example, based on the idea that a peak must have the highest rfu level in its close vicinity (within its X neighboring datapoints). Based on this, excessive peaks are removed by going over all peaks, and removing any peak that is close (within X datapoints, where X is some pre-defined parameter) to another higher peak.

5. Assign sizes in basepairs to peaks. Channel data for each fluorophore is obtained as a set of rfu levels as a function of datapoints. Datapoints correlate to basepairs, but the exact function correlating between the two needs to be determined. For this purpose, a standard curve—a set of amplification products with known lengths in basepairs—is run together with the sample amplification products (whose lengths are unknown). Based on the standard curve peaks, a fit correlating datapoints and basepairs is obtained. This fit can be obtained using one of several methods known in the art, for example using the Least Squares method. Once a fit is obtained, all detect peaks are assigned their sizes in basepairs.

6. Obtain the signal intensities of the loci used for analysis. The expected size of each analyzed locus is known a priori. Loci can be polymorphic (e.g. as used for profiling), and in this case their expected size is within a certain range based on the set of possible alleles of that locus. Other loci are non-polymorphic (e.g. control loci), in which case their expected size is within a smaller range. The signal intensity of each locus is the sum of rfus of non-artifact peaks within the range of the locus (e.g. the two peaks corresponding to the two alleles of a profiling locus).

7. Obtain the methylation ratios. Once signal intensities are calculated for all loci, a methylation ratio between a pair of loci is the division of the signal intensity of the first locus in the pair by the signal intensity of the second locus in the pair.

8. Calculate probability and combined probability scores. Probability scores can be calculated based by comparing methylation ratios to reference distributions of methylation ratios obtained from different tissues/cell types. Combined Probability Scores (CPS) of each tissue/cell type can then be calculated from the single probability scores, for example by calculating the n-th root of the product of the single probability scores (where n is the number of methylation ratios).

9. Calculate likelihood scores. For each tissue/cell type, calculate a Likelihood Score (LS), that represents the likelihood that the DNA sample originated from that tissue/cell type. Likelihood scores for each tissue/cell type can be calculated for example as follows:

LS(tissue)=CPS(tissue)/[sum of CPSs of all tissues]

10. Output the tissue/cell type with the highest LS.

(5). Determining the Source of a Mixed DNA Sample

In some cases, the DNA sample is not of pure source, but rather is a mixture of two or more source (e.g. 50% blood and 50% semen). The present invention can also determine the makeup of source of such a sample by performing the following analysis:

(a) digesting the DNA sample with a methylation-sensitive and/or methylation-dependent restriction endonuclease;

(b) amplifying the digested DNA with at least a first and a second restriction locus, thereby generating an amplification product for each restriction locus;

(c) determining the intensity of the signal of each amplification product;

(d) calculating at least one methylation ratio between the intensity of the signals corresponding to the two restriction loci;

(e) comparing the methylation ratio calculated in step (d) to a set of reference methylation ratios obtained from DNA of known tissues and/or cell types;

(f) determining the likelihood of each tissue and/or cell type contributing to the source of DNA; and (g) determining the composition of the source DNA based on the likelihoods obtained in step (f)

EXAMPLES

Example 1: Tissue Identifier Assay Based on Genomic Loci

In this example a tissue identifier assay was developed that is capable of distinguishing between DNA samples obtained from blood, semen, and skin epidermis. The assay is based on the analysis of six specific genomic loci, each set forth in SEQ ID NOs: 26-31. Each locus is a fragment sized 70-105 bp containing a HhaI restriction site (GCGC). The enzyme HhaI cleaves its recognition sequence only if it is unmethylated, therefore the assay is based on differences in methylation in the recognition sequences only. The six genomic loci each contain additional CGs whose methylation status is of no consequence to the assay—only the methylation of the recognition sequence is relevant. The sequences of the six genomic loci are:

SEQ ID NO: 26 (Chr. 3):
CAGCAACAGCACCCAGCTTGGCGCGGGCCGAGGGCTCCCAGGCATGACAC

TGCA<u>GATCCGCGACTGAGCCTGTG</u>

SEQ ID NO: 27 (Chr. 10):
<u>TTAAGTAATGTCAAGAAGGCAAT</u>GCGCTGAGACTGGAGAGCAGAAGAAAG

CATCACTGGG<u>CTAACACAGCAAATGTGGAACC</u>

SEQ ID NO: 28 (Chr. 1):
CAGCCTAGACGTCAAGTTACAGCCCGCGCAGCAGCAGCAAAGGGGAAGGG

GCAGGAGCCGGGCA<u>CAGTTGGATCCGGAGGTCGT</u>

SEQ ID NO: 29 (Chr. 5):
<u>GCCTTCAGCAGGAAGTCCAC</u>AACCCTGCAAAAGAGGGCGCTGCGTCACGC

GGGCACACGTCCGCAGTCTCG<u>GAGTCTGTGTGAGGCACAGG</u>

-continued

SEQ ID NO: 30 (Chr. 3):
CTTCTCCGAGGTCGCAGGTGGAACGGGCTTGCGCGTGAGAACGGGGCCTG

GGCTTAACTCACTGGGGCCTCCCCCGGGTGGCCGAGGTTCTTTTCCCACG

CCC

SEQ ID NO: 31 (Chr. 22):
CAGCATCCATCCCATGGTATGGGTGGGAAGCCTGAGGCTTGGGCTGGTCA

AGGGACCTGCGCCAGGTCATGCAGATGAACAGCAGGGGAGCCCAAGTTTA

AACCCGG

Primer sequences are underlined, HhaI recognition sequences are bolded.

Figure 6:
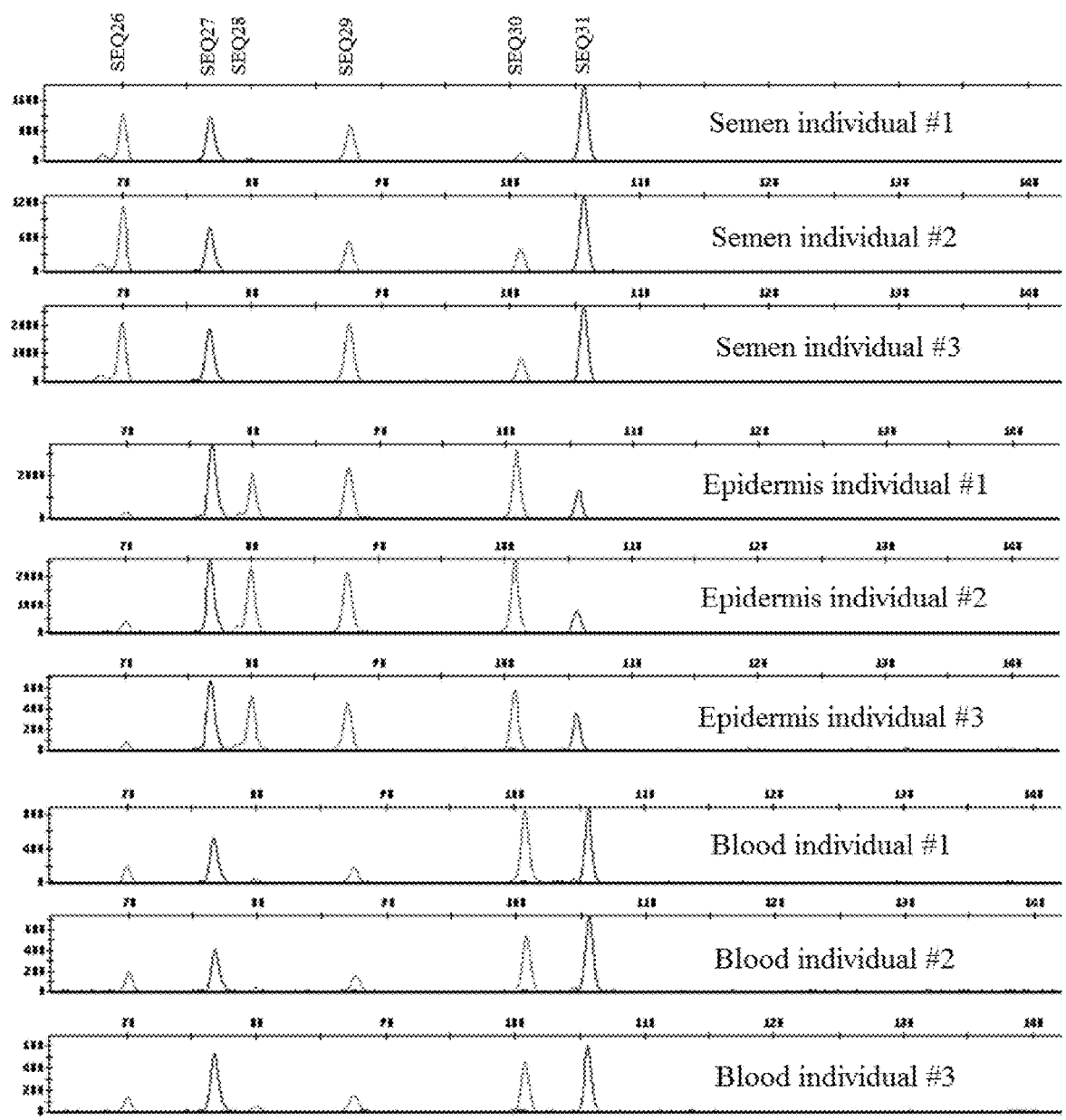
FIG. 6: Electropherograms of capillary electrophoresis of nine DNA samples extracted from semen, blood, and epidermis from three individuals. Differential methylation in semen, blood, and epidermis is evidenced by the different intensities of the analyzed loci.

The assay was performed on DNA samples extracted from semen, epidermis and blood of three different individuals (total of nine samples). One nanogram of each DNA sample was mixed with HhaI, Taq Polymerase, forward (fluorescently-labeled) and reverse primers for the six loci SEQ ID NOs: 26-31, dNTPs, and reaction buffer in a single microcentrifuge tube. The tube was then placed in a thermocycler and subject to a single program that contains an initial digestion step (37° C.), followed by PCR amplification of digestion products. Following the restriction-amplification reaction, an aliquot of the products was run on a capillary electrophoresis machine. FIG. 6 shows the electropherograms of capillary electrophoresis of the nine samples. In each electropherograms, there are six peaks, each corresponding to one locus. The data from the electropherograms of the nine samples was then analyzed as follows: for each sample, the intensity of the signal (rfu) in each locus was quantified, and methylation ratios (e.g. rfu of locus 1 divided by rfu of locus 2) were calculated for all 15 loci pair combinations (e.g. SEQ ID NO: 26/SEQ ID NO: 28). Table 1 shows values of two of the fifteen such methylation ratios (SEQ ID NO: 29/SEQ ID NO: 30 and SEQ ID NO: 28/SEQ ID NO: 26) for all samples. For each sample, each methylation ratio was compared to the cumulative distribution functions of its reference distributions in blood, semen and epidermis (obtained empirically from a large set of DNA samples from blood, semen, and epidermis)

TABLE 1

Methylation ratios for two pairs of loci in the nine analyzed samples.

|  | SEQ29/SEQ30 | SEQ28/SEQ26 |
|---|---|---|
| Semen individual #1 | 4.01 | 0.04 |
| Semen individual #2 | 1.27 | 0.02 |
| Semen individual #3 | 2.54 | 0 |
| Epidermis individual #1 | 0.76 | 6.68 |
| Epidermis individual #2 | 0.81 | 5.38 |
| Epidermis individual #3 | 0.76 | 6.41 |
| Blood individual #1 | 0.21 | 0.18 |
| Blood individual #2 | 0.30 | 0.25 |
| Blood individual #3 | 0.33 | 0.42 |

Table 2 shows means and standard deviations of reference distributions for two methylation ratios (obtained empirically from a large set of DNA samples from blood, semen, and epidermis).

TABLE 2

Reference methylation ratio values for two pairs of loci (mean ± std)

|  | SEQ29/SEQ30 | SEQ28/SEQ26 |
|---|---|---|
| Semen | 2.8 ± 1.1 | 0.02 ± 0.04 |
| Epidermis | 0.78 ± 0.06 | 6.21 ± 0.7 |
| Blood | 0.29 ± 0.04 | 0.28 ± 0.08 |

For each tissue/cell type, each comparison between the observed methylation ratio and its corresponding value in the cumulative distribution function yielded a Probability Score, calculated as follows:

PS(Blood,SEQ26/28)=1−[2*abs($f$(OMR)−0.5)], where f is the cumulative distribution function of the reference distribution of SEQ26/28 in blood, and OMR is the observed methylation ratio of SEQ26/28 in the sample. PS(Semen, SEQ26/28) and PS(Epidermis, SEQ26/28) were calculated in a similar manner.

Next, Combined Probability Scores (CPS) were calculated for each tissue type based on all methylation ratios as follows:

CPS(Blood)=$n$th root of [LS(Blood,methylation ratio #1)*LS(Blood,methylation ratio #2)* ... *LS(Blood,methylation ratio #$n$)], where n is the number of methylation ratios CPS(Semen) and CPS(Epidermis) were calculated in a similar manner.

Finally, Likelihood Scores (LS) were calculated from the combined probability scores as follows:

LS(Blood)=CPS(Blood)/[CPS(Blood)+CPS(Semen)+CPS(Epidermis)]

LS(Semen) and LS(Epidermis) were calculated in a similar manner.

The likelihood score of each tissue/cell type represents the likelihood that the DNA sample originated from that specific tissue/cell type.

Table 3 shows likelihood scores for the three tissues based on all methylation ratios for all 9 DNA samples.

TABLE 3

Likelihood scores based on all methylation ratios

| | Combined likelihood scores based on all pairs of loci | | |
|---|---|---|---|
| | Semen | Epidermis | Blood |
| Semen individual #1 | >0.9999 | <0.0001 | <0.0001 |
| Semen individual #2 | >0.9998 | <0.0001 | <0.0001 |
| Semen individual #3 | >0.9999 | <0.0001 | <0.0001 |
| Epidermis individual #1 | <0.0001 | >0.9999 | <0.0001 |
| Epidermis individual #2 | <0.0001 | >0.9998 | <0.0001 |
| Epidermis individual #3 | <0.0001 | >0.9998 | <0.0001 |
| Blood individual #1 | <0.0001 | <0.0001 | >0.9999 |
| Blood individual #2 | <0.0001 | <0.0001 | >0.9999 |
| Blood individual #3 | <0.0001 | <0.0001 | >0.9999 |

Figure 7:
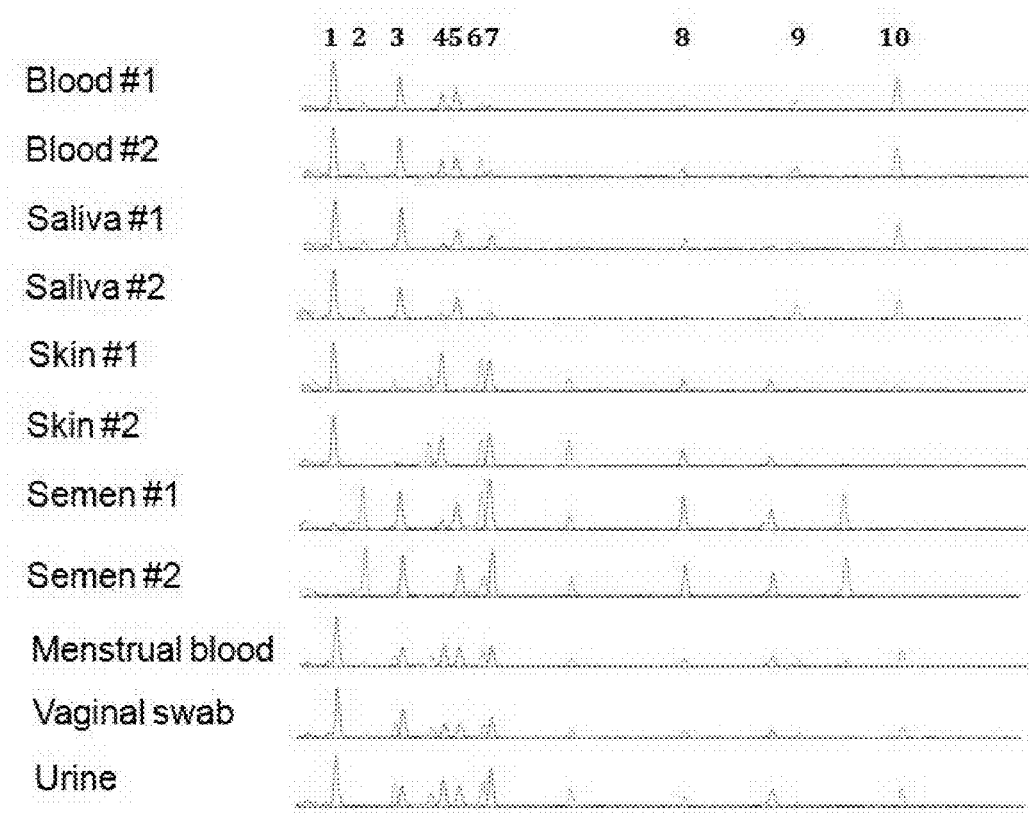
FIG. 7: Electropherograms of capillary electrophoresis of eleven DNA samples extracted from blood, saliva, skin, semen, menstrual blood, vaginal tissue, and urine. Differential methylation in blood, saliva, skin, semen, menstrual blood, vaginal tissue, and urine is evidenced by the different intensities of the analyzed loci.

Similarly, and as shown in FIG. 7, a tissue identification assay was performed using a 10-loci multiplex on 11 different DNA samples from blood, saliva, skin, semen, menstrual blood, vaginal swab, and urine. Analysis was based on 45 methylation ratios (e.g. locus 1/locus 2, locus 1/locus 3, etc.). Differential methylation across blood, saliva, skin, semen, menstrual blood, vaginal tissue, and urine is evidenced by the different intensities of the analyzed loci. The assay correctly identified the source tissue of all samples. For example, and as shown in FIG. 7, DNA derived from menstrual blood can be differentiated from DNA derived from saliva.

Example 2

Stand Alone Semen Detector Kit

The assay employed by the kit accepts as input a DNA sample which then undergoes a biochemical procedure followed by signal analysis by a dedicated software. The output of the assay is the source tissue of the DNA sample (semen or non-semen), and a statistical confidence level representing the likelihood that the outputted source tissue is the true source tissue of the DNA sample.

A semen detection kit of the present invention may comprise one or more of the following components:

1. A box that may comprise one or more of the following components:

Tube 1 comprising a 5× primer mix of:

```
                                              (SEQ ID NO: 68)
0.6 µM    SD1f  (AAGAGCCCATCAGGCAGGTC);

(SEQ ID NO: 69)
0.6 µM    SD1r  (GTTTCTTGTCGAGCAGCACGTGGATGATG);

(SEQ ID NO: 70)
1.75 µM   SD2f  (CTCCAGAACTGGAACTTCCTG);

(SEQ ID NO: 71)
1.75 µM   SD2r  (GTTTCTTAACTTGGAGACGACGGCATC);

(SEQ ID NO: 72)
1.25 µM   SD3f  (TGGAGGACAATGCCCTGGTG);

(SEQ ID NO: 73)
1.25 µM   SD3r  (GTTTCTTGGCTTCACCTGCGACCGTCTC);

(SEQ ID NO: 74)
1.75 µM   SD4f  (CCCTCCGAGTGGCCAGCAG);

(SEQ ID NO: 75)
1.75 µM   SD4r  (GTTTCTGACCACTGCCGTGGGAATG);

(SEQ ID NO: 76)
1.75 µM   SD5f  (CTTCTCAGCCAATGGGAAGAG);

(SEQ ID NO: 77)
1.75 µM   SD5r  (ACGTAGAAGGACCCGAGGAC);

(SEQ ID NO: 78)
0.9 µM    SD6f  (TACAGACAAATCACTCAGCAGC);
          and (SEQ ID NO: 79)
0.9 µM    SD6r  (GTTTCTTGTCTGACACTCGGTTGTAGGTATT)
```

The forward primers (e.g., SD_f) are fluorescently labeled;

Tube 2 comprising a 10× reaction buffer (150 mM TRIS-HCl, 15 mM MgCl$_2$, 0.2 mM each dntp, 2.5 µg BSA);
Tube 3 comprising HhaI restriction endonuclease;
Tube 4 comprising a control semen DNA sample;
Tube 5 comprising a control non-semen DNA sample;
Tube 6 comprising a DNA ladder; and
a Material Safety Data Sheet (MSDS).

2. A paper detailing the following protocol, or similar instructions:

(a) For each reaction, combine in a 0.2 ml tube (not provided) the following ingredients: 5 µl 5× primer mix, 2.5 µl 10× reaction mix, 0.5 µl HhaI endonuclease, 0.5 µl DNA polymerase, 0.5 ng DNA, and DDW (distilled water) to a total volume of 25 µl.

(b) In addition to the tested DNA, set up a positive control semen reaction using the supplied semen DNA, a positive control non-semen reaction using the supplied blood DNA, a negative control reaction using DDW instead of DNA, and a digestion control reaction using DDW instead of HhaI.

(c) Place the reaction tubes in the thermal cycler and run the following program: 37° C. for 15 min, 95° C. for 11 min, followed by 30 cycles of 94° C. for 1 min, 59° C. for 1 min, 72° C. for 1 min, followed by a final extension step of 60° C. for 45 min, and hold at 25° C.

(d) For each post-amplification reaction, mix 1.5 µl product with 24.5 µl formamide and 0.5 µl fluorescent size standard in a new 0.2 ml tube.

(e) Denature samples at 95° C. for 3 minutes, then immediately chill on ice for 3 minutes.

(f) Run denatured samples in the capillary electrophoresis machine using the following parameters:
Module=GS STR POP4 (1 mL) F;
Inj. secs=5;
Inj. kV=15;
Run kV=15;
Run C=60;
Run time=24 min (g) Analyze output .fsa files in the TissueIdentifier analysis software.

3. "Tissue Identifier" analysis software implementing the tissue identification algorithm as described in the "Algorithm and Software" section above, with the following modifications:

In step 3 of the algorithm, the set of pairs of loci used are: {SD1,SD6}, {SD2,SD6}, {SD3,SD6}, {SD4,SD6}, and {SD5,SD6}.

A correction for incomplete digestion was performed using the signal ratio of {SD5,SD6}. SD5 acted as a digested control locus and SD6 acted as an undigested control locus.

Reference probability functions of semen and non-semen were obtained for {SD1,SD6}, {SD2,SD6}, {SD3,SD6}, {SD4,SD6} using a set of 27 reference semen samples obtained from 27 different individuals and 86 reference non-semen samples (blood, saliva, urine, vaginal swab, menstrual blood) obtained from different individuals.

The assay is based on analysis of 6 genomic loci. Of these, 4 loci were found by the inventors to be differentially methylated in semen vs. non-semen tissues. Two of these four loci are methylated in all tissues except semen, and the two other loci are unmethylated in all tissues except semen. The assay also includes an undigested control locus that does not contain a HhaI recognition sequence (SD6) and is therefore expected to be amplified successfully regardless of the tissue type, and a digested control locus (SD5) which was found by the inventors to be unmethylated in all potential tissues.

This kit was tested on 27 semen and 86 non-semen (blood, saliva, urine, vaginal swab, menstrual blood) DNA samples from 95 different donors of different sexes, ages, and ethnicities. The algorithm correctly identified the source of all samples with a typical confidence level >99.999999%. The tested samples were the same samples used for obtaining reference probability functions. However, in order to avoid bias, in each specific analysis, the analyzed sample was not used for obtaining the reference probability functions.

Example 3

Combined Semen Detection and DNA Profiling

In this example tissue identification of the DNA is into one of two potential sources: semen and non-semen where non-semen refers to all tissues except semen. The tissue identification is performed together with DNA profiling in the same reaction.

The tissue identification procedure utilizes the same platforms used in standard STR profiling (i.e. thermocycler and capillary electrophoresis instruments) and is therefore readily amenable to integration with DNA profiling in a single reaction. This capability was demonstrated by generating an integrated STR profiling and semen detection assay. A STR profiling kit (Profiler Plus) PCR was supplemented with primers specific for two semen identification loci. These loci consist of a 70 bps amplicon which is efficiently amplified only in semen and a 95 bps amplicon which is efficiently amplified in all tissues except semen. The assay was tested on pure samples of semen, urine (male), venous blood, menstrual blood, vaginal secretion, and saliva. The correct pattern of semen identification amplification was observed and the tissue identification algorithm correctly identified presence/absence of semen in all samples.

Complete electropherograms of semen and urine samples were obtained from the same individual, as well as FAM channel data from all samples including the two semen identification loci and three profiling loci. The observed signal ratio was 25.04 in the semen sample, and 0.04-0.089 in the other samples. The combined assay was also tested on mixtures of semen and saliva at various ratios. For each of these mixtures the percentage of the semen in the sample was derived from the signal ratio of the semen identification loci and compared with the corresponding percentage derived from the profiling loci (the semen and saliva samples were obtained from different individuals and could therefore be differentiated based on STR loci). The percentages derived were comparable, with a maximum difference of 10%. Moreover, the presence vs. absence of semen was correctly determined in all samples including a sample that contained only 13% semen. The STR profiles obtained from the samples using the integrated profiling-semen detection assay were identical to profiles obtained from the same samples using ProfilerPlus (without semen detection).

What is claimed is:

1. A method for identifying the source of a mammalian DNA sample comprising:
   (a) applying the mammalian DNA sample to digestion with at least one methylation-sensitive or at least one methylation-dependent restriction endonuclease under conditions that allow complete DNA digestion, to obtain restriction enzyme-treated DNA;
   (b) co-amplifying at least two different genomic loci from the same digest of restriction enzyme-treated DNA in a single reaction mixture using at least two different locus-specific primer pairs, thereby generating a specific amplification product for each locus of said at least two different genomic loci, wherein at least one of the loci is a restriction locus comprising a recognition sequence of said methylation-sensitive or methylation-dependent restriction endonuclease, and wherein said co-amplifying comprises using fluorescent PCR;
   (c) determining a signal intensity of each amplification product in said single reaction mixture;
   (d) calculating a ratio between the signal intensities of amplification products of the at least two different genomic loci determined in step (c) in said single reaction mixture;
   (e) providing reference ratios between signal intensities of amplification products of said at least two different genomic loci in known reference tissues and/or cell types; and
   (f) calculating probability scores for said ratio with each of said reference ratios, wherein said probability scores reflect how close the ratio is to each reference ratio and accordingly the likelihood of each reference tissue or cell type being the source of the mammalian DNA sample, wherein the reference tissue or cell type with the highest probability score is determined to be the source of said DNA sample,
   wherein said at least two different genomic loci are chosen such that they produce distinct signal intensity ratios for specific tissues and/or cell types; and
   wherein DNA digestion and amplification in said DNA sample are performed in a single biochemical reaction in a single test tube.

2. The method of claim 1, wherein said source is a tissue or cell type.

3. The method of claim 1, wherein said single test tube comprises DNA template, digestion and amplification enzymes, buffer, primers designed to amplify said at least two different genomic loci, and accessory ingredients.

4. The method of claim 3, wherein said single test tube is closed and placed in a thermal cycler, where the single reaction takes place.

5. The method of claim 1, wherein said methylation-sensitive restriction endonuclease is selected from the group consisting of AatII, Acc65I, AccI, AciI, ACII, AfeI, AgeI, ApaI, ApaLI, AscI, AsiSI, AvaI, AvaII, BaeI, BanI, BbeI, BceAI, BcgI, BfuCI, BglI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinP1I, HpaI, HpaII, Hpy166ii, Hpy188iii, Hpy99I, HpyCH4IV, KasI, MluI, MmeI, MspA1I, MwoI, NaeI, NarI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI.

6. The method of claim 5, wherein said methylation-sensitive restriction endonuclease is HhaI.

7. The method of claim 1, wherein said methylation dependent restriction endonuclease is McrBC, McrA, or MrrA.

8. The method of claim 1, wherein said tissue and/or cell type is blood, saliva, semen, or epidermis.

9. The method of claim 1, wherein said mammalian DNA is DNA from a mammal selected from the group consisting of human, ape, monkey, rat, mouse, rabbit, cow, pig, sheep, and horse.

10. The method of claim 1, wherein said mammalian DNA is human DNA.

11. The method of claim 10, wherein the human DNA is from a male.

12. The method of claim 10, wherein the human DNA is from a female.

13. The method of claim 1, wherein said amplifying is performed using fluorescently labeled-primers.

14. The method of claim 13, wherein each signal intensity is determined by separating said amplification products by capillary electrophoresis and then quantifying fluorescence signals.

15. The method of claim 1, wherein signal intensity is determined by real-time PCR.

16. The method of claim 1, wherein said source is a specific physiological/pathological condition.

17. The method of claim 1, wherein said source is a specific age, or range of ages.

18. The method of claim 1, wherein said source is male.

19. The method of claim 1, wherein said source is female.

20. The method of claim 1, wherein the mammalian DNA sample is obtained from a forensic investigation, a medical treatment, a criminal or civil investigation, food quality review, agricultural control or combinations thereof.

21. The method of claim 1, wherein the at least two different genomic loci comprise (1) a plurality of restriction loci and (2) a locus lacking a recognition sequence of the methylation-sensitive or methylation-dependent restriction endonuclease, and wherein step (d) comprises calculating a plurality of ratios, between the signal intensity of the amplification product of the locus lacking said recognition sequence and the signal intensities of each restriction locus, and wherein step (f) comprises calculating a probability score for each of said plurality of ratios.

22. The method of claim 21, wherein step (d) further comprises calculating ratios between the signal intensity of the amplification product of each one of said plurality of restriction loci and the signal intensity of the amplification product of each of the remaining of said plurality of restriction loci.

23. The method of claim 1, wherein the at least one restriction locus is a plurality of restriction loci, and wherein step (d) comprises calculating a plurality of ratios, between the signal intensity of the amplification product of each one of said plurality of restriction loci and the signal intensity of the amplification product of each of the remaining of said plurality of restriction loci.

24. The method of claim 1, wherein no standard curve from control DNA is generated and wherein no actual methylation level at any genomic locus is indicated by said method.

25. The method of claim 5, wherein said methylation-sensitive restriction endonuclease is Hinp1I.

* * * * *

SEQUENCE LISTING

<160> NUMBER OF SEQ ID NOS: 111

<210> SEQ ID NO 1
<211> LENGTH: 889
<212> TYPE: DNA
<213> ORGANISM: Homo sapiens

<400> SEQUENCE: 1

```
ctcttctcat tccacaagct ctccccaaaa gacccccattc ctccccacct tcaaccatct      60
ctggcaggga ggaggggaa ctgagaggct actttctgac ccaggaccct aagcctgtgt     120
acggagagag catgagctgg gtgagctgct tgccaaggag tggcatctgc cctcatcagt     180
ggacacaaaa agccccaggg gttaagtggc catggctgcc ctcatggctg caccgggagg     240
atgactgtgt tcccactctc agtcctgccg aggtgcctga cagccctgca cccaggagct     300 gggggggtcta agagcttgta aaaagtgtac aagtgccaga tgctcgttgt gcacaaatct     360
aaatgcagaa aagcactgaa agaagaatcc agaaaaccac agttcccatt tttatatggg     420
agcaaacaaa ggcagatccc aagctcttcc tcttccctag atcaatacag acagacagac     480
aggtggatag atagatagat agatagatag atagatagat agatagatat cattgaaaga     540
caaaacagag atggatgata gatacatgct tacagatgca cacacaaacg ctaaatggta     600
taaaaatgga atcactctgt aggctgtttt accacctact ttactaaatt aatgagttat     660
tgagtataat ttaattttat atactaattt gaaactgtgt cattaggttt ttaagtctat     720
ggcatcactt tcgcttgtat ttttctattg atttctttc ttttcttttc ttttttgaga     780
cagagtctca ctctcaccca ggctggagta ccgtggcacg atcttggctc attgcaacca     840
ccacctcccg ggctcaagtg attatcctgc ctcagcctcc caaatagct                  889
```

<210> SEQ ID NO 2
<211> LENGTH: 843
<212> TYPE: DNA
<213> ORGANISM: Homo sapiens

<400> SEQUENCE: 2

```
atatgctaac tggatgtgaa caattgtgtt ctaatgagct taatatgagt ttcataattt      60
gtgcattttg ctgttaaaaa gccagaaaac aaaacaaaac aaaatactga aaccagtgtg     120
aacaagagtt acacgatgga aggcatcagt tttcacacca gaaggaataa aaacaggcaa     180
```

```
aaataccata agttgatcct caaaatatga ttgattttaa gcctatgag ataattgtga    240 ggtcttaaaa tctgaggtat caaaaactca gagggaatat atattcttaa gaattataac    300
gattccacat ttatcctcat tgacagaatt gcaccaaata ttggtaatta aatgtttact    360
atagactatt tagtgagatt aaaaaaaact atcaatctgt ctatctatct atctatctat    420
ctatctatct atctatctat ctatctatct atcgttagtt cgttctaaac tatgacaagt    480
gttctatcat acccttata tatattaacc ttaaaataac tccatagtca gcctgaccaa     540
catggtgaaa ccccgtctct aaaaaaaata caaaaattag ctggatgcag tagcacatgc    600
ctgtagtccc agctactcag gaggctgggg caggagaacc acttgaccca agaagcggag    660
gttgcagtga gccgagatcg caccactgca ctccagcctg ggtgacagag tgagactcca    720
tctcaagata aagaaataaa taaaaacaaa caaacaaaaa aattccatag ggggtcaggt    780
gcggtggctc atgcctgtaa tcccagcact ttgggaggcc gaagcaggtg gatcacttga    840
ggt                                                                   843

<210> SEQ ID NO 3
<211> LENGTH: 792
<212> TYPE: DNA
<213> ORGANISM: Homo sapiens

<400> SEQUENCE: 3
aatatgaatt caatgtatac agagagagag agagagagag agagagagag agacttctac     60
agagctctaa gcataattgt gtaactccaa gctcacagtg cctaagacca gtaccaggct    120
gactcattgg aaagctgcca tagtaagact cttctgttca ctgcattatt tattgatgta    180
ttgcaagcac ttagttacat ttctagcata taacacatga tcaataaata ttttgacatg    240
aacaaatggt aattctgcct acagccaatg tgaatattgg gatggttgc tggacatggt     300 atcacagaag tctgggatgt ggaggagagt tcatttcttt agtgggcatc cgtgactctc    360
tggactctga cccatctaac gcctatctgt atttacaaat acattatcta tctatctatc    420
tatctatcta tctatctatc tatctatcaa tcaatcatct atctatcttt ctgtctgtct    480 tttgggctg cctatggctc aacccaagtt gaaggaggag atttgaccaa caattcaagc     540
tctctgaata tgttttgaaa ataatgtata ttaatgaatg tacaaatttc cccacttgta    600 cttttcagact gttatctgtg agttaaaact cctccactct ttttcctacc caaataatag    660
catacttttt tctgagtata ttttgggaag aagagttatt cagttattgt tatattttaa    720
aaaattcctt ataccaaact ctacttgatc taaggctatt cattgaaact ttcagcatgc    780
ttaatagcag tc                                                         792

<210> SEQ ID NO 4
<211> LENGTH: 735
<212> TYPE: DNA
<213> ORGANISM: Homo sapiens

<400> SEQUENCE: 4
ccctctgtgt agcctggcta tgtgccacat tgtgaggttc tctccctcta gctacttctt     60
ccagtttcct ctttcaggat cccaattcct ttctcaaagc actggtgaat aactccaaat    120
actccatcat ttcattatac agagtaatat aagtcttctt tttctaaacc tctcccatct    180
ggatagtgga cctcatattt cagatgctaa taggctgttg aggtagtttc ctaagcaaaa    240
aagtaattgt ctctctcaga ggaatgcttt agtgcttttt agccaagtga ttccaatcat    300
```

```
agccacagtt tacaacattt gtatctttat ctgtatcctt atttatacct ctatctatct    360
atctatctat ctatctatct atctatctat ctatcttcaa aatattacat aaggatacca    420
aagaggaaaa tcacccttgt cacatacttg ctattaaaat atacttttat tagtacagat    480
tatctgggac accactttaa ttagaagctt taaaagcata tgcatgtctc agtatttaat    540
tttaaaatta ttacataatt atatactcct ttgaattaga aaattacaaa tgtggctatg    600
tattattttc tcccatgtat tttcaaaatg aggggtaag ccagaccctc tccctctccc     660
atgcctaata gctcaaagtt aaaggtaaag aaacaagaaa atatggtgaa agttaaccag    720
cttcacttca gagga                                                    735

<210> SEQ ID NO 5
<211> LENGTH: 949
<212> TYPE: DNA
<213> ORGANISM: Homo sapiens

<400> SEQUENCE: 5
attcaacaca tgaggcacgg ccagacctaa atgtctcaga gcctgctccc actccgatga     60
gctgctgcct tgcttcaggg tctgagtcca gtgactgcca ctgcctgcac ccaatcacca    120
tagccagaga cctggaggtc atccttatct cctttctctt cctcatccct gcatctcaga    180
ctcttccaca caccactggc catcttcagc ccattctcca gcctccaggt tcccacccaa    240
cccacatggt gccagactga gccttctcag atactatctc ctggtgcaca cttggacagc    300
atttcctgtg tcagaccctg ttctaagtac ttcctatcta tctatctatc tatctatcta    360
tctatctatc tatctatcta tctatcaat ctatctatct tctatctatg aaggcagtta    420
ctgttaatat cttcattta caggtaggaa aactgagaca cagggtggtt agcaacctgc    480
tagtccttgg cagactcagg ttggaacact gccctggagt gtgtgctcct gaccaccacg    540
aagtgcctcc tctgtacaat ctgaccccat cactctcctc tttacaatga cctcccaata    600
ggttaagatg cagttattct ttctcacttt aagacacctt tacctccggc ttctgccacc    660
tcctctgctc ccctgtggcc actcctcaca ccactccaca tcccagctgt tgtcaagttc    720
tttcagtgtt ccaaatgatc tatgttctct ttgcctttga gccttgcata tgttcctccc    780
tctgccagaa gcgctgttcc ccttcctttc ccacccttct gcccggccaa ctcaccttca    840
ttcttcccat cccagtttag aggccacctt ctcgaagcct gggttggggg gactcttcag    900
tgttcccagg acaccttgtg cttccccat aatcactggg tgatcattg              949

<210> SEQ ID NO 6
<211> LENGTH: 832
<212> TYPE: DNA
<213> ORGANISM: Homo sapiens

<400> SEQUENCE: 6
cccagcacac accttgcctc tggctgggac ccccttttgct gctggccctg ctcaggcccc     60
acagcttgat ctcctcatgt tcccactgct gacttcccca agctaactgt gccacagagt    120
gggggacccc ctcccggctc tcacaacccc caccttcctc tgcttcactt ttcaccaact    180
gaaatatggc caaaggcaaa aacccatgtt cccactggcc tgtgggtccc ccatagatc     240 gtaagcccag gaggaagggc tgtgtttcag ggctgtgatc actagcaccc agaaccgtcg    300
actggcacag aacaggcact tagggaaccc tcactgaatg aatgaatgaa tgaatgaatg    360
aatgaatgtt tgggcaaata aacgctgaca aggacagaag ggcctagcgg gaagggaaca    420
ggagtaagac cagcgcacag cccgacttgt gttcagaaga cctgggattg gacctgagga    480
```

```
gttcaatttt ggatgaatct cttaattaac ctgtggggtt cccagttcct cccctgagcg    540
cccaggacag tagagtcaac ctcacgtttg agcgttgggg acgcaaacac gagagtgctt    600
ggtgtgagca cacaggagga gtcacgacag agcagtgtaa gagccgccac gtgggtccca    660
cacaggggga gtcacgacac agcagtgtaa gagccgccac gagggtccca cacaggggga    720
gtcgcgacac agcagtgtaa gagccgccac gagggtccca cacaggggga gtcacgacac    780
agcagtgtaa gagccgccac gagggtccca cacaggggga gtcacgacac ag           832
```

<210> SEQ ID NO 7
<211> LENGTH: 766
<212> TYPE: DNA
<213> ORGANISM: Homo sapiens

<400> SEQUENCE: 7

```
ttacccttgg ggtgggggtg taggatgcag ctggggctgc agttccaggc cacggagagc     60
ctgtgaggct gggccccggg gcgccctggg gaggggatgc ctgatgggga gcctggtggg    120
ggagggtagg ggagggcggg ggaggacggg ggagggcgcc ctgtgtccct gagaaggtac    180
ctggaaatga cactgctaca actcacacca catttcaatc aaggtccata aataaaaacc    240
cattttaaat gtgccaggga gcccaaggtt ctgagtgccc aaggaggcac cgaagacccc    300
tcctgtgggc tgaaaagctc ccgattatcc agcctggccc acacagtccc ctgtacacag    360
ggcttccgag tgcaggtcac agggaacaca gactccatgg tgaatgaatg aatgaatgaa    420
tgaatgaatg agggaaataa gggaggaaca ggccaatggg aatcacccca gagcccagat    480 acccttgaa ttttgccccc tatttgccca ggacccccca ccatgagctg ctgctagagc    540 ctggaaggg ccttgggct gcctccccaa gcaggcaggc tggttggggt gctgactagg    600
gcagctgggg cagaggagg cagggcagg tgggagtagg gtggggctg ggtgcagcag    660 ccggggacct ctggccatct tggatttttt ggatggattt gtttccacat tccgatcgtt    720
aagattcaag atgaaacaag acacagagac ccacacgacc cccgag                   766
```

<210> SEQ ID NO 8
<211> LENGTH: 751
<212> TYPE: DNA
<213> ORGANISM: Homo sapiens

<400> SEQUENCE: 8

```
agatgataga tacatatgtt agacagagat aggatagatg atagatacat aggttagata     60
gagataggat agattataaa tagatacaca ggttagatag attagacaga cagatagata    120
catacataga tataggatag ataactagat acaatagaga tagatagata gatagataga    180
tgatagagga tagatgataa atagatatat agcttagata gagataggat agatgataga    240
tacataggat agatagagac aggatagatg ataaatagat acataggtta gatagagata    300
ggacagatga taaatacata ggatggatgg atagatggat agatagatag atagatagat    360
agatagatag atagatagat agacagacag acagacagac agatagatca atccaagtca    420
catactgatt attcttatca tccactaggg ctttcacatc tcagccaagt caacttggat    480
cctctagacc tgtttcttct tctggaaggt gggaactcta ccttatagga tcagtctgag    540
gagttcacaa ataataagg gcaaagtgcc cggcacattg taggagacta gtaatgtcta    600
taaaatgagg ggcttgaagt aaatgatccc tctagttctc tctactgcta acattctaag    660
acctccttta cattaattgt tctcaagcca catctccctc ccctacagga cttctattta    720
```

```
tttctgatca atttcatgag tacaaataag t                              751
```

<210> SEQ ID NO 9
<211> LENGTH: 945
<212> TYPE: DNA
<213> ORGANISM: Homo sapiens

<400> SEQUENCE: 9

```
actgaacatt tgcttttgaa atttactatc tatgtaccgt tggaaaattt acttaatatc    60
tctgaatttt ttttcttcaa ctgtggagtg aggaaaataa tacctacttt taggtagatg   120
atggatataa cacttttctc tgcatatagt agacactcag tgcataacta tcgccttcct   180
tttccctcta ctcagaaaca aggacatctg ggaccacagc cacatactta cctccagtcg   240
tttcatatca accaactgag ctctaacatt tttctgcaga agctggatat gctgtacttt   300
ttctatgact ttgcgcttca ggacttcaat tctgcttctc agatcctctg acactcggtt   360
gtaggtatta tcacggtctg aaatcgaaaa tatggttatt gaagtagctg ctgagtgatt   420
tgtctgtaat tgccagcaaa aaagaaagga agaaaggaag gaaggagaaa gaaagaaaga   480
aagaaagaaa gaaagaaaga aagaaagaaa gaaagaaaga aagagaaaaa agaaagaaag   540
aaactagctt gtaaatatgc ctaattttat tttggttaca gtttaatctg tgagttcaaa   600
acctatgggg catttgactt ttggataatg ttatgccctg cagccttcca tgaatgccag   660
ttaagatgtc ctaatagcaa ttagtaatcc caaagaaata tagaagaaga actttctttg   720
gaattttaaa ggtgtaattt ggagttaaaa tagttggttt gattgcattt caattatttt   780
ataacatcct taatcaaggg acttgaacat attggatttt cttactgatg agcttttctt   840
tttaatctat agatttgaaa tggttcctaa gctgttttgg gtcaacagga tcactcactt   900
gccagctagt gttgcatcac tgattttaaa tgtcaagtgt ttgtg              945
```

<210> SEQ ID NO 10
<211> LENGTH: 823
<212> TYPE: DNA
<213> ORGANISM: Homo sapiens

<400> SEQUENCE: 10

```
gttggctggg gctcagagag aacaaaaagg cagaggaaaa acaaatttcc cctctcactt    60
ctggagatgg aacactttc ttctgctttt ggacatcaga aatccaagtt ctctggcctt   120
tggactttgg gacttgtgcc agcaccctcc tgggttccct ggcctttggc ctcaaactga   180
aggttacact atcagcttcc gttgttctaa gggcttcaga cttggacagc cacactgcca   240
gcttccctga ttcttcagct tgtagatggt ctgttatggg acttttctca gtctccataa   300
atatgtgagt caattcccca agtgaattgc cttctatcta tctatctatc tgtctgtctg   360
tctgtctgtc tgtctatcta tctatatcta tctatctatc atctatctat ccatatctat   420
ctatctatct atctatctat ctatctatct atctatctat cgtctatcta tccagtctat   480
ctacctccta ttagtctgtc tctggagaac attgactaat acaacatctt taatatatca   540
cagtttaatt tcaagttata tcataccact tcatacatta tataaaacct tacagtgttt   600
ctcccttctc agtgtttatg gctagtaatt ttttactggg tgccagacac taattttat   660
tttgctaagt ggtgaatatt ttttatatcc ttaaaaatat tttgagtgt tgatctgggt    720
aaagttaagt tcaatattgg aaaaatattg attcttttga ggatagttat cttctaatta   780
gtctacctgt tgccccataa atggcatgat tttccactct gtg                 823
```

<210> SEQ ID NO 11
<211> LENGTH: 824
<212> TYPE: DNA
<213> ORGANISM: Homo sapiens

<400> SEQUENCE: 11

```
tactacagca agagcgcttg aaccagatgt aggggagata gcagctggag agcataacag      60
aggcactgac atgtgagcag ctaacgaggc cttttacaag acatctgtga ccacacggcc     120
aagtagaaga aagccgttaa aagcatcaag gtagttaggt aaagctgagt ctgaagtaag     180
taaaacattg ttacaggatc cttggggtgt cgcttttctg ccagaaaacc tctgtagcca     240
gtggcgcctt tgcctgagtt ttgctcaggc ccactgggct cttctgccc acacggcctg      300
gcaacttata tgtattttg tatttcatgt gtacattcgt atctatctgt ctatctatct      360
atctatctat ctatctatct atctatctat ctattcccca cagtgaaaat aatctacagg     420
ataggtaaat aaattaaggc atattcacgc aatgggatac gatacagtga tgaaaatgaa     480
ctaattatag ctacgtgaaa ctatactcat gaacacaatt tggtaaaaga aactggaaac     540
aagaatacat acggtttttg acagctgtac tattttacat tcccaacaac aatgcacagg     600
gtttcagttt ctccacatcc ttgtcaacat ttgttatttt ctgggttttt gataatagct     660
gtgaaaggaa aataaaaact tgggccgggc gcggtggctc acgcctgtaa tcccagcact     720
ttgggaggcc aaggcgggca gatctcaagg tcgggagatt gagaccatcc tggctaacat     780
ggtgaaaacc catctctact aaaaatacaa aaacaaaaaa ttag                      824
```

<210> SEQ ID NO 12
<211> LENGTH: 927
<212> TYPE: DNA
<213> ORGANISM: Homo sapiens

<400> SEQUENCE: 12

```
catgccacta agctgtacac tgaaaaacgg ttaacatgat aaattttatg ttacatacat      60
tttaccacaa tttaaaaaaa ttattaaaaa atactaacaa taggccaagc gtgatggctc     120
acacctgtaa tcccagcact ttgggaggct gagacaggtg gatcaattga gctcaggagt     180
ttgagaccag cctgggtaac acagtgagac ccctgtctct acaaaaaaat acaaaaatta     240
gttgggcatg gtggcacgtg cctgtagtct cagctacttg cagggctgag gcaggaggag     300
ttcttgagcc cagaaggtta aggctgcagt gagccatgtt catgccactg cacttcactc     360
tgagtgacaa attgagacct tgtctcagaa agaaagaaag aaagaaagaa agaaagaaag     420
aaagaaagaa agaaagaaag aaagaaagaa agaaagaaaa agagagagga aagaaagaga     480
aaagaaaag aaatagtagc aactgttatt gtaagacatc tccacacacc agagaagtta     540
attttaattt taacatgtta agaacagaga gaagccaaca tgtccacctt aggctgacgg     600
tttgtttatt tgtgttgttg ctggtagtcg ggtttgttat ttttaaagta gcttatccaa     660
tacttcatta acaatttcag taagttattt catctttcaa cataaatacg cacaaggatt     720
tcttctggtc aagaccaaac taatattagt ccatagtagg agctaatact atcacattta     780
ctaagtattc tatttgcaat ttgactgtag cccatagcct tttgtcggct aaagtgagct     840
taatgctgat caggtaaatt aaaaattata gttaattaaa agggcataaa tgttacctga     900
ctcaataagt catttcaatt aggtctg                                         927
```

<210> SEQ ID NO 13
<211> LENGTH: 731
<212> TYPE: DNA

<213> ORGANISM: Homo sapiens

<400> SEQUENCE: 13

| | | |
|---|---|---|
| ctggttttgg tggaattgac tccctctgtc acaaactcag cttcagccca taccctgagc | 60 |
| catagaccta tccctctaat gcattgtact agtctcaggg ctaataacaa gggagaggtg | 120 |
| tcaagggcc agttccacct ccaccaccag tggaaaagct attcccaggt gaggactgca | 180 |
| gctgccaggg cactgctcca gaatgggcat gctggccata ttcacttgcc cacttctgcc | 240 |
| cagggatcta ttttctgtg gtgtgtattc cctgtgcctt tgggggcatc tcttatactc | 300 |
| atgaaatcaa cagaggcttg catgtatcta tctgtctatc tatctatcta tctatctatc | 360 |
| tatctatcta tctatctatc tatctatcta tgagacaggg tcttgctctg tcacccagat | 420 |
| tggactgcag tgggggaatc atagctcact acagcctcaa actcctgggc tcaagcagtc | 480 |
| ctcctgcctc agcctcccaa gtacctggga ttataggcat gagccaccat gtccggctaa | 540 |
| ttttttttt taagagatgg ggtctcgctg tgttccccag cctgtcttta aactcctggc | 600 |
| ctcaagtgat cctcccatct cagccttcca agtgctgag attacagcag aggcttttaa | 660 |
| gtcaaagctt tccctgctag acaagccct agttaaagtc ctggagcact ggccactgca | 720 |
| gctgcacttg g | 731 |

<210> SEQ ID NO 14
<211> LENGTH: 1026
<212> TYPE: DNA
<213> ORGANISM: Homo sapiens

<400> SEQUENCE: 14

| | | |
|---|---|---|
| cctactcggg aggctgaggc aggagaatcg cttgaaccca ggaggggcg actgcagtga | 60 |
| gccgagatcg tgccactgca ctccagcctg ggtgacagag cgagactcca tctcaaaaaa | 120 |
| aaaaaaaaa aaacagaatc ataggccagg cacagtggct aattgtacct gggaggctg | 180 |
| agacgggagg atcgagacca tcctgggcac catagtgaga ccccatctct acaaaaaaaa | 240 |
| aaaaaattt tttttaaata gccaggcatg gtgaggctga agtaggatca cttgagcctg | 300 |
| gaaggtcgaa gctgaagtga gccatgatca caccactaca ctccagccta ggtgacagag | 360 |
| caagacacca tctcaagaaa gaaaaaaaag aaagaaaaga aagaaaaga aagaaaaga | 420 |
| aagaaaaga aagaaaaga aagaaaaga aagaaaaaa cgaaggggaa aaaaagagaa | 480 |
| tcataaacat aaatgtaaaa tttctcaaaa aaatcgttat gaccataggt taggcaaata | 540 |
| tttcttagat atcacaaaat catgacctat taaaaataa taataaagta agtttcatca | 600 |
| aaacttaaaa gttctactct tcaaaagata ccttataaag aaagtaaaaa gacacgccac | 660 |
| aggctaagag aaagtacttc taatcacata tctaaaaaag gacttgtgtc cagattaaag | 720 |
| aattcttaca catcaataag acaacccaat taaaatggg caaagatttt gaagagatat | 780 |
| ttaaccaaag aaaacatata aatgtgtccg ggcgcgatgg taatcccagc actttgagag | 840 |
| gccgaggcag gcggatcact tgaggtcagg agtttaggac cagtctggcc aacatggtga | 900 |
| aaccctgtct ctaataaaaa tacaaaaatt agctgggtgt ggtggcgtaa gcctgtaatc | 960 |
| ccagctgctc aggaggctga ggcagaagaa ttgcttgaac ctgggaggtg gaggctgcag | 1020 |
| taagcg | 1026 |

<210> SEQ ID NO 15
<211> LENGTH: 977
<212> TYPE: DNA
<213> ORGANISM: Homo sapiens

<400> SEQUENCE: 15

```
cacatgtgga catttcttat tttctcatat tggtggtatg gctcatttat gaagttaata    60
ctggacattg tggggaggct gtgtaagaag tgttaaaggg gatcagggat acattcactt   120
ctcttttcct ttgctagttc tgtggtctta agcaaagtag cctcaaacat cagtttcctc   180
ttttataaaa tgaggaaaat aatactcatt accttgcatg catgatataa tgattacata   240
acatacatgt gtgtaaagtg cttagtatca tgattgatac atggaaagaa ttctcttatt   300
tgggttatta attgagaaaa ctccttacaa ttttcttttc ttttcttttc ttttctttga   360
gactgagtct tgctcagtcg cccaggctgg agtgcaatgg cgtgatctcg gctcacttca   420
atctccacct cctgggttca agtgattctc ctgtttcagc ctccagagta gctgggatta   480
caggtgccta ccaccacacc cagctaattt tttgtatttt agtagagacg gggtttcacc   540
atgttgccca ggctggtctt gatctcctga gctcaggtaa tacacctgca tcggcctccc   600
aaagtgctag gattgcaggc gtgaatcacc gcacctgtcc acaattttct tgttattggt   660
acccttttcat gttggtaaaa tgtatttttat tttctcttat caaataattt tcaatgcaat   720
gagacgtcaa ctttaagccc aaagtagacc agtagtaaaa ctaaggctga aaccattgat   780
tgattattac catatattgt cctaaaatat tcggctttta aaacatttgg tttcattttt   840
catgataaaa atatgtagca ttttttgcact tttaattcac tttgtagagt tctcaatcat   900
ttctaacaca tgcttggcaa tgacaagcca tttgtgaaag agttttgctg gctttaaaat   960
atatgcaaat gtaatat                                                   977
```

<210> SEQ ID NO 16
<211> LENGTH: 706
<212> TYPE: DNA
<213> ORGANISM: Homo sapiens

<400> SEQUENCE: 16

```
aggtctcctc ttctatacag cacatttgtt caaactaaaa acagacctca agtatattct    60
gcactatata gatttttta aagtagcttc agtctccttt aatgtgaaca attgcatact   120
gacttaatct cttcctctct cttctcttcc ttcactctct cccttcctct ctctttctat   180
tctcctcccc tcctccctgt aaaagctacc acctcatcct gggcaccctg gttatatcaa   240
cttcagctat gaggtaattt ttctctttac taattttgac cattgtttgc gttaacaatg   300
ccctgggctc tgtaaagaat agtgtgttga ttctttatcc cagatgtttc tcaagtggtc   360
ctgatttttac agttcctacc accagcttcc cagtttaagc tctgatggtt ggcctcaagc   420
ctgtgtcgtc ccagcagcct cccgcctggc cactctgact cagtctgtcc tctaaatat   480
ggccgtaagc ttacccatca tgaaccacta ctcagggagg ctccatgata gggcaaaaag   540
taaactctga ccagcttggt tctaacccag ctagtaaaat gtaaggatta ggtaagatgt   600
tatttaaaac tctttccagc tcaaaaaact cctgattcta agatagtcac actctatgtg   660
tgtctcttgc ttgcctctgc tgaaatatta gtgactaagt ggtata               706
```

<210> SEQ ID NO 17
<211> LENGTH: 712
<212> TYPE: DNA
<213> ORGANISM: Homo sapiens

<400> SEQUENCE: 17

```
ttattctcca atatttgaa atgtgaatat tacagtaatt tcccttgtcc aaatgagaaa     60
```

```
accagggttc caaagagagg aaattatttg cccaaagtta gtaattttac ctaatcttta      120
cattttaccg gatgggatag aaccaagctg gtcagtcaga gttgacttttt tgccctttca     180 tggaaccttc ctgagcagtg gttcatgaat gaataaactt acagccatat ttaggaggaa     240
agagtcaatc cgaatggtca ggcaggaggg tgctggagca acacaggctt gaggccaacc     300
atcagagctt aaactgggaa gctgatggta ggaactgtaa aattgggacc acttgagaaa     360
ccactttatt tgggatgaag aatccaccca ctattcttta cagagcccag gggactgcta     420
atgcaaacag tgatcaaaat tagtaaagag aaaaattacc tcatagctga agttgatata     480
accagggtgc ccaggatgag gtggtagctt ttatagggag gaggggagga gaagagaaag     540
agagaggaag ggagagtgtg aaggaaggga agagagagta agagattaag tcaatatgca     600
attgttaaca ttaagagaga ctaaaattac ttttaaaaaa tctatatagt acagaatata     660
tttgaggtct gttttttcgtt aaaacaagtg tgctatgtag gagaggagac tt            712

<210> SEQ ID NO 18
<211> LENGTH: 840
<212> TYPE: DNA
<213> ORGANISM: Homo sapiens

<400> SEQUENCE: 18
acaaggcacg gaactcacac ccagcctctc tccatacaac agaatatggg ttcttgcgga      60
gctggactct gcaggagtct atctaatatg gactctgtgt caatgactcc tgggcctcct    120
ctgatcaccc cattaaagtc cttcgattgc tttgagcctc aaatctatgt gacatcaata    180
cgttcatttc ttcctagcac ttagaactgt ttcttgttga tacatttgct ggcttcttcc    240
ctgtctcacc ccttttccta ccagaatgcc agtcccagag gcccttgtca gtgttcatgc    300
ctacatccct agtacctagc atggtacctg caggtggccc ataatcatga gttattcagt    360
aagttaaagg attgcaggag ggaaggaagg acggaaggaa ggaaggaagg aaggaaggaa    420
ggaaggaagg aaggaaggaa ggaaggcagg caggcaggca ggcaggcagg caaggccaag    480
ccatttctgt ttccaaatcc actggctccc tcccacagct ggattatggg ccagtaggaa    540
ttgccatttt cagggttttg ctgtcactgt agtcaggacc atgaagtctt taggcacctc    600
cactccacac accccctggt gagagctccc atctccctgt tctgaaacag ctccccaata    660
tagtactgat tccggttaaa cttgaacccc tgccccctgcc cctgcccctg atttacatga    720
ggacactgag gcccagaggg gtaaagtgac tgccaggggt cacacagcta gaaagtggcg    780
gtgccagaac tggaaggagg ccctcattcc tgagtcacgg cttttccata gcacagcctt    840

<210> SEQ ID NO 19
<211> LENGTH: 780
<212> TYPE: DNA
<213> ORGANISM: Homo sapiens

<400> SEQUENCE: 19
atgaaactgg acacagaaac cagaccccag agcacatacc gtatgagtcc attggtatga      60
agtttaaaaa cagatggcac tagtccaaag gattggaagt tggaatagtg gttaccagga    120 ctgggggggag gaagggatgg tggatggtga acaaaaggac cttggagggc tcctggggtt    180
ctaggaatca atcttccttc tttccttcct tccttccttc ctctttctct ctttctttct    240 gttttttattt caataggttt ttaaggaaca ggtggtgttg gttacatgaa taagttcttt    300
agcagtgatt tctgatattt tggtgcaccc attacccgaa taaaaatctt ctctctttct    360
tcctctctcc ttccttcctt ccttccttcc ttccttcctt ccttccttcc ttccttccta    420
```

| | |
|---|---|
| ccttctttcc ttcaacagaa tcttattctg ttgcccaggc tggagtgcag tggtacaatt | 480 |
| atagcttttt gcagcctcaa cctcctgggc tcaagtgatc ttcctgcccc agcctcctga | 540 |
| gtagccagga ctacaggaat gtgccaacat gcctggctaa ttttaaaaaa tttttttatag | 600 |
| agaagaggtc tcactatgtt gcccagacta gacttgaact ccttccctca agtgatcttt | 660 |
| ctgcatcagt cttccaaagt gctgggattg caggcatgag ccacctcacc cagccttaga | 720 |
| aatgttctgt tcttgacct gagagctgga tatacaggat gctcactttt gtgaaaattc | 780 |

<210> SEQ ID NO 20
<211> LENGTH: 887
<212> TYPE: DNA
<213> ORGANISM: Homo sapiens

<400> SEQUENCE: 20

| | |
|---|---|
| gtacttcaga gtcaggatgc ctctcttgct ctgggcctcc ttgcccacat aggagtcctt | 60 |
| ctgacccatg cccaccatca ctccctggtg cctagggtgc cccacaatgg aggggaagac | 120 |
| ggcctgggga gccttgcgca tgctggagca gttgtcgacg acgacgagcg cggtgatagc | 180 |
| atcatccatg gtgagctggc ggcgggtgcg gacgcaaggc gcagcggcaa ggacaaggtt | 240 |
| ctgtgctcgc tgggctgacg cggtctccgc ggtgtaagga ggtttatata tatttctaca | 300 |
| acatctcccc taccgctata gtaacttgct ctttctttcc ttcctttctt tctttctttc | 360 |
| tttctttctt tctttctttc tttctttctt tctttctttc tttcttttc tttctttctt | 420 |
| tctttctttc tttctttctt tcttttcttt tctttctttc tctttctttc tttttcttc | 480 |
| tttttcttcc ttccttcctt tctctctctc tctctttctt tctttctaac tctctttgtc | 540 |
| tcttctttc tttcttttga cggagtttca ctcttgtcgc ccagattgga gtgcaatggc | 600 |
| atgacctcgg ctcactgtag cctccacctc ccaggttcaa gcgattatcc tgcctcagcc | 660 |
| tccctaggag ctggaattac agacgtgcac caccaagcct ggctaatttt tgtattatta | 720 |
| gtagagacgg ggtttcacct tgttggccag gctggtctcg aactcctgac ctcaggtgac | 780 |
| ccacctgcct taggctccca aagtcctggg attataggca tgagccacag tgcccagcct | 840 |
| tcttttcatt taatactata gtagtgtgat cctctctacc tattaca | 887 |

<210> SEQ ID NO 21
<211> LENGTH: 720
<212> TYPE: DNA
<213> ORGANISM: Homo sapiens

<400> SEQUENCE: 21

| | |
|---|---|
| ttctgttttg cggtggttcc tagtatggta cctggccaag ggcacactag atctttgtca | 60 |
| aggtaatgac tacttttat taaatgcttt ccatgtatca agttctgtgc caagcacttg | 120 |
| acatatatca ttttatttta tcccgtgaag tagttattgg tatcttcatt tacaaataaa | 180 |
| aaaacaagct tagtacttaa ctcactgcct tgaacataat tattgcttta aaggtagcta | 240 |
| ggattcttaa tagctattat taccaaagca tgaacaatca gtaaaaagca aacctgagca | 300 |
| ttagccccag gaccaatctg gtcacaaaca tattaatgaa ttgaacaaat gagtgagtgg | 360 |
| aaggaaggaa ggaaggaagg aaggaaggaa ggaaggaagg aaggaaggaa atgaagacaa | 420 |
| tacaaccaga gttgttcctt taataacaag acaagggaaa aagagaactg tcagaataag | 480 |
| tgttaattat aatatccagg ggtgggatac agaggtttta gcatctgctc tttgccaagc | 540 |
| actgcactta ttcctgagga atacctgagg gaaaaagtat ggtttctcac aggatctagt | 600 |

| | | |
|---|---|---|
| tggactggaa atatgacatt catattggaa tccagtgtct ttttctgaaa aagagagttc | 660 | |
| gttccaagct tagctcacat gcaagctaag acaaccacta gaaattactc tccccagggc | 720 | |

<210> SEQ ID NO 22
<211> LENGTH: 780
<212> TYPE: DNA
<213> ORGANISM: Homo sapiens

<400> SEQUENCE: 22

| | |
|---|---|
| gtcatgccta cagtgtaacg ggaattgacc aggtaggcga cttgaactcc aactgcaggc | 60 |
| tatggggaga catgtgacaa tgctaatccc ttaggcattt attcagtgca ttgcagttta | 120 |
| aatgtctgcc tttcaggcat ttcagagatt atgtcaccta aagaggcagg ctggaattca | 180 |
| aaacggcaag ccaggaaaga gagaaaccat gtgattccac cgcagcacaa aactcgttta | 240 |
| gcagctgtaa gcgcctggtc tttgtttatt tttaatttcc tttctttccc aattctcctt | 300 |
| cagtcctgtg ttagtcagga ttcttcagag aaatagaatc actagggaac caaatatata | 360 |
| tacatacaat taaacacaca cacacctatc tatctatcta tctatctatc tatctatcta | 420 |
| tctatctatc tatctatcta tctatctatc tacatcacac agttgaccct tgagcaacac | 480 |
| aggcttgaac ttatatgggg attttcttcc atctctacca cccctgagac agcaagacca | 540 |
| actcctcctc ctccttctca gcctactcaa catgaagata taaggatga agacctttac | 600 |
| aatgacccag ttccacttaa taaatagtaa atgtatttcc tcttccctat gattttcttg | 660 |
| ataacatttc ttttctctgg cttatttatt gtaagaatac agtatataat ataaataatt | 720 |
| ataaaacatg ttaattggtt ctttacgtta tcgataagac ttctggtcaa tggtaggcta | 780 |

<210> SEQ ID NO 23
<211> LENGTH: 780
<212> TYPE: DNA
<213> ORGANISM: Homo sapiens

<400> SEQUENCE: 23

| | |
|---|---|
| gagcccaagt ttaaacccag gccctctgtg tcccctaca gggtgactgc atctccgagt | 60 |
| cctggcttgt catgcctgac agagggctgc cgagtgagca gcttaaggca tcctgccact | 120 |
| gtgcagctgc caaccctaca gcccggcagc cctgcgggag gaagctctag tgcaggcctc | 180 |
| ttaggatctg gggtccagga tgctgatttc agggccggga ccttgggcac cgtccctctg | 240 |
| gtctgcataa gacccactat gggcaaacct taaacctgat cgttggaatt ccccaaactg | 300 |
| gccagttcct ctccacccta tagaccctgt cctagccttc ttatagctgc tatgggggct | 360 |
| agattttccc cgatgatagt agtctcatta ttattattat tattattatt attattatta | 420 |
| ttattattac tattattgtt ataaaaatat tgccaatcat acattcgcgt gatcactcac | 480 |
| actgtgccgg gcactcttga gagcacttta catatattgt ctcatttaat tctctcaact | 540 |
| tgggcacagg cactgtcact atttccattc tacagctgag gagactgaag cacagagagc | 600 |
| cttagggact tgcctgaggt cacacagcta agaaatggtg gagccaggat cagaaaccag | 660 |
| gccacctaca gagctcccct caaggggaac agcatccggt tccagaggct gtgatttat | 720 |
| cagctacact gtgtgactcc atcttcacac tctcctgccc ctcaagaaga catataacct | 780 |

<210> SEQ ID NO 24
<211> LENGTH: 780
<212> TYPE: DNA
<213> ORGANISM: Homo sapiens

<400> SEQUENCE: 24

```
atgaagagat ggtcaggcga ggtatggggg aagggggcgtg gagcttccat gtcctccctg    60
ggcgccaccc tccaggaacc tccacgtgtt cagctataca gaagcttcct gaacccagtc   120
ctcttggggt ttgagggaag cttcatgaca tcagcattcc ttcctccagg gtattaatgg   180
gaccctctct gaagagattc ttaagaccca cggccagaaa gttgggtaaa gactagagtc   240
ctgccttggg gcaggtgaaa ggagtgcaag agaaggtaag agagattctg ttcctgagcc   300
ctaatgcacc caacattcta acaaaaggct gtaacaaggg ctacaggaat catgagccag   360
gaactgtggc tcatctatga aaacttctat ctatctatct atctatctat ctatctatct   420
atctatctat ctatatcata acaccacagc cacttagctc caatttaaaa gattaatcat   480
aaacatttgg gaaggagagt gaagattttt gtgatgttaa ataagaatga ttatactaaa   540
aaccaaaata atatgttatt tatggctggg tgtggtggct taagcctgta atcccagaac   600
tttgggaggc caaggcttgt ggatcacttg agcccagaag ttcaagacca gcctgggcaa   660
catagggaga ccctgtctct acaaaaaatt ttaaaattag ctggacatga tggcacgcac   720
ccgtagtctc agctactcag gaggctcacg ccactgcatt ccagtctggg taacgcacac   780
```

```
<210> SEQ ID NO 25
<211> LENGTH: 780
<212> TYPE: DNA
<213> ORGANISM: Homo sapiens

<400> SEQUENCE: 25
```

```
gtcaggagtt cgagaccagc ctggccaaca tggcgaaacc ctgtctctac taaaaataca    60
aaaaaattag ctgggcatgg tggtgtgttc ctgtaacccc agctactcag gaggctgagg   120
caagagaatc gctggaaccc aggaggtgga agttgcagtg agctgagatt gcaccactgc   180
actccagtgt gggcaacaga gcgagactct gtctcagaaa aaaaaagaa tacatgaaat   240 cagagaaact caaattgtga tagtagtttc ttctggtgaa ggaagaaaag agaatgatat   300
cagggaagat gaaaaagag actgtattag taaggcttct ccagagagaa agaatcaaca   360
ggatcaatgg atgcataggt agatagatag atagatagat agatagatag atagatagat   420
agatagacag acagacagac agacagacag acagatgaga ggggatttat tagaggaatt   480
agctcaagtg atatggaggc tgaaaaatct catgacagtc catctgcaag ctggagaccc   540
agggacacta ggagcatggc tcagtccagg tctaaaagcc aaaaaccag ggaaactgat   600 ggtgtaatta tccatcccag gtggaaggcc tgagaacctg gagtgcccct ggtataagtc   660
ccagagtaca aagacaggag agcctggagt tctgacttcc aagggcagaa gaatgtgtcg   720
cagctccagg agagagagag aaagaatttc tttcctccgc cttttgattc tatctggggg   780
```

```
<210> SEQ ID NO 26
<211> LENGTH: 74
<212> TYPE: DNA
<213> ORGANISM: Homo sapiens

<400> SEQUENCE: 26
```

```
cagcaacagc acccagcttg gcgcgggccg agggctccca ggcatgacac tgcagatccg    60
cgactgagcc tgtg                                                     74
```

```
<210> SEQ ID NO 27
<211> LENGTH: 82
<212> TYPE: DNA
<213> ORGANISM: Homo sapiens
```

```
<400> SEQUENCE: 27
ttaagtaatg tcaagaaggc aatgcgctga gactggagag cagaagaaag catcactggg    60
ctaacacagc aaatgtggaa cc                                              82

<210> SEQ ID NO 28
<211> LENGTH: 84
<212> TYPE: DNA
<213> ORGANISM: Homo sapiens

<400> SEQUENCE: 28
cagcctagac gtcaagttac agcccgcgca gcagcagcaa aggggaaggg gcaggagccg    60
ggcacagttg gatccggagg tcgt                                            84

<210> SEQ ID NO 29
<211> LENGTH: 91
<212> TYPE: DNA
<213> ORGANISM: Homo sapiens

<400> SEQUENCE: 29
gccttcagca ggaagtccac aaccctgcaa agagggcgc tgcgtcacgc gggcacacgt     60
ccgcagtctc ggagtctgtg tgaggcacag g                                    91

<210> SEQ ID NO 30
<211> LENGTH: 103
<212> TYPE: DNA
<213> ORGANISM: Homo sapiens

<400> SEQUENCE: 30
cttctccgag gtcgcaggtg gaacgggctt gcgcgtgaga acggggcctg ggcttaactc    60
actggggcct cccccgggtg gccgaggttc ttttcccacg ccc                      103

<210> SEQ ID NO 31
<211> LENGTH: 108
<212> TYPE: DNA
<213> ORGANISM: Homo sapiens

<400> SEQUENCE: 31
cagcatccat cccatggtat gggtgggaag cctgaggctt gggctggtca agggacctgc    60
gccaggtcat gcagatgaac agcaggggag cccaagttta aacccagg                108

<210> SEQ ID NO 32
<211> LENGTH: 540
<212> TYPE: DNA
<213> ORGANISM: Homo sapiens

<400> SEQUENCE: 32
cttgaacctg agaggcagag gttgcagtga gccgagacca tgccattgca ctccagcctg    60
ggcaatagag taaaactcca tcctcccgct ccaaaaaagt agacaacgtc catgaggtga   120
tgaggaaggg gttatcgtgt gttgcttgct gagaacagga cccccagact caccgtgtcg   180
acgccggcca gcagcatctc agtcacgttg gcgtagatct cctgcagcgt cagagcctgg   240
ctaaggaaga ggtatgtgag aagtcccccg ctcaccctcc ggcctcggtc catttggtac   300
tgtatgtccc tcaacttgtt gtcaacatga atttggcctg tttgaaaaca gtatttcttt   360
tgaaaggagt ttgggttgag aatcatcttt tcagtctcaa agccctctgt cctcccagta   420
gcttaactaa accagtggca ggtgacagag ggtaaggaaa cccaatttat ctaacgtcaa   480
cctgggagtt tcactcatac acttgcttat gtaaatgaat gaaaagttaa aagacaagct   540
```

<210> SEQ ID NO 33
<211> LENGTH: 537
<212> TYPE: DNA
<213> ORGANISM: Homo sapiens

<400> SEQUENCE: 33

```
agagagccca ggagacaggc agaaaggaag gcatgtgacc ggatcacaat catcagctct    60
ctgctgtcct ctttgggaag ggttttagta ttaaaaggac attttattctc attaatgcaa   120
aattaaggag ttttaaaagc ttttacaacc tagactccct ctgagaggtt agccttgaca   180
ccctaatcgc cttctgctcc cgccactgct cggtgccaag cagctcccac ggccccggcg   240
ggtctgatga tagccggaca ggagggagga aggggaggag aagagcctg catcagctcc    300
tacgattgcc cagccccatc ctgggagtga ttaaacggtg catcaccaaa tgccagtccc   360
actgacaggc aggtcaccgt gcacttcagg gcactctaaa ttgccgactc tccatgtaga   420
gagggatgaa tccaatattg aaatcctcat aactacagcc ccccaaagta gccgtccatc    480
ttctgcttaa aatgttgatc tgtagtaaaa tgttgatttt gttgaagctg agtgatg       537
```

<210> SEQ ID NO 34
<211> LENGTH: 609
<212> TYPE: DNA
<213> ORGANISM: Homo sapiens

<400> SEQUENCE: 34

```
ttgaacctag gagatggagg ttgcagtgag ctgcgatcat gccacttccc tccaggctgg    60
gcaacagagc gagactccat ctcaaaaaaa caaaaagaa aaccaacctt ttgaatgtag    120
gggaaacttt tcaaaggata tctagttttc aattacagta aacttgtgga agggaggttc   180
agagttgaga ttgagattat agattttgct gatgataaac catgagttcc agaggacata   240
gtagactatt ctgggcagtt atacaggggt ggatggaatg tgggagtggg gttgtatagt   300
gccataaaga aatgagagtc cggattaaaa ataatgagct ggactcgcga gccttttgta   360
actgaaataa atagaaaaat aagaaataca ttatttctgt gattgttgag aggaagaaat   420
ggtggaaatc ttgtgagaag cacactgagc tctagcacca cctcttcact cctacagatg   480
gtggaataaa cggcaggcaa gttcaaaatc acatatagtc attattgcaa gatagttcta    540
tggatataga tactacatac aatataaatc atgctcattg aatggttcag tggaaactac   600
tctgaactt                                                           609
```

<210> SEQ ID NO 35
<211> LENGTH: 732
<212> TYPE: DNA
<213> ORGANISM: Homo sapiens

<400> SEQUENCE: 35

```
gagtttggga agggtatttt agggggaat aacttttgag ttcccagcgt gcgggggaag    60
ggcgggacgg gagggtgtcc caaggcctga gaagatcagt gtggggcagg ggtcaggaat   120
aacctgggag ggggccttgt atgggggaaa taattgggaa gaggagagat gggatgaagg   180
gggcctcagc gggtcgtctc ctgtgtatgc agggtcgttc tgcagcgtct ctgggagatg   240
gcgtccctgg gagccctcag gtcgccccta cccgctgcgg ggtgctttcc tggcgtcacg   300
ccttcctggc ccctggaggg aaggaagtga aactctcctc ttcccccacc cggctggaat   360
gcgagtcagg aagcctgggg ctccagcctg ctccggctgc ccgggtcggg gatggggagg   420
```

```
ggcgtggccg gagcgcaaag ccccgcccct ccgcgccccc ccccggaag ccccgccgcc    480 ggccgctaag gcgatcacgg gccctgtcct aatatgggca accggaagcg gcccgcgcga    540
ctgccctacg tcactccgtc caaatttagt tgtggaagtc agcgggcgct ggtggcggga    600
aggcgccgcg agccagtgcg ggcggaaagg gggcggggg cgcaccaccc cttaaagggc    660
ccgcaccagg aatgaatgga gccattcgaa caattctgca tcctattttt ggaggaagtg    720
gaattagtat tt                                                        732
```

<210> SEQ ID NO 36
<211> LENGTH: 488
<212> TYPE: DNA
<213> ORGANISM: Homo sapiens

<400> SEQUENCE: 36

```
tttatttta aaaagaaag aagaagaga aagggatgg gtttattgtc cttttcaaca    60
gactagagta tacggggtga aactgcttca cttgattcaa taaaatcgtt tccggtaaca   120
ggccccagga atcctagacc taagcctggc gcgaaactac atttcccaca atccttcggg   180
ggctgataag gctccgcaat ggtctgaact acaattccca caatccaggg cgatttccgc   240
tttgtcgcgt ttcctcaagg ctccgcccca tttcccatct ttcttttcag tccttgcgca   300
ccggggaaca aggtcgtgaa aaaaaggtc ttggtgaggt gccgccattt catctgtcct   360
cattctctgc gcctttcgca gagcttccag cagcggtatg ttgggccaga gcatccggag   420
gttcacaacc tctgtggtcc gtaggagcca ctatgaggag ggccctggga aggttagtgt   480
gtaagggg                                                             488
```

<210> SEQ ID NO 37
<211> LENGTH: 248
<212> TYPE: DNA
<213> ORGANISM: Homo sapiens

<400> SEQUENCE: 37

```
accctcattt cacatttcac cccttcctca aaatgctccc ttcatattac ctcctcagaa    60
accaagaata tggctactaa ttctccctgg ccccatgctg caggtgaacc ggtagcccag   120
aggtatcaca taattctccc aaagtcacac agcaaatcaa gatgcatcca ggactagaag   180
ccatgtcagc cacactggga agccccagcg aagctgacag aaagtttcat aataccaccc   240
tctccct                                                              248
```

<210> SEQ ID NO 38
<211> LENGTH: 480
<212> TYPE: DNA
<213> ORGANISM: Homo sapiens

<400> SEQUENCE: 38

```
aaacacccca gtctgaaaat aaccatagtt tgttgctctt acgagtgaaa atgctatttc    60
atacacgaag ctttgtcctt cagcacccaa gatttaagga taattatgga tgaatatat   120 ggattcattt taaatccttt ggcaaatctg ctctgggggc ttctctgtca gaaggtctct   180
ccttcccaac tctaagaaac gttattccta tgcaaatgct gctgagtcaa gacggggagg   240
gaagtgcaga gagaagggct ggtggcatgg tcagtaagtc atgagggtga gattagggt   300 gacacactgc ttgccaacgt aggagaaggc tctgccctca cctagcaggt ctgatggaag   360
ccccttattc cgtccttcct gccgggttcc accgagatca aaaaggaat gctgtgtagg   420 agcacatgat atgtgataaa tgagagaaag gtcaaacatt taaggaacgc ccagagaaag   480
```

```
<210> SEQ ID NO 39
<211> LENGTH: 463
<212> TYPE: DNA
<213> ORGANISM: Homo sapiens

<400> SEQUENCE: 39
cgctgggcgc gagtgaagag cccatcaggc aggtcgcgca ggaagcgctt gagcgccgag      60
gaaacatcat ccacgtgctg ctcgccctcc ttgaggtgca cagagcgcgc atcctgccgc     120
aggctctcca gcagccgctg tgtcttcgat gtctgcccac acttgcggta gatgccctcg     180
gaggtcaggc ctagggaggg gcggggccaa gcgttcgggg cctgaggcat agagtcatgg     240
ggcggggccg cgcagctctg ggcgggagg cggctctccg ggaggggcgg ggctggcacc      300
ctaggggcag ggctcaccgc actgcgtgat gtagtccaca cagcggtaca cgatcaccgg     360
gatatccgag tccccaagct gctgctccga cagcgtgtcc cccatgctgg cggctgcttt     420
ctggatggcc cccagccaac ccatgaagtc cagccgccgc tcg                      463

<210> SEQ ID NO 40
<211> LENGTH: 324
<212> TYPE: DNA
<213> ORGANISM: Homo sapiens

<400> SEQUENCE: 40
cgatcccgtt cactcgcctg cccatccgca tggccaaggg gctgggcaac atctctgcca      60
agtatcgctg gttcgccgtc ttctacctga tcatcttctt cttcctgatc ccgctgacgg     120
tgtttggcct ctcgctggcc ggctggcggg tgctggttgg tgtcggggtt cccgtcgtct     180
tcatcatcat cctggtactg tgcctccgac tcctgcagtc tcgctgccca cgcgtcctgc     240
cgaagaaact ccagaactgg aacttcctgc cgctgtggat gcgctcgctg aagccctggg     300
atgccgtcgt ctccaagttc accg                                           324

<210> SEQ ID NO 41
<211> LENGTH: 264
<212> TYPE: DNA
<213> ORGANISM: Homo sapiens

<400> SEQUENCE: 41
cgcgagagga ggggaatggc aggtccccgc ttcgcgtacc ttggaaataa gctcatcgtg      60
tttggccagg tgtgcacggc agtggacaca gctgtaagtg cggtgacagc ggggcagata     120
gctgcggaaa gtcttggtgg ggaggcaggc agggcccgga ccggggtcac agctgggcat     180
gacgggctgg aggacaatgc cctggtgggc tggaggggct ggcgccgtgc agcccccgca     240
gagacggtcg caggtgaagc agcg                                           264

<210> SEQ ID NO 42
<211> LENGTH: 300
<212> TYPE: DNA
<213> ORGANISM: Homo sapiens

<400> SEQUENCE: 42
cggtgctcac cggctcgacc ccccagcaac acgagagacc tcacagaggg agtcacacta      60
acgtggtcgg ggctccagag cgaaacccca accactatgc tcacagccag gaccgagcag     120
gctgggccaa cggcagtccc tgcccagcgc ccggctccct ccgagtggcc agcagcgccc     180
tctggtggag actggctcgg cctccgcggc actgcattcc cacggcagtg gtccatctag     240
```
tccccaagtc ctagaggagg ccctctctc tccctcagcc ctggcagggt ccttggcgcc        300

<210> SEQ ID NO 43
<211> LENGTH: 482
<212> TYPE: DNA
<213> ORGANISM: Homo sapiens

<400> SEQUENCE: 43
ctgagagcca tggcgagagc aatgctaggc cggtgaacag taggctcgag tttaggtttg         60
aaaggtgagg tgagagaaat cggcaaaggg aaccctgcg cagatctcgg gttcctttac        120
tttataaccg cggggtccgg ttcctgccag gtgactgcac agttcatcct catgaccctt        180
ctcagccaat gggaagagag cgacgcccag gaagtcccgc cctgtcccgg cctgtgggcg        240
cgtcctcggg tccttctacg tcgctgactc gtgacctgac cggtatttt ttcctaaact        300
gggatcttgg gtaggaggaa gaaaagataa ggagttcctc tatctgaaat tagtcgggct        360
gttttgagga gtactggtta ggtatattgg agaatgtgcc tttattggaa ttttcgcat        420
aattacacag ggttatgggc ttaggggtac atgattgttg gccgggcgtg gtggctcacg        480
cc                                                                      482

<210> SEQ ID NO 44
<211> LENGTH: 1301
<212> TYPE: DNA
<213> ORGANISM: Homo sapiens

<400> SEQUENCE: 44
ttgcagggct agccaggata agcaatggat gctgtttaat tcatcttagc ctcagaatgg         60
atcaagagta aggtgctatt ccctctcaaa ggaaacgcta attaaatgat ccttggtgaa        120
actcaggctg agggctcaga ggtgtggtga tgtaatgggc tttggaatta gacagggact        180
gaacatttgc ttttgaaatt tactatctat gtaccgttgg aaaatttact taatatctct        240
gaattttttt tcttcaactg tggagtgagg aaaataatac ctacttttag gtagatgatg        300
gatataacac ttttctctgc atatagtaga cactcagtgc ataactatcg ccttccttt        360
ccctctactc agaaacaagg acatctggga ccacagccac atacttacct ccagtcgttt        420
catatcaacc aactgagctc taacattttt ctgcagaagc tggatatgct gtactttttc        480
tatgactttg cgcttcagga cttcaattct gcttctcaga tcctctgaca ctcggttgta        540
ggtattatca cggtctgaaa tcgaaaatat ggttattgaa gtagctgctg agtgatttgt        600
ctgtaattgc cagcaaaaaa gaaggaagaa aaggaaggaa ggagaaagaa agaaagaaag        660
aagaaagaa agaaagaaag aaagaaagaa agaaagaaag agaaaaaga aagaaagaaa        720
ctagcttgta aatatgccta attttatttt ggttacagtt taatctgtga gttcaaaacc        780
tatgggcat ttgactttg gataatgtta tgccctgcag ccttccatga atgccagtta        840
agatgtccta atagcaatta gtaatcccaa agaaatatag aagaagaact ttctttggaa        900
ttttaaaggt gtaatttgga gttaaaatag ttggtttgat tgcatttcaa ttattttata        960
acatccttaa tcaagggact tgaacatatt ggatttctt actgatgagc ttttcttttt       1020
aatctataga tttgaaatgg ttcctaagct gttttgggtc aacaggatca ctcacttgcc       1080
agctagtgtt gcatcactga ttttaaatgt caagtgtttg tgaaggtgta aaaaggcaaa       1140
gcaaaacttg agaaactgag gactcctag actcgctgtc catgcccaga gtgaatgcaa       1200
tgtttcctaa ccctaatgag tagactgtga gaatgacgta gcttgaccct atattttaaa       1260
tttaaaaatc tacctaatca gctcagtgga gtctgggagt t                          1301

<210> SEQ ID NO 45
<211> LENGTH: 660
<212> TYPE: DNA
<213> ORGANISM: Homo sapiens

<400> SEQUENCE: 45

| | | | | | | |
|---|---|---|---|---|---|---|
| gaactgaaat | tcggaggga | gctaagagct | ccatgttttt | attttactat | tctttaaaca | 60 |
| agcagacaca | gtgctggttt | ctgatcatgt | gggaggtgtg | taggagagaa | cacaggtaaa | 120 |
| gtaaaataaa | aatataaagc | cataaatgcc | acaacagaaa | ttcaatgaac | aaacatagaa | 180 |
| gagaatacct | taattcctag | aagacagaga | aagagttta | tgaaaggcat | cctagaagag | 240 |
| gagatatttg | cactgattct | taaaaggtga | gagtacaaga | cttcctctcc | aggagtcggc | 300 |
| ggagggaggg | cagactcaaa | gtgctcctgg | acgcagaggc | tcttgtcaga | gggcacagac | 360 |
| cggttggaac | aaagtaagga | tctgagcgac | cccaactttg | cagccgaggc | ctccagctcc | 420 |
| gaggtgcata | gcaaccctag | ggttccggta | ggcgttcctc | cgtccgcgac | cctggcagag | 480 |
| ccgcagagcc | ctcctccaga | cccgaccact | gccccaggcc | ccgagcgacc | ggaaggctca | 540 |
| gcagcaggcc | gcggagaagg | gcggcgccca | ccaggcccct | agcactgccc | agtctggccc | 600 |
| ggcacagctg | ctgcagaagg | cgcacgacga | gctcgtgtgg | tacatgcggg | tcaaggacca | 660 |

<210> SEQ ID NO 46
<211> LENGTH: 349
<212> TYPE: DNA
<213> ORGANISM: Homo sapiens

<400> SEQUENCE: 46

| | | | | | | |
|---|---|---|---|---|---|---|
| cgcggacctc | ggactcacca | agtgccgagt | ggcagatgtg | ctgctgaggg | tgcgccgggg | 60 |
| cgcagctgca | tgcctcaccc | agccccgggg | gccgcagcaa | cgccagcagc | cgcagcaaca | 120 |
| gcacccagct | tggcgcgggc | cgagggctcc | caggcatgac | actgcagatc | cgcgactgag | 180 |
| cctgtgaggt | ctgggggact | ggacggcccc | agcagggctc | cttcccaagg | ccgttgtgcc | 240 |
| cctcgcccca | ggctttatga | ggtggcccta | agggccaatc | ccgccccgac | gggctccgcc | 300 |
| ttcctttggc | tctaggccac | ccgcggaggc | aggacccgag | gctcttccg | | 349 |

<210> SEQ ID NO 47
<211> LENGTH: 422
<212> TYPE: DNA
<213> ORGANISM: Homo sapiens

<400> SEQUENCE: 47

| | | | | | | |
|---|---|---|---|---|---|---|
| cgcgtgccac | ggggaggagg | actggggggcg | tttgaggggc | tcagcgcacc | agaggagtga | 60 |
| ggtggaggag | ggcgttcccg | cgtcctcctc | ttcaatccag | agcagctcaa | cgacgtggct | 120 |
| cccttctat | gtatccctca | aagccttcgc | gtcggattaa | aggtgttctt | gatccttctt | 180 |
| taccaaccac | ggtgcgggcc | aggcgtgatg | agggatgagg | gagaggaaac | ctcagtagca | 240 |
| aaattgttca | gaggacgttc | ggagggcgcg | gggagcagcc | ggatgcacac | ctaaagtctc | 300 |
| gcaacaccca | actcctcctc | cgcaggcagt | cccttaagag | aatagataaa | aaggccaagc | 360 |
| aaagatcctc | tccctcggc | ccggggcac | tgccacattc | agtctaggca | tccccttctg | 420 |
| ct | | | | | | 422 |

<210> SEQ ID NO 48
<211> LENGTH: 620
<212> TYPE: DNA

<210> SEQ ID NO 48
<211> LENGTH: 620
<212> TYPE: DNA
<213> ORGANISM: Homo sapiens

<400> SEQUENCE: 48

```
gctcgggtcc gggggtgtgg atgaaggagc cccaggcagt ctcatgagca cagagagcac       60
cgtaggctgc ggtgagctcc ggctcatcct cccagctaca tgactgcagc ctcctatgcg      120
catcccagcg ggcatggatc agggccagtc cctgagcatc cttggccagg aagctcaggt      180
accccagtgg gttgccaggg acggcctttgg tcaagtggca ggaggtcctg taccagcgga     240
gggcagggga gcccccagg gccaccccca ggaagcccag catcccaaac agccctgcct       300
gaaccccat tctgcactgg cccagtccag tcagacaaag ccctgggat gcctgccctt        360
ggtgccccca ccaggcggca gctgagcagt ggaacggaag cggagcccag caggcccggt      420
gcggcgggac caatgaatgg agctgcggga ggaggaggaa agaggctgga gtatggggtg      480
atcttgggct tgtaaccgaa tccaccagcc gggcaggacg ctgattggct gaggagtgca      540
cttgccaggg cccacgcccc cattctgcct gccttctcag caccatccag tcacctgctg      600
ccagccctgc ctagattggg                                                  620
```

<210> SEQ ID NO 49
<211> LENGTH: 1012
<212> TYPE: DNA
<213> ORGANISM: Homo sapiens

<400> SEQUENCE: 49

```
cggcgcgctg gctccctgga gcggggcggg acgcggccgc gcggactcac gtgcacaacc       60
gcgcgggacg gggccacgcg gactcacgtg cacaaccgcg ggaccccagc gccagcggga      120
ccccagcgcc agcgggaccc cagcgccagc gggaccccag cgccagcggg accccagcgc      180
cagcgggacc ccagcgccag cgggacccca gcgccagcgg gtctgtggcc cagtggagcg      240
agtggagcgc tggcgacctg agcggagact gcgccctgga cgcccagcc tagacgtcaa       300
gttacagccc gcgcagcagc agcaaagggg aaggggcagg agcccggcac agttggatcc      360
ggaggtcgtg acccagggga aagcgtgggc ggtcgaccca gggcagctgc ggcggcgagg      420
caggtgggct ccttgctccc tggagccgcc cctccccaca cctgccctcg cgcccccag       480
cagttttcac cttggccctc cgcggtcact gcggattcg gcgttgccgc cagcccagtg       540
gggagtgaat tagcgccctc cttcgtcctc ggcccttccg acggcacgag gaactcctgt      600
cctgccccac agaccttcgg cctccgccga gtgcggtact ggagcctgcc ccgccagggc      660
cctgaatcca gagaaagtcg ctctttggcc acctgaagcg tcggatccct acagtgcctc      720
ccagcctggg cgggagcggc ggctgcgtcg ctgaaggttg gggtccttgg tgcgaaaggg      780
aggcagctgc agcctcagcc ccaccccaga agcggcctcc gcatcgctgc ggtgggcgtt      840
ctcgggcttc gacttcgcca gcgccgcggg gcagaggcac ctggagctcg cagggcccag      900
acctggggttg gaaaagcttc gctgactgca ggcaagcgtc cggagggggc ggccaggcga      960
agccccggcg ctttaccaca cacttccggg tcccatgcca gttgcatccg cg             1012
```

<210> SEQ ID NO 50
<211> LENGTH: 295
<212> TYPE: DNA
<213> ORGANISM: Homo sapiens

<400> SEQUENCE: 50

```
cgcgctgagc ggttggtgag gagacagggg tcatcgtgca ggttgtcaaa gggcagcagg       60
gcccggccgt tgtcttggaa gcgctggttg acggccagca gccccagctg gttggacatg      120
```

```
ttgcgcaggt tcctggccag gggctcctcg ctgccgtaca ccatgctggc gtccacgaag      180
gaagtgagcg cgttgatctg gttgcggatg gtgatgttgc tcccggggca agccgggcag      240
gagcggaaga acgggatgca gtcggcttgg ttcttgatgc gggggtcatt gggcg           295

<210> SEQ ID NO 51
<211> LENGTH: 801
<212> TYPE: DNA
<213> ORGANISM: Homo sapiens

<400> SEQUENCE: 51
tgcccaccag aagcccatca ccaccagcaa agccaccacc aaagccacca cccaagccag       60
caccaaggcc accaccatat cctcccccaa agccactacc aaagctgctg ctgctgctgc      120
tgaagccacc gccatagccg ccccccagcc cgcaggctcc cccagaggag aagcgggagg      180
atgagacaga caggccgccc ccgtaggtgc tgggggcgcg gcaggaccct ccggccagga      240
cggaggagat gcggctggag ccgccccgga tgccgccccc gatgccgcag gagcccttca      300
tggagctgga ggaggtgaac tggcggctgc aggtggtcat ggtgcagagg agggaggtga      360
gcgagcgagc agttggctga gtgaagagaa ggtgctcggg taaattggaa agggatgcga      420
gtgctttata ctcgtgggta gggggcgggt ctggcacttt ccattcccct tggctttcat      480
cacccacagg ctagcgccaa ctcccagcca ggtccctcct ctcatccgcc tcatcatgtc      540
tgtcatattt tactggaaac tcattgtttg gagtgttttg ggctttcttg tcccgccagg      600
cgtgattcac aggggggaggt gtgggcctgc aggctacact ttcccatcgg accctgggag      660
tcccagccct caggaacccg cgcactgggc ttagccaggg tgacagagag cagggcctct      720
gcaccttaaa cctagttacc tgctagctct ccatgaactg aatgggcctt taacatccac      780
gtagaggaag cctgctgctg c                                                801

<210> SEQ ID NO 52
<211> LENGTH: 434
<212> TYPE: DNA
<213> ORGANISM: Homo sapiens

<400> SEQUENCE: 52
cgatggagga catcgtcatg gtcacaggga tggcgtcgaa gtaggacgag tgaggcgcga       60
gcgtgaggat ggccgcctcg gtgggcagcg cctgccgccc cttcacgcc acccggtgga      120 agccgccggc gaaccacatg gtgcgcatga tggccttcag caggaagtcc acaaccctgc      180
aaaagagggc gctgcgtcac gcgggcacac gtccgcagtc tcggagtctg tgtgaggcac      240
aggggcggtc ccacgggaga gccctccagg gcgcagtcca ggccacgggc ttcctgtggt      300
cgccgccgct gggacatctg cttgagggaa gaaaagacgc cgcggcttcc tggcctccgc      360
ctgtgtcctc gctggctgcg ctctcaccta cgaaggaggc cgcggggccc tgtgtggtgg      420
tcacgggcca cgcg                                                        434

<210> SEQ ID NO 53
<211> LENGTH: 411
<212> TYPE: DNA
<213> ORGANISM: Homo sapiens

<400> SEQUENCE: 53
cgtccatctc ggccttcgaa ggcacgtgcg tctccatccc ctgccgcttt gacttcccgg       60
atgagctgcg gcccgctgtg gtgcatggtg tctggtactt caatagcccc taccccaaga      120
```

```
actaccccccc ggtggtcttc aagtcgcgca cccaagtagt ccacgagagc ttccagggcc      180
gcagccgcct cctggggggac ctgggcctgc gaaactgcac cctcctgctc agcaacgtca      240
gccccgagct gggcgggaag tactacttcc gtggggacct gggcggctac aaccagtaca      300
ccttctcaga gcacagcgtc ctggatatcg tcagtgagtc cccagcggtt gtgcaggcac      360
cgggagctgg ggcagcgggg cgggaaggag tgtggccgga aggcctcccc g               411

<210> SEQ ID NO 54
<211> LENGTH: 600
<212> TYPE: DNA
<213> ORGANISM: Homo sapiens

<400> SEQUENCE: 54
cgggtggctc caccctgcgt cgggcctcag tcagcccccg ggggaggcca tgaacgccac       60
ggggaccccg gtggccccccg agtcctgcca acagctggcg gccggcgggc acagccggct     120
cattgttctg cactacaacc actcgggccg gctggccggg cgcggggggc cggaggatgg      180
cggcctgggg gccctgcggg ggctgtcggt ggccgccagc tgcctggtgg tgctggagaa      240
cttgctggtg ctggcggcca tcaccagcca catgcggtcg cgacgctggg tctactattg      300
cctggtgaac atcacgctga gtgacctgct cacgggcgcg gcctacctgg ccaacgtgct      360
gctgtcgggg gcccgcacct tccgtctggc gcccgcccag tggttcctac gggagggcct      420
gctcttcacc gccctggccg cctccacctt cagcctgctc ttcactgcag gggagcgctt      480
tgccaccatg gtgcggccgg tggccgagag cggggccacc aagaccagcc gcgtctacgg      540
cttcatcggc ctctgctggc tgctggccgc gctgctgggg atgctgcctt tgctgggctg      600

<210> SEQ ID NO 55
<211> LENGTH: 540
<212> TYPE: DNA
<213> ORGANISM: Homo sapiens

<400> SEQUENCE: 55
cggggcgagc acgtgcacct cgtgaccacc ggctctctag agccccaggc agaggcccag       60
ctctgcagta gggaaggcat cgggagtgcc agggtgaacg tacccaagg gccccggcacg     120
actgacctct cgtgcctgct ctctcccttc ctcgccaagc ccccgtgatg tgggaagcca      180
gcgtgaggcc ggtggggcag ccgccttccc gtggctgtgc caagtccccc cggtcctctg      240
cacatcatgc ctccttccac accctgacag gaagcagctg ggagaagccg ttgggtgcac      300
tcactccctg atttacgaca agttccttcc tcagcgcctc tctctcctgc ctcctcctgc      360
tctcctgccc tcccctgggc ctcggaggt gccacgcaag cccaagaagc atcagcatac      420
tgtccctccc tctcctgtgg ccacgggctc cccagggag ctgagagtag cagcagctca      480
cagcccaagc caccccttgcc cgtttctagg caggtggtgg caccaggcac gaaggaagca     540

<210> SEQ ID NO 56
<211> LENGTH: 224
<212> TYPE: DNA
<213> ORGANISM: Homo sapiens

<400> SEQUENCE: 56
cggtgacccg gccgggtcga agggcagagt tccgctgtca ctagccctcc accgtcctg       60
tgtgctggga tgccctcgcg gcgccgtcca cgccaccgcc gccccctctt gtgggttctg     120
tctcctccgt gtctaggatc ctcctgcatc cgttttttcct tcctcccttc tctccctccg    180
tctgtcttgc ccgcacctga ggttgtcgca gaggcgctga gacg                      224
```

<210> SEQ ID NO 57
<211> LENGTH: 316
<212> TYPE: DNA
<213> ORGANISM: Homo sapiens

<400> SEQUENCE: 57
cgcgggctgc ggggctgcgg ggagggaggg gcgggttcag ggctgtgggc cccgcccggg        60
gcaccgcctg gatcaggcct gaggccggct gcagagaact tgggcaccgc ggaccagatt       120
gctggtcacc aggatgaaaa ataaaaaaga cccaaacagc tcccccgacc ccgccttcgc       180
gcaggcccct ggcgttctgc tcaggggttt ttgtttaatg aagaacgtca acatctggc        240 aaggtcggaa tgattttgcg atgagcaccg cctggattct gcggtgaaag cgactgtgtg       300
cgcgctcacg gcctcg                                                       316

<210> SEQ ID NO 58
<211> LENGTH: 372
<212> TYPE: DNA
<213> ORGANISM: Homo sapiens

<400> SEQUENCE: 58
cgggcgccgc ccccttcct cctccatcag caacaggcgg cgccggccag cctcatagtc        60
agcctcatcc acactgacca gcaggcgaac agcctcccgg cccacagcct ctcgcagggc      120
ctcagtcagg aacacgcccc gcaggcctg cagcagggcg ccactcaggt agtcgcccca      180
gaaggcgtcc agataggaga gctctgagaa cttgatgtca caaaccacag agcccaggtc      240
ccttgagcgc agcactgcgg tggcctgccc aaacacgtcc agctgccgcg ccagcgcctg      300
gggccgccgg gatgccacgc cctgctccaa ggctggccca tgctcgcagt actctgctcg      360
aacccggagc cg                                                           372

<210> SEQ ID NO 59
<211> LENGTH: 258
<212> TYPE: DNA
<213> ORGANISM: Homo sapiens

<400> SEQUENCE: 59
cgcccagggc caggccgttg atgatgacgg ggccccgtt gaggagcact gctggggagc        60
cgctggctgc caggaagctc ccgttcacca ggatggagga ggaagccggg caaggcgcgg      120
gagggccggt ccctgccagg aatatggagc cctgggcagc ggcctcggcg gacactgggg      180
ccgcccctct ctccaggtcc tcaggacttc ggctggactc gtcctcagtc gtgggattcc      240
catcagactc gctggccg                                                     258

<210> SEQ ID NO 60
<211> LENGTH: 398
<212> TYPE: DNA
<213> ORGANISM: Homo sapiens

<400> SEQUENCE: 60
cgccttttcc ttcggtcact cagaccgcgc ccgaggtccc tggtgccccc gcggggagc        60 tgaggtttgc ggtccctcct ggggttcgct tcccgcgggg ctaaaccgcg gcgaccaggg      120 ccccttttctc cactggtgcc ttttccggga aacgctgctc cttagatgga cgaatacgta      180
ctcggtaccc agcacatcct ggacgagtta acttccttaa tttccatatt tgccggagaa      240
ccagctggtt cagagcgcac agcaaacggg agaagttaaa ccaggttccg cgacccagag      300

```
cccagggctg gccccgggga cacccacctg actccgcacc ccccacgaga ggggaggatc    360
cttgcagacc tcacctttgc tggcaacgct gcggcccg                           398
```

<210> SEQ ID NO 61
<211> LENGTH: 220
<212> TYPE: DNA
<213> ORGANISM: Homo sapiens

<400> SEQUENCE: 61

```
cgattcgaga gaggcaggca tccgcggcag cagcttccaa cccagacagg cttaagccgc    60
gcgagggtgc ccgggtgggt ggctgcgcag ggccctacct gggcgggagc ggctgcagag   120
ccctgtccac gcggtgcctc cccagcacgg cacctcccac tccaggctgt tggttacctg   180
gccgggagct ggcggagacc aggatttctc ctcgccgccg                         220
```

<210> SEQ ID NO 62
<211> LENGTH: 599
<212> TYPE: DNA
<213> ORGANISM: Homo sapiens

<400> SEQUENCE: 62

```
cggagctacc cgcggcggcc cgggttcgca tcctcccact gctcagaccg agtcggctcc    60
agcttgcttt gggaagcatt caggaataaa cgtggacagt agcggtcagg aaggagattc   120
ccgtttcccc ttctcccagg aggaaaagag gtaacgctgc cgccactgcc ctctctttcc   180
agggtgggaa cgccgcccga gaccggggta ccccacactc ctccctagcg ctgatcccag   240
cggagctcag gccgcagtcc cctcctgccg gctgcggaag ctcccagaag cggagactca   300
atcgcccccc tgcccctgct accaggccag agtctggagt acagatactg ctccctggg    360 gcctgggtgt gcgaccccag gccggtcatt gcaggtctct gcgcctccct gttcctgact   420
gtgcaatggg cagcgggtca ggggcgcacc gtgggcgcag tacgttccca ggcgccaagg   480
gctgtgactg accgacctgg gcttccaccg cggggcctgg gccatggaga cgctccgggc   540
ccaggaacgg gggacctcgg gtgccccact acctcactcc tagaacgccc accgctcac    599
```

<210> SEQ ID NO 63
<211> LENGTH: 221
<212> TYPE: DNA
<213> ORGANISM: Homo sapiens

<400> SEQUENCE: 63

```
cgccaacttg cggagggggcg ccgaggtctc gccttccagc tccacttgct cctggtcttc    60
cttcttggca gcgttctttt tgtccattgc tgatgcaggt agcgcaggag gatgtttgtc   120
ttttcggtca cgatgatctg ttcagacggg tactctcggg tgggcaggta gactgagggc   180
cgttggttcg aggctttgca cacggagtcc ccgtgaaatc g                       221
```

<210> SEQ ID NO 64
<211> LENGTH: 406
<212> TYPE: DNA
<213> ORGANISM: Homo sapiens

<400> SEQUENCE: 64

```
cggtggcctc tgttgccggc atacactgga aacgcgcatc tgcgtctgtc tgcagagatg    60
cagggtctta gacgcggtgc tggggattcc agtgaaacgc tgggcaggat cccaagtccg   120
ccagcaatgg aatggaagac ccaccgtgat ctaatcgccc accagcagag gccacggagg   180
cggaggcgag ccagccacag ccccgccaac gcgcacgaat cccacgtggc gtgagtcttt   240
```

```
tcacagaccg tgggaaacat gcacaactgc ctggtatcta atttagggac acagcctcgt      300
gacgtaaacc ctgcagaagc acagaggcgt ggcgcacgtg agaattcagg gcagcgggct      360
gcggcagagc gggggaggag gctggaagcg tccctggagc tgcacg                    406
```

<210> SEQ ID NO 65
<211> LENGTH: 241
<212> TYPE: DNA
<213> ORGANISM: Homo sapiens

<400> SEQUENCE: 65

```
cgattgtcct cgaggcacac ggcggggcag agcttggaag cggccgaggt gggggtccct      60
gggtgtggat gtagtgaccc cggagccacg tggagccacc ttcagaccca gagctgaagc     120
aggagggtga ccggtagagc aaggccgtgc acaccccgt tgcagaattg aaaacgcgcc     180
tcaaaataaa accccgtgtt tcacaagaat gcactaattc ccgaagatat ccgggcgcac     240
g                                                                     241
```

<210> SEQ ID NO 66
<211> LENGTH: 273
<212> TYPE: DNA
<213> ORGANISM: Homo sapiens

<400> SEQUENCE: 66

```
cgcataacgt ccccagacaa accgcggccg atgcccatgg acacgagcgt gtatgagagc      60
ccctacagcg acccagagga gctcaaggac aagaagctct tcctgaagcg cgataacctc     120
ctcatagctg acattgaact tggctgcggc aactttggct cagtgcgcca gggcgtgtac     180
cgcatgcgca gtatggccg cccctgccgt ggtgggagca ccgccgcctg gggcagaggg     240
gagtggcttc accgggctgt gggacgggag ccg                                   273
```

<210> SEQ ID NO 67
<211> LENGTH: 280
<212> TYPE: DNA
<213> ORGANISM: Homo sapiens

<400> SEQUENCE: 67

```
cgcgtcaagg ctcagcgctt caccgacgca cccagcccga gaccctccgt tgctctctga      60
ctccgaagga aaatctagtt ccttcgggcg cctgggactc ctttctggag atcagacga     120 gtcgggctcc gcgaagccca tgcgggctgg aggatcggaa accacgcggg agaggatagc     180
gccggtggcg cgaggacgca gactgcagag ctctacgggg aatgggagtt ttctctcgtt     240
cactatggcg tccccggcga cccgaatgga ggctgctgcg                            280
```

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
aagagcccat caggcaggtc                                                  20
```

<210> SEQ ID NO 69
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 69
gtttcttgtc gagcagcacg tggatgatg                                       29

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctccagaact ggaacttcct g                                               21

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtttcttaac ttggagacga cggcatc                                         27

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tggaggacaa tgccctggtg                                                 20

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtttcttggc ttcacctgcg accgtctc                                        28

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccctccgagt ggccagcag                                                  19

<210> SEQ ID NO 75
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 75
gtttctgacc actgccgtgg gaatg                                              25

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cttctcagcc aatgggaaga g                                                  21

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
acgtagaagg acccgaggac                                                    20

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tacagacaaa tcactcagca gc                                                 22

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtttcttgtc tgacactcgg ttgtaggtat t                                       31

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cagcaacagc acccagcttg                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 81
cacaggctca gtcgcggatc                                                        20

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggacgagtta acttccttaa tttc                                                 24

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gtttcttcgc ggaacctggt ttaacttc                                         28

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gcagcaggcc gcggagaag                                                        19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agcagctgtg ccgggccag                                                        19

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
aggaaacctc agtagcaaaa ttg                                                   23

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcgagacttt aggtgtgcat c                                              21

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cgtaggctgc ggtgagctc                                                 19

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gatccatgcc cgctgggatg                                                20

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cagcctagac gtcaagttac ag                                             22

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acgacctccg gatccaactg                                                20

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cccagctggt tggacatgtt g                                              21

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cacttccttc gtggacgcc                                                    19

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gagaagcggg aggatgagac                                                   20

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccgcatctcc tccgtcctg                                                    19

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gccttcagca ggaagtccac                                                   20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cctgtgcctc acacagactc                                                   20

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gtgcatggtg tctggtactt c                                                 21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

```
gaagctctcg tggactactt g                                              21
```

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

```
cagcctgctc ttcactgcag                                                20
```

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

```
agaggccgat gaagccgtag                                                20
```

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102

```
ctccctgatt tacgacaagt tc                                             22
```

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103

```
gacagtatgc tgatgcttct tg                                             22
```

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104

```
aagggcagag ttccgctgtc                                                20
```

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cggatgcagg aggatcctag                                                  20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cggaccagat tgctggtcac                                                  20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cgaccttgcc agatgtttga c                                                21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
agcctcatcc acactgacca g                                                21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tcagagctct cctatctgga c                                                21

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gccaggccgt tgatgatgac                                                  20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gaatatggag ccctgggcag                                                  20